United States Patent
Hills et al.

(10) Patent No.: US 8,492,387 B2
(45) Date of Patent: Jul. 23, 2013

(54) 2-AMINOIMIDAZOLE BETA-SECRETASE INHIBITORS FOR THE TREATMENT OF ALZHEIMER'S DISEASE

(75) Inventors: Ivory D. Hills, Harleysville, PA (US); Craig A. Coburn, Royersford, PA (US); Samuel L. Graham, Schwenksville, PA (US); Keith P. Moore, Harleysville, PA (US); Philippe G. Nantermet, Lansdale, PA (US); Hemaka A. Rajapakse, Wyncote, PA (US); Shawn J. Stachel, Perkasie, PA (US); Hong Zhu, Lansdale, PA (US)

(73) Assignee: Merck, Sharp & Dohme, Corp., Rahway, NJ (US)

( * ) Notice: Subject to any disclaimer, the term of this patent is extended or adjusted under 35 U.S.C. 154(b) by 0 days.

(21) Appl. No.: 12/919,277

(22) PCT Filed: Feb. 18, 2009

(86) PCT No.: PCT/US2009/034377
§ 371 (c)(1),
(2), (4) Date: Aug. 25, 2010

(87) PCT Pub. No.: WO2009/108550
PCT Pub. Date: Sep. 3, 2009

(65) Prior Publication Data
US 2011/0034483 A1 Feb. 10, 2011

Related U.S. Application Data

(60) Provisional application No. 61/067,452, filed on Feb. 28, 2008.

(51) Int. Cl.
| | |
|---|---|
| A61K 31/506 | (2006.01) |
| A61K 31/42 | (2006.01) |
| A61K 31/4174 | (2006.01) |
| A61K 31/4178 | (2006.01) |
| A61K 31/4439 | (2006.01) |
| A61K 31/422 | (2006.01) |
| C07D 233/88 | (2006.01) |
| C07D 403/10 | (2006.01) |
| C07D 403/06 | (2006.01) |
| C07D 413/10 | (2006.01) |
| C07D 401/10 | (2006.01) |

(52) U.S. Cl.
USPC .......... 514/256; 514/341; 514/374; 514/378; 514/397; 514/398; 544/333; 546/271.4; 546/272.7; 548/247; 548/314.4; 548/315.1; 548/326.5; 548/6

(58) Field of Classification Search
None
See application file for complete search history.

(56) References Cited

U.S. PATENT DOCUMENTS
5,834,609 A 11/1998 Horne

FOREIGN PATENT DOCUMENTS
| WO | WO2005/097767 A1 | 10/2005 |
|---|---|---|
| WO | 2006/060109 | 6/2006 |

OTHER PUBLICATIONS

AD, 2012, http://www.webmd.com/alzheimers/guide/treatment-overview.*
Ghosh et al., 2012, 120, 71-83, Journal of Neurochemistry.*
Lempert et al., caplus an 1963:53312.*
Aberie, N.; et al.; Synthesis and biological evaluation of analogues of the anti-tumor alkaloid naamidine A; Bioorganic and Medicinal Chemistry Letters; Jul. 2007, vol. 17, Iss 13, pp. 3741-3744.
Written Opinion for International Application No. PCT/US09/34377 mailed Jul. 13, 2009; 5 pages.
International Search Report for International Application No. PCT/US09/34377; mailed Jul. 13, 2009; 2 pages.
Supplementary European Search Report dated Jan. 16, 2012 for related European Application No. EP 09715236.7; 2 pages.
Ying-Zi, Xu, et. Al.; Oxidative Dimerization of 2-Aminoimidazoles by Molecular Bromine, Synthesis of Parazoanthoxanthin A, The Journal of Organic Chemistry, vol. 61, No. 26, Jan. 1, 1996, pp. 9569-9571.
Ying-Zi, Xu, et. Al.; "Biominetic transformations of 2-aminoimidazole into zoanthoxanthins: Exposing a potential biogenic missing link," Tetrahedron Letters, Elsevier, Amsterdam, NL, vol. 33, No. 31, Jul. 28, 1992, pp. 4385-4388.
Lancini, CC, Lazzare, E, Sartori, C; "Microbial oxidation of aminoimidazoles to nitroimidazoles", J. Antibiotl, vol. 21, No. 6, 1968, pp. 387-392.
Wermuth, C.G.; "Molecular variations based on isosteric replacements:, Practice of Medicinal Chemistry" Jan. 1, 1996; pp. 203-237.

* cited by examiner

*Primary Examiner* — Sun Jae Loewe
(74) *Attorney, Agent, or Firm* — Keith D. MacMillan; Gerard M. Devlin

(57) ABSTRACT

The present invention is directed to 2-aminoimidazole compounds of formula (I)

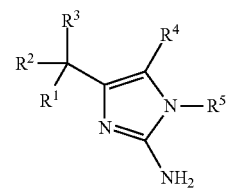

which are inhibitors of the beta-secretase enzyme and that are useful in the treatment of diseases in which the beta-secretase enzyme is involved, such as Alzheimer's disease. The invention is also directed to pharmaceutical compositions comprising these compounds and the use of these compounds and compositions in the treatment of such diseases in which the beta-secretase enzyme is involved.

11 Claims, No Drawings

2-AMINOIMIDAZOLE BETA-SECRETASE INHIBITORS FOR THE TREATMENT OF ALZHEIMER'S DISEASE

FIELD OF THE INVENTION

The invention is directed to 2-aminoimidazole compounds which are useful as inhibitors of the beta secretase enzyme, and are useful in the treatment of diseases in which the beta secretase enzyme is involved, such as Alzheimer's Disease.

BACKGROUND OF THE INVENTION

Alzheimer's disease is characterized by the deposition of amyloid in the brain in the form of extra-cellular plaques and intra-cellular neurofibrillary tangles. The rate of amyloid accumulation is a function of the rates of formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size. The amyloid precursor protein (APP or AβPP) has a receptor-like structure with a large ectodomain, a membrane spanning region and a short cytoplasmic tail. The Aβ domain encompasses parts of both extra-cellular and transmembrane domains of APP, thus its release implies the existence of two distinct proteolytic events to generate its $NH_2$— and COOH— termini. At least two secretory mechanisms exist which release APP from the membrane and generate soluble, COOH-truncated forms of APP ($APP_S$). Proteases that release APP and its fragments from the membrane are termed "secretases." Most $APP_S$ is released by a putative α-secretase which cleaves within the Aβ protein to release α-$APP_S$ and precludes the release of intact Aβ. A minor portion of $APP_S$ is released by a β-secretase ("β-secretase"), which cleaves near the $NH_2$-terminus of APP and produces COOH-terminal fragments (CTFs) which contain the whole Aβ domain.

Thus, the activity of β-secretase or β-site amyloid precursor protein-cleaving enzyme ("BACE") leads to the cleavage of APP, production of Aβ, and accumulation of β amyloid plaques in the brain, which is characteristic of Alzheimer's disease (see R. N. Rosenberg, *Arch. Neurol.*, vol. 59, September 2002, pp. 1367-1368; H. Fukumoto et al, *Arch. Neurol.*, vol. 59, September 2002, pp. 1381-1389; J. T. Huse et al, *J. Biol. Chem.*, vol 277, No. 18, issue of May 3, 2002, pp. 16278-16284; K. C. Chen and W. J. Howe, *Biochem. Biophys. Res. Comm*, vol. 292, pp 702-708, 2002). Therefore, therapeutic agents that can inhibit β-secretase or BACE may be useful for the treatment of Alzheimer's disease.

The compounds of the present invention are useful for treating Alzheimer's disease by inhibiting the activity of β-secretase or BACE, thus preventing the formation of insoluble Aβ and arresting the production of Aβ.

SUMMARY OF THE INVENTION

The present invention is directed to compounds of general formula (I)

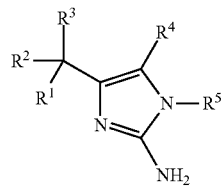

and pharmaceutically acceptable salts thereof, which are useful as inhibitors of the β-secretase enzyme.

The invention is also directed to pharmaceutical compositions which include a therapeutically effective amount of a compound of formula (I), or pharmaceutically acceptable salts thereof, and a pharmaceutically acceptable carrier. The invention is also directed to methods of treating mammals for diseases in which the β-secretase enzyme is involved, such as Alzheimer's disease, and the use of the compounds and pharmaceutical compositions of the invention in the treatment of such diseases.

DETAILED DESCRIPTION OF THE INVENTION

In one embodiment, the present invention is 2-aminoimidazole compounds represented by general formula (I)

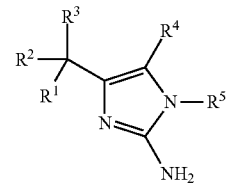

$R^1$ is —$C_{1-6}$alkyl, wherein said alkyl is optionally substituted with one or more
  (a) halo,
  (b) —OH,
  (c) —CN,
  (d) —$C_{1-6}$ alkyl,
  (e) —$C_{2-6}$ alkenyl,
  (f) —$C_{3-6}$ cycloalkyl,
  (g) —$NO_2$,
  (h) —O—$C_{1-6}$ alkyl,
  (i) phenyl, and
$R^2$ is hydrogen, or
$R^1$ and $R^2$ may be linked together to form a carbocyclic ring having from four to nine ring carbon atoms wherein one or more of the ring carbon atoms may be replaced with an oxygen, nitrogen or sulfur, wherein said carbocyclic ring is optionally substituted with one or more
  (a) halogen,
  (b) —$C_{1-6}$ alkyl, or
  (c) —O$C_{1-6}$ alkyl;
$R^3$ is selected from the group consisting of
  (1) —$C_{1-6}$ alkyl,
  (2) —$C_{1-6}$ alkenylene-$C_{6-10}$ aryl,
  (3) —$(CH_2)_n$—$C_{6-10}$ aryl, or
  (4) —$(CH_2)_n$ heteroaryl, wherein said heteroaryl is an aromatic cyclic group having 5 to 12 ring atoms, at least one of which is O, N or S,
wherein said alkyl, alkenylene, aryl, or heteroaryl $R^2$ moiety is optionally substituted with one or more
  (a) halo,
  (b) —OH,
  (c) —CN,
  (d) —$NO_2$,
  (e) —$C_{1-6}$ alkyl
  (f) —$C_{2-6}$ alkenyl
  (g) —$C_{3-6}$ cycloalkyl,
  (h) —O—$C_{1-6}$ alkyl,
  (i) —O—$CH_2$-aryl,
  (j) —$C_{6-10}$ aryl,
  (k) heteroaryl, wherein said heteroaryl is an aromatic cyclic group having 5 to 12 ring atoms, at least one of which is O, N or S, (l) —NR$^{6A}$R$^{6B}$,
(m) —NR$^{6A}$C(=O)R$^{6B}$,
(n) a heterocyclic group having 4 to 8 ring atoms, wherein one ring atom is a heteroatom selected from the group consisting of nitrogen, sulfur and oxygen,
(o) —SO$_2$C$_{1-3}$ alkyl,
(p) —SO$_2$NR$^{6A}$R$^{6B}$, and
(q) —CONR$^{6A}$R$^{6B}$,
wherein said alkyl, alkenyl, cycloalkyl, aryl and heteroaryl moiety is optionally substituted with one or more
(I) halo,
(II) —C$_{1-6}$ alkyl, wherein said alkyl is optionally substituted with one or more fluoro,
(III) —O—C$_{1-6}$ alkyl, wherein said alkyl is optionally substituted with one or more fluoro,
(IV) —NHSO$_2$R$^9$, or
(V) OH;
R$^4$ is selected from the group consisting of
(1) hydrogen, or
(2) —C$_{1-6}$ alkyl,
wherein said alkyl is optionally substituted with one or more
(a) halogen
(b) hydroxyl,
(c) —C$_{6-10}$ aryl,
(d) heteroaryl, wherein said heteroaryl is an aromatic cyclic group having 5 to 12 ring atoms, at least one of which is O, N or S,
(e) —OC$_{1-4}$ alkyl, or
(f) —C(=O)OR$^9$,
and wherein said alkyl, aryl or heteroaryl is optionally substituted with one or more
(I) hydroxy,
(II) fluoro,
(III) —C$_{1-4}$ alkyl, optionally substituted by fluoro; or
(IV) —OC$_{1-4}$ alkyl;
R$^5$ is selected from the group consisting of
(1) hydrogen,
(2) —C$_{1-6}$ alkyl, or
(3) a heterocyclic group having 4 to 8 ring atoms, wherein at least one ring atom is a heteroatom selected from the group consisting of nitrogen, sulfur and oxygen, or wherein said alkyl or heterocyclyl is optionally substituted with one or more
(a) halogen
(b) hydroxyl,
(c) —C$_{6-10}$ aryl,
(d) heteroaryl, wherein said heteroaryl is an aromatic cyclic group having 5 to 12 ring atoms, at least one of which is O, N or S,
(e) a heterocyclic group having 4 to 8 ring atoms, wherein at least one ring atom is a heteroatom selected from the group consisting of nitrogen, sulfur and oxygen, or
(f) —OC$_{1-4}$ alkyl,
(g) —CN,
(h) —C(=O)—OR$^9$,
wherein said alkyl, aryl, heteroaryl or heterocyclic group is optionally substituted with one or more
(I) hydroxy,
(II) fluoro,
(III) —C$_{1-4}$ alkyl, optionally substituted by fluoro,
(IV) —OC$_{1-4}$ alkyl,
(V) —(CH$_2$)$_n$—C$_{6-10}$ aryl,
(VI) heteroaryl, or
(VII) —C(=O)OR$^9$;
R$^{6A}$, R$^{6B}$ and R$^{6C}$ are independently selected from the group consisting of:
(1) hydrogen,
(2) halogen,
(3) C$_{1-6}$alkyl,
(4) O—C$_{1-6}$alkyl,
(5) —NO$_2$,
(6) cyano,
(7) OH
(8) —(CH$_2$)$_m$aryl
(9) —NR$^7$R$^8$, wherein R$^7$ and R$^8$ are selected from the group consisting of
(I) hydrogen,
(II) —C$_{1-6}$ alkyl,
(III) —C$_{3-6}$ cycloalkyl,
or R$^7$ and R$^8$ are linked together with the nitrogen to which they are both attached to form a 2-6 membered carbocyclic ring, wherein one or two of the ring carbon atoms is replaced by a nitrogen, oxygen or sulfur,
wherein said R$^{6A}$, R$^{6B}$ or R$^{6C}$ alkyl or aryl moiety is optionally substituted with one or more
(a) halo,
(b) —C$_{1-6}$ alkyl,
(c) —O—C$_{1-6}$ alkyl, and
(d) -aryl,
wherein said wherein said alkyl or aryl is optionally substituted with one or more halo,
R$^9$ is selected from the group consisting of:
(1) hydrogen,
(2) C$_{1-4}$alkyl, or
(3) —C$_{3-8}$ cycloalkyl,
n is 0 or 1;
m is 0, 1, 2 or 3;
provided that when R$^2$, R$^4$ and R$^5$ are each hydrogen, then R$^1$ is not 4-methoxyphenyl and R$^3$ is not (1-methoxy-4-nitrophenyl)methylene;
and pharmaceutically acceptable salts thereof.

The invention is also directed to methods of treating mammals for diseases in which the β-secretase enzyme is involved, such as Alzheimer's disease, by administering a therapeutically effective amount of a compound of any of the embodiments of formula (I).

The invention is also directed to pharmaceutical compositions which include an effective amount of a compound of any of the embodiments of formula (I) or pharmaceutically acceptable salts thereof, and a pharmaceutically acceptable carrier.

The invention is further directed to a method for the manufacture of a medicament or a composition for inhibiting β-secretase enzyme activity in humans and animals comprising combining a compound of any of the embodiments of formula (I) or a pharmaceutically acceptable salt thereof, with a pharmaceutical carrier or diluent.

In one embodiment, the invention is directed to methods of inhibiting BACE1 enzyme activity, by administering a therapeutically effective amount of a compound of any of the embodiments of formula (I).

In another embodiment, the invention is directed to methods of inhibiting BACE2 enzyme activity, by administering a therapeutically effective amount of a compound of any of the embodiments of formula (I).

The invention is also directed to a method for the manufacture of a medicament or a composition for treating Alzheimer's Disease in humans, comprising combining a compound of any of the embodiments of formula (I) or a pharmaceutically acceptable salt thereof, with a pharmaceutical carrier or diluent.

Suitable R$^1$ aryl groups include phenyl, napthyl, indane and 2,3-dihydro-1H-indene.

In particular embodiments, R$^1$ is phenyl, which is optionally substituted with one or more
(a) halo,
(b) —NO$_2$,
(c) —CN,
(d) —C$_{1-6}$ alkyl, or
(h) —O—C$_{1-6}$ alkyl (for example, methoxy).

Exemplary $R^1$ groups include phenyl, 4-methoxyphenyl, 3-methoxyphenyl, 2-methoxyphenyl, 2-bromo-4-methoxyphenyl, 4-chlorophenyl, 3-fluoro-4-methoxyphenyl, 2-nitro-4,5-dimethoxyphenyl and 2-bromo-4,5-dimethoxyphenyl.

In particular embodiments of the invention, $R^2$ is hydrogen.

In alternative embodiments, $R^1$ and $R^2$ are linked together to form a carbocyclic ring having from four to seven ring carbon atoms wherein one or more of the ring carbon atoms may be replaced with an oxygen, nitrogen or sulfur, optionally substituted with halogen or —O—$C_{1-6}$ alkyl.

An exemplary $R^1/R^2$ group is 2,3-dihydro-1H-inden-1-yl, cyclopentyl, cyclohexyl and piperidinyl.

In particular embodiments of the invention, $R^3$ is selected from the group consisting of:
(1) benzyl,
(2) —(CH$_2$) napthyl,
(3) —(CH$_2$) heteroaryl (for example, pyridyl, benzothienyl, thienyl and benzodioxan),
wherein said aryl or heteroaryl moiety is optionally substituted with one or more
(a) halo,
(b) —NO$_2$,
(c) —CN,
(d) —$C_{1-6}$ alkyl,
(e) —$C_{2-6}$ alkenyl,
(e) —$C_{3-6}$ cycloalkyl,
(f) —O—$C_{1-6}$ alkyl,
(h) aryl (for example, phenyl),
(i) heteroaryl (for example, thienyl, furan, imidazolyl and isoxazolyl),
wherein said alkyl, aryl or heteroaryl moiety is optionally substituted with one or more
(I) halo,
(II) —$C_{1-6}$ alkyl, wherein said alkyl is optionally substituted with one or more fluoro,
(III) —O—$C_{1-6}$ alkyl, wherein said alkyl is optionally substituted with one or more fluoro,
(IV) —NSO$_2$R$^9$, or
(V) OH.

In particular embodiments of the invention, $R^4$ is hydrogen. In alternative embodiments, $R^4$ is a $C_{1-6}$ alkyl group, which is substituted by one or more
(a) halogen,
(b) hydroxyl,
(c) —$C_{6-10}$ aryl,
(d) heteroaryl, or
(e) —C(=O)OR$^9$,
and wherein said alkyl, aryl or heteroaryl is optionally substituted with one or more
(I) hydroxy,
(II) fluoro, or
(III) —OC$_{1-4}$ alkyl.

For example, $R^4$ may be a —CH(OH)-aryl (for example, phenyl), —CH(OH)-heteroaryl (for example, pyridyl or imidazolyl), —CH(OH)-alkyl or —CH(OH)—C(=O)OR$^9$.

Preferably, when $R^4$ is other than hydrogen, then $R^1$ and $R^2$ are not linked together.

In particular embodiments of the invention, $R^5$ is hydrogen, methyl or ethyl. In alternative embodiments, $R^5$ is a substituted $C_{1-6}$ alkyl group, which is substituted by one or more
(a) halogen,
(b) hydroxyl,
(c) —$C_{6-10}$ aryl,
(d) heteroaryl,
(e) a heterocyclic group having 4 to 8 ring atoms, wherein at least one ring atom is a heteroatom selected from the group consisting of nitrogen, sulfur and oxygen, or
(f) —$C_{1-6}$ alkyl,
wherein said alkyl, aryl, heteroaryl or heterocyclic group is optionally substituted with one or more
(I) hydroxy,
(II) fluoro, or
(III) —OC$_{1-4}$ alkyl.

For example, $R^5$ may be
(1) —$C_{1-6}$ alkylene-phenyl (for example, benzyl or phenethyl), wherein the benzyl moiety is optionally substituted as described above,
(2) —$C_{1-6}$ alkylene substituted with hydroxyl,
(3) —$C_{1-6}$ alkylene substituted with a heterocyclic group, such as 1,3-dioxolane or piperidine,
(4) -$_{1-6}$alkylene-heteroaryl (for example pyridine, pyrazole, indole and dihydroindole), wherein the heteroaryl moiety is optionally substituted as described above.

Exemplary $R^5$ groups include hydrogen, methyl, ethyl, isopropyl, benzyl and phenethyl.

Within the genus of compounds of formula (I), there is a subgenus of compounds of formula (II):

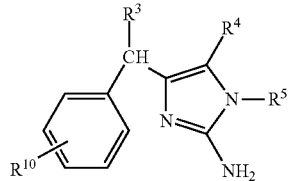

and pharmaceutically acceptable salts thereof, wherein $R^3$, $R^4$ and $R^5$ are as described above, and wherein $R^{10}$ is optionally present at one or more of the ring carbon atoms, and each $R^{10}$ is selected from the group consisting of
(a) halo,
(b) —OH,
(c) —CN,
(d) —$C_{1-6}$ alkyl,
(e) —$C_{2-6}$ alkenyl,
(f) —$C_{3-6}$ cycloalkyl,
(g) —NO$_2$,
(h) —O—$C_{1-6}$ alkyl, and
(i) phenyl.

In particular embodiments, $R^{10}$ is selected from
(a) halo,
(b) —NO$_2$,
(c) —CN,
(d) —$C_{1-6}$ alkyl, or
(e) —O—$C_{1-6}$ alkyl (for example, methoxy).

Within the genus of compounds of formula (I), there is a subgenus of compounds of formula (III):

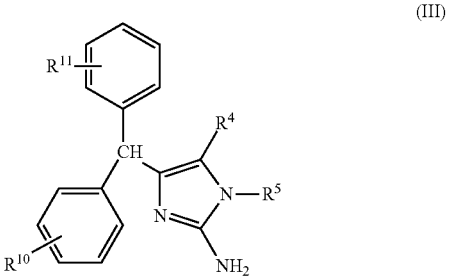

(III)

and pharmaceutically acceptable salts thereof, wherein $R^3$, $R^4$, $R^5$ and $R^{10}$ are as described above, and wherein $R^{11}$ is optionally present at one or more of the ring carbon atoms, and each $R^{11}$ is selected from the group consisting of
(a) halo,
(b) —NO$_2$,
(c) —CN, (d) —$C_{1-6}$ alkyl,
(e) —$C_{2-6}$ alkenyl,
(f) —$C_{3-6}$ cycloalkyl,
(g) —O—$C_{1-6}$ alkyl,
(h) aryl (for example, phenyl),
(i) heteroaryl (for example, thienyl, furan, imidazolyl and isoxazolyl),
wherein said alkyl, aryl or heteroaryl moiety is optionally substituted with one or more
(I) halo,
(II) —$C_{1-6}$ alkyl, wherein said alkyl is optionally substituted with one or more fluoro,
(III) —O—$C_{1-6}$ alkyl, wherein said alkyl is optionally substituted with one or more fluoro,
(IV) —$NSO_2R^9$, or
(V) OH.

Within the genus of compounds of formula (I), there is a subgenus of compounds of formula (IV):

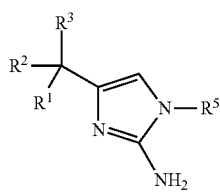

and pharmaceutically acceptable salts thereof, wherein $R^1$, $R^2$, $R^3$ and $R^5$ are as described above.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Suitable alkyl groups for use in the invention are $C_{1-6}$ alkyl groups, having from one to six carbon atoms. Exemplary alkyl groups include methyl, ethyl, n-propyl, isopropyl, n-butyl, isobutyl, tert-butyl, pentyl, hexyl, and the like.

The term "alkylene" means an alkyl group as defined above, having two radicals.

The term "$C_0$alkyl" or "$C_0$alkylene" for example in the term "—$C_0$alkyl-$C_{6-12}$ aryl", refers to a bond.

As used herein, the term "alkenyl," by itself or as part of another substituent, means a straight or branched chain hydrocarbon radical having a single carbon-carbon double bond and the number of carbon atoms designated (e.g., $C_{2-10}$ alkenyl means an alkenyl group having from two to ten carbon atoms). Suitable alkenyl groups for use in the invention are $C_{2-6}$ alkenyl groups, having from two to six carbon atoms. Exemplary alkenyl groups include ethenyl and propenyl.

The term "alkenylene" means an alkenyl group as defined above, having two radicals.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, as well as bridged and fused ring carbocycles, such as spiro fused ring systems.

Suitable cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantly and norbornyl. Exemplary fused cycloalkyl groups include decahydronaphthalene.

The term "cycloalkylene" refers to a cycloalkyl group as defined above, having two radicals.

As used herein, the term "cycloalkenyl," by itself or as part of another substituent, means a saturated cyclic hydrocarbon radical having a single C=C double bond and the number of carbon atoms designated (e.g., $C_{3-12}$ cycloalkenyl means a cycloalkenyl group having from three to twelve carbon atoms).

Suitable cycloalkenyl groups for use in the invention are monocyclic $C_{3-8}$ cycloalkenyl groups, having from three to eight carbon atoms. Exemplary monocyclic cycloalkenyl groups include cyclopropenyl, cyclobutenyl, cyclopentenyl, cyclohexenyl and the like.

The term "cycloalkenylene" refers to a "cycloalkenyl" group as defined above having two radicals.

As used herein, the term "heterocyclic," by itself or as part of another substituent, means a cycloalkyl group as defined above, in which one or more of the ring carbon atoms is replaced with a heteroatom (such as N or O). Suitable non-aromatic heterocyclic groups for use in the invention include piperidinyl, piperazinyl, morpholinyl, tetrahydropyranyl, tetrahydrofuranyl, pyrrolidinyl, pyrazolidinyl and imidazolildinyl. In certain embodiments, heterocyclic groups for use in the invention have four to eight ring atoms and a single nitrogen or oxygen heteroatom.

When a heterocyclic group as defined herein is substituted, the substituent may be bonded to a ring carbon atom of the heterocyclic group, or to a ring heteroatom (i.e., a nitrogen, oxygen or sulfur), which has a valence which permits substitution. Similarly, when a heterocyclic group is defined as a substituent herein, the point of attachment may be at a ring carbon atom of the heterocyclic group, or on a ring heteroatom (i.e., a nitrogen, oxygen or sulfur), which has a valence which permits attachment.

As used herein, the term "aryl," by itself or as part of another substituent, means an aromatic or cyclic radical having the number of carbon atoms designated (e.g., $C_{6-10}$ aryl means an aryl group having from six to ten carbons atoms). The term "aryl" includes multiple ring systems (such as fused ring systems) as well as single ring systems, and includes multiple ring systems wherein part of the molecule is aromatic and part is non-aromatic. A suitable single ring aryl group for use in the invention is phenyl. Suitable fused ring aryl groups include naphthyl, tetrahydronaphthyl and indanyl.

The term "halo" or "halogen" includes fluoro, chloro, bromo and iodo.

As used herein, the term "heteroaryl," by itself or as part of another substituent, means an aromatic cyclic group having at least one ring heteroatom (O, N or S). The term "heteroaryl" includes multiple ring systems as well as single ring systems. Exemplary heteroaryl groups have from 5 to 12 ring atoms. Exemplary heteroaryl groups include pyrazinyl, pyrazolyl, pyridazinyl, pyridyl, pyrimidinyl, pyrrolyl, tetrazolyl, furanyl, imidazolyl, indazolyl, triazinyl, pyranyl, thiazolyl, thienyl, triazolyl, oxazolyl, isoxazolyl, thiazolyl, oxadiazolyl, indolyl, quinolinyl, isoquinolinyl, benzimidazolyl, benzofuranyl, indynyl and benzoxazolyl.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment.

As used herein, the term "beta-secretase" or "β-secretase" refers to an enzyme that is sometimes known in the literature as "BACE", "BACE1" (see, e.g., Vassar et al., 1999, *Science* 286:735-741), or "BACE2" (see, e.g., Farzan et al., 2000, *PNAS* 97:9712-9717). BACE1 is a 501 amino acid membrane-bound aspartic protease. BACE1 has all the known functional properties and characteristics of β-secretase. BACE2, also called Asp-1 or memapsin-1, is a second member of the BACE family of membrane-bound aspartic proteases. See Roggo, *Current Topics in Medicinal Chemistry*, 2002, 2:359-370, for a further discussion of the differences between BACE1 and BACE2.

The compounds of the invention are inhibitors of both the BACE1 and BACE2 enzyme.

The compounds of formula (I) have at least one asymmetric center. Additional asymmetric centers may be present depending upon the nature of the various substituents on the molecule.

Compounds with asymmetric centers give rise to enantiomers (optical isomers), diastereomers (configurational isomers) or both. All of the possible enantiomers and diastereomers in mixtures (as pure or partially purified compounds) are included within the scope of formula (I).

Compounds described herein may contain one or more double bonds, and may thus give rise to cis/trans isomers as well as other configurational isomers. The compounds of formula (I) include all such possible isomers as well as mixtures of such isomers.

Formula (I) is shown above without a definite stereochemistry at certain positions. Figure (I) as depicted includes all stereoisomers of formula (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The term "substantially pure" means that the isolated material is at least 90% pure, as assayed by analytical techniques known in the art. In one embodiment, the isolated material is at least 95% pure. In another embodiment, the isolated material is at least 99% pure.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like. Particular salts are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular salts are the citric, hydrobromic, hydrochloric, trifluoroacetic, maleic, phosphoric, sulfuric, fumaric, and tartaric acids.

The present invention is directed to the use of the compounds of formulas (I) to (III) disclosed herein as inhibitors of β-secretase enzyme activity or β-site amyloid precursor protein-cleaving enzyme ("BACE") activity, in a patient or subject such as a mammal in need of such inhibition, comprising the administration of an effective amount of the compound. The terms "β-secretase enzyme," "β-site amyloid precursor protein-cleaving enzyme," and "BACE" are used interchangeably in this specification. In addition to humans, a variety of other mammals can be treated according to the method of the present invention.

The compounds of the present invention have utility in treating, ameliorating, controlling or reducing the risk of Alzheimer's disease. For example, the compounds may be useful for the prevention of dementia of the Alzheimer's type, as well as for the treatment of early stage, intermediate stage or late stage dementia of the Alzheimer's type. The compounds may also be useful in treating, ameliorating, controlling or reducing the risk of diseases mediated by abnormal cleavage of amyloid precursor protein (also referred to as APP), and other conditions that may be treated or prevented by inhibition of β-secretase. Such conditions include mild cognitive impairment, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes and atherosclerosis.

The subject or patient to whom the compounds of the present invention is administered is generally a human being, male or female, in whom inhibition of β-secretase enzyme activity is desired, but may also encompass other mammals, such as dogs, cats, mice, rats, cattle, horses, sheep, rabbits, monkeys, chimpanzees or other apes or primates, for which inhibition of β-secretase enzyme activity or treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

Examples of combinations of the compounds of the present invention with other drugs in either unit dose or kit form include combinations with anti-Alzheimer's agents, for example other beta-secretase inhibitors or gamma-secretase inhibitors; glycine transport inhibitors, tau phosphorylation inhibitors; blockers of Aβ oligomer formation; p25/CDK5 inhibitors; HMG-CoA reductase inhibitors; PPAR gamma agonists, such as pioglitazone and rosiglitazone; NK1/NK3 receptor antagonists; NSAID's including ibuprofen; vitamin E; anti-amyloid antibodies, including anti-amyloid humanized monoclonal antibodies; COX-2 inhibitors; anti-inflammatory compounds, such as (R)-flurbiprofen; CB-1 receptor antagonists or CB-1 receptor inverse agonists; antibiotics such as doxycycline and rifampin; N-methyl-D-aspartate (NMDA) receptor antagonists, such as memantine and neramexane; MET kinase inhibitors; LCAT modulators; thrombin receptor antagonists; NR2B antagonists; androgen receptor modulators; acetylcholinesterase inhibitors such as galantamine, rivastigmine, donepezil, and tacrine; mGluR5 modulators; mGluR1 modulators; mGluR2 antagonists; growth hormone secretagogues such as ibutamoren, ibutamoren mesylate, and capromorelin; histamine $H_3$ antagonists; AMPA agonists; PDE 4 inhibitors; PDE 10 inhibitors; GABAA inverse agonists; GABAA a 5 receptor ligands; GABAB receptor ligands; potassium channel blockers; neuronal nicotinic agonists; nitric oxide synthase inhibitors; 5-HT6 receptor modulators; 5-HT2A receptor modulators; potassium channel modulators; PI3k inhibitors; orexin receptor antagonists; IKKβ inhibitors; microtubule affinity regulating kinase (MARK) inhibitors; glycogen synthase kinase 3 (GSK3) inhibitors; macrophage migration inhibitory factor inhibitors; P-450 inhibitors, such as ritonavir; or other drugs that affect receptors or enzymes that either increase the efficacy, safety, convenience, or reduce unwanted side effects or toxicity of the compounds of the present invention. The foregoing list of combinations is illustrative only and not intended to be limiting in any way.

In the pharmaceutical composition the active compound, which is a compound of the invention, is included in an amount sufficient to produce the desired effect upon the process or condition of diseases. Accordingly, the pharmaceutical compositions of the present invention encompass any composition made by admixing a compound of the invention and a pharmaceutically acceptable carrier.

The carrier may take a wide variety of forms depending on the form of preparation desired for administration, e.g., oral or parenteral (including intravenous). Thus, the pharmaceutical compositions of the invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain a compound of the invention in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a composition of this invention may be prepared by compression or molding, optionally with one or more accessory ingredients or adjuvants. Compressed tablets may be prepared by compressing, in a suitable machine, a compound of the invention in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. In certain embodiments, each tablet contains from about 0.1 mg to about 500 mg of the active ingredient and each cachet or capsule contains from about 0.1 mg to about 500 mg of the compound of the invention.

Compositions for oral use may also be presented as hard gelatin capsules wherein the compound of the invention is mixed with an inert solid diluent, for example, calcium carbonate, calcium phosphate or kaolin, or as soft gelatin capsules wherein the compound of the invention is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the compound of the invention in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound of the invention, to produce a cream or ointment having a desired consistency.

Pharmaceutical compositions of this invention can also be in a form suitable for rectal administration wherein the carrier is a solid. Suitable carriers include cocoa butter and other materials commonly used in the art.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise-undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant. By "pharmaceutically acceptable" it is meant the carrier, diluent or excipient must be compatible with the other ingredients of the formulation and not deleterious to the recipient thereof.

Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the invention to obtain a desired pharmacologic and/or physiologic effect. The effect may be prophylactic in terms of completely or partially preventing a disease or symptom thereof, and/or may be therapeutic in terms of a partial or complete cure for a disease and/or adverse affect attributable to the disease. Treatment includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The terms "individual," "subject," and "patient," used interchangeably herein, refer to a mammal, including, but not limited to, murines, simians, humans, mammalian farm animals, mammalian sport animals, and mammalian pets.

The compositions containing compounds of the invention may conveniently be presented in unit dosage form and may be prepared by any of the methods well known in the art of pharmacy.

The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The compositions containing compounds of the invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating, ameliorating, controlling or reducing the risk of Alzheimer's disease or other diseases for which compounds of the invention are indicated, generally satisfactory results are obtained when the compounds of the invention are administered at a daily dosage of from about 0.1 mg to about 100 mg per kg of animal body weight. For example, the compounds may be given as a single daily dose or in divided doses two to six times a day, or in sustained release form. The total daily dosage is from about 1.0 mg to about 2000 mg (for example, from about 0.1 mg to about 20 mg per kg of body weight). In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, for example once or twice per day.

The amount of the compound of the invention that may be combined with the carrier materials to produce a single dosage form will vary depending upon the host treated and the particular mode of administration. For example, a formulation intended for the oral administration to humans may conveniently contain from about 0.005 mg to about 2.5 g of a compound of the invention, compounded with an appropriate and convenient amount of carrier material. Unit dosage forms will generally contain between from about 0.005 mg to about 1000 mg of the compound of the invention, typically 0.005 mg, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The utility of the compounds in accordance with the present invention as inhibitors of β-secretase enzyme activity may be demonstrated by methodology known in the art. Enzyme inhibition is determined as follows.

ECL Assay: A homogeneous end point electrochemiluminescence (ECL) assay is performed using a biotinylated BACE substrate. The Km of the substrate is approximated at 50 μM. A typical reaction contains approximately 0.6 nM enzyme, 0.25 μM of the substrate, and buffer (50 mM Pipes, pH 6.5, 0.1 mg/ml BSA, 0.2% CHAPS, 15 mM EDTA and 1 mM deferoxamine) in a total reaction volume of 100 μl. The reaction proceeds for 1-2 hrs and is then stopped by the addition of 150 μL of a quench cocktail solution (25 μM Tris-HCl, pH 8.0, 50 μL INC buffer (2% BSA, 0.2% Tween-20 and 0.05% sodium azide diluted in phosphate buffered saline (PBS) plus 75 μL, PBS), containing streptavadin coated magnetic beads and ruthenylated antibody which specifically recognizes the C-terminal residue of the product. The samples are subjected to M-384 (Igen Inc., Gaithersburg, Md.) analysis. Under these conditions, less than 10% of substrate is processed by BACE 1. The enzyme used in these studies is soluble (transmembrane domain and cytoplasmic extension excluded) human protein produced in a baculovirus expression system. To measure the inhibitory potency for compounds, 10 concentrations of inhibitors are prepared starting from 200 μM with three fold series dilution. Solutions of the inhibitor in DMSO are included in the reaction mixture (final DMSO concentration is 10%). All experiments are conducted at rt using the standard reaction conditions described above. To determine the $IC_{50}$ of the compound, a four parameter equation is used for curve fitting. The errors in reproducing the dissociation constants are typically less than two-fold.

In particular, the compounds of the following examples had activity in inhibiting the beta-secretase enzyme in the aforementioned assay, generally with an $IC_{50}$ from about 10 nM to 200 μM. Such a result is indicative of the intrinsic activity of the compounds in use as inhibitors of beta-secretase enzyme activity.

Exemplary $IC_{50}$ values for representative compounds of the invention (as described in the following Examples) are provided below in Table 1.

TABLE 1

| Example | $IC_{50}$(μM) |
| --- | --- |
| 2 | 5 |
| 3 | 12 |
| 7 | 0.9 |
| 34 | 11 |
| 41 | 27 |
| 55 | 17 |
| 111 | 3.2 |
| 114 | .063 |
| 115 | 3.3 |

Several methods for preparing the compounds of this invention are illustrated in the Schemes and Examples herein. Starting materials are made according to procedures known in the art or as illustrated herein. The following examples are provided so that the invention might be more fully understood. These examples are illustrative only and should not be construed as limiting the invention in any way.

One of the methods for preparing compounds of this invention is illustrated in Scheme 1. Carboxylic acids (1) can be activated using standard reagents such as DCC, thionyl chloride or an isobutylchloroformate/N-methylmorpholine combination. Subsequent addition of diazomethane affords a diazoketone (2), which can be converted to a bromo-ketone (3) via addition of 48% HBr (aq). The bromide can be combined with N-acetyl guanidine to furnish an acetyl-protected 2-aminoimidazole (4). Acid mediated cleavage of the acetyl group provides 5 as a final target or an intermediate that can be elaborated via the addition of an aldehyde to yield 6. Examples 1 and 2 utilize Scheme 1.

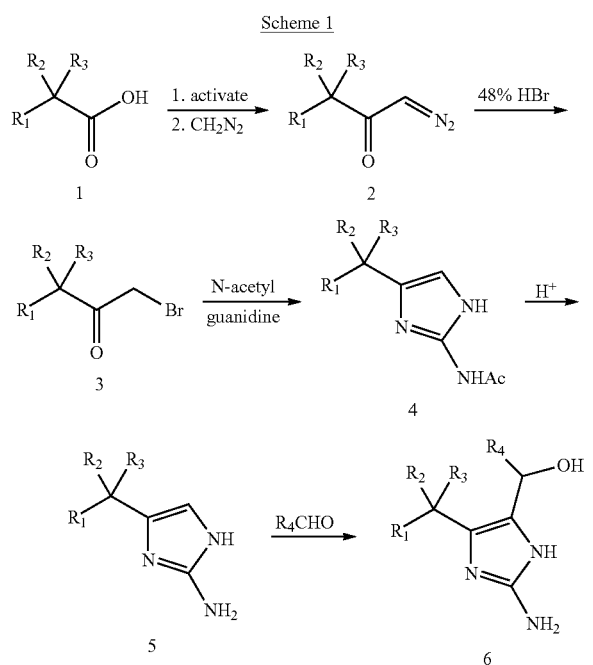

Another method for preparing compounds of this invention is illustrated in Scheme 2. Bromo-ketones (3) that have been acquired via the general method shown in Scheme 1, 3 or 4 can be combined with primary amines to furnish amino-ketones (7). Subsequent treatment of 7 with S-ethylisothiourea under basic conditions provides the desired 2-aminoimidazoles (8). Example 3 utilizes Scheme 2.

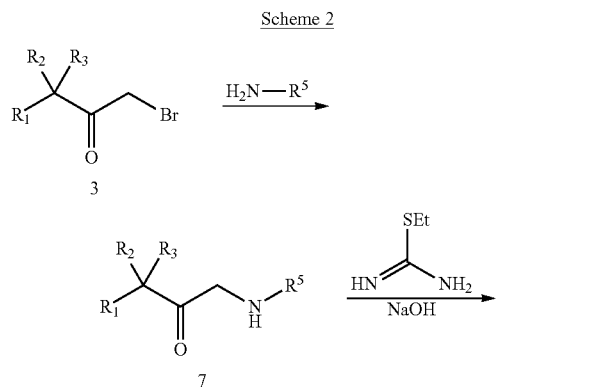

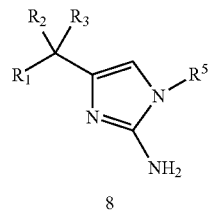

An alternative method for preparing compounds of this invention is illustrated in Scheme 3. Carboxylic acids (1) can be activated using standard reagents such as DCC, thionyl chloride or an isobutylchloroformate/N-methylmorpholine combination; subsequent addition of the Weinreb amine (N,O-Dimethylhydroxylamine) provides the Weinreb amide, which can then be treated with methyl Grignard to furnish the methyl ketone (9). Treatment of the ketone with base and TMS-Cl followed by addition of phenyltrimethylammonium tribromide affords bromo-ketone (3). This bromo-ketone intermediate can be further converted to the target 2-aminoimidazoles via the route described in Scheme 2. Example 4 (steps A-C) utilizes Scheme 3.

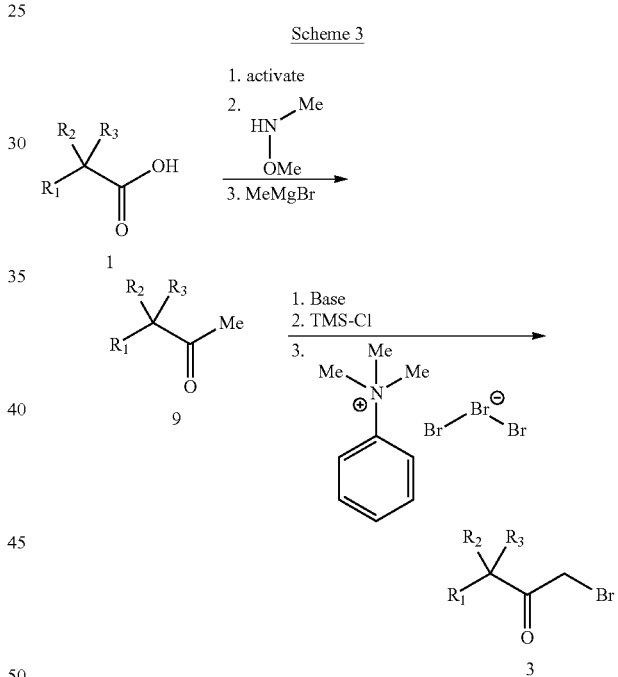

A variant to the route depicted in Scheme 3 is shown in Scheme 4. Addition of Trimethylsilylmethyl lithium to methyl ester 10 provides the intermediate methyl ketone 9, which can be elaborated to bromo-ketone 3 in the standard manner. Example 5 utilizes Scheme 4.

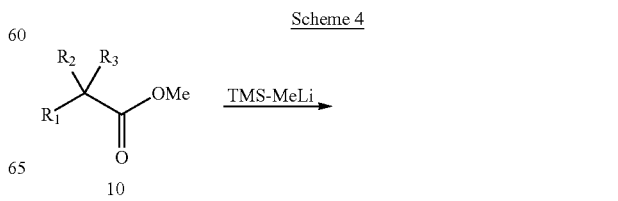

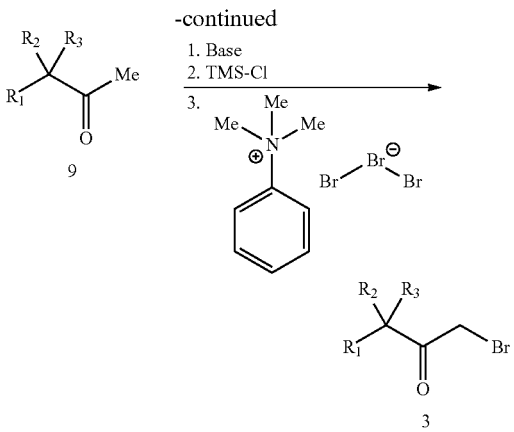

2-aminoimidazole derivatives can also be acquired by performing transformations on an aminoimidazole bearing intermediate such as 12. This is illustrated in Scheme 5 in which a bromo-aromatic is used with a standard palladium-catalyzed cross-coupling reaction to furnish a more elaborate 2-aminoimidazole. Example 4 (step D) utilizes Scheme 5.

Scheme 5

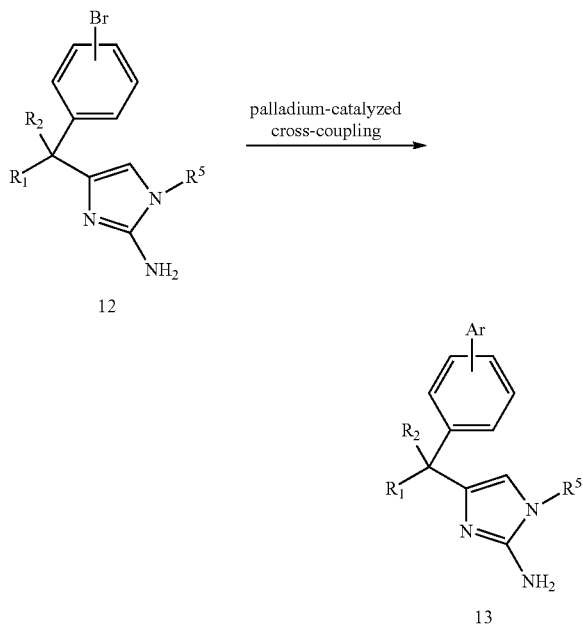

Example 1

4-{(1S)-1-(4-methoxylphenyl)-2-[4-(trifluoromethyl)phenyl]ethyl}-1-H-imidazole-2-amine

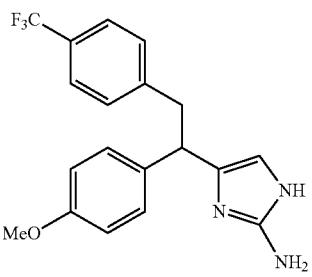

Step A: To a −78° C. tetrahydrofuran solution containing (4S)-4-benzyl-3-[(4-methoxyphenyl)acetyl]-1,3-oxazolin-2-one (3.27 g, 10.1 mmol) was added a 1M tetrahydrofuran solution of NaHMDS (12.1 mL, 12.1 mmol). The mixture was stirred at −78° C. for 30 minutes. 1-(bromomethyl)-4-(trifluoromethyl)benzene (4.81 g, 20.1 mmol) was added and the reaction was stirred for 4 h. The reaction was quenched with aqueous sodium bicarbonate and then extracted into EtOAc (3×50 mL) and the combined organic washings were dried over MgSO4 and evaporated. The resulting residue was purified by column chromatography (90/10 hexanes/EtOAc to 75/25 hexanes/EtOAc) to afford 2.98 g (61%) of (4S)-4-benzyl-3-{(2S)-2-(4-methoxyphenyl)-3-[4-(trifluoromethyl)phenyl]propanoyl}-1,3-oxazoidin-2-one.

Step B: (4S)-4-benzyl-3-{(2S)-2-(4-methoxyphenyl)-3-[4-(trifluoromethyl)phenyl]propanoyl}-1,3-oxazoidin-2-one (2.98 g, 6.17 mmol) from Step A was dissolved in 78 mL (3:1) THF:methanol and cooled to 0° C. A solution of LiOH (0.52 g, 12.3 mmol) in 2.5 mL H2O2 and 2.5 mL H2O was added and the reaction was stirred at 0° C. for 1 h. The reaction was quenched with a saturated solution of sodium thiosulfate and extracted with dichoromethane (3×30 mL). The aqueous layer was acidified with 1 N HCl and extracted with ethyl acetate (3×30 mL). The combined organic layers were dried over MgOS4, filtered and concentrated to provide (2S)-2-(4-methoxyphenyl)-3-[4-(trifluoromethyl)phenyl]propanoic acid (1.6 g, 80%).

Step C: To a room temperature solution of (2S)-2-(4-methoxyphenyl)-3-[4-(trifluoromethyl)phenyl]propanoic acid (1.6 g, 4.95 mmol) in 20 mL of tetrahydrofuran was added N-methylmorpholine (0.52 g, 5.2 mmol). Isobutyl chloroformate (0.68 g, 5.2 mmol) was added and the reaction was stirred at room temperature for 1 h. The reaction was filtered and the supernatant was isolated and evaporated. The residue was dissolved in 20 mL of diethyl ether and excess CH2N2 (25 mmol of diazomethane) was added and the reaction was stirred at room temperature overnight. The reaction was washed with water (3×20 mL) and the organic layer was isolated and stirred at room temperature while 3 mL of 48% aqueous HBr was slowly added. The reaction was stirred for 1 hour at room temperature then poured over approximately 10 grams of ice and extracted into diethyl ether (3×50 mL). The combined organic washings were dried over MgSO4 and evaporated to furnish (3S)-1-bromo-3-(4-methoxyphenyl)-4-[4-trifluoromethyl)phenyl]butan-2-one that was used directly for the next reaction without further purification.

Step D: (3S)-1-bromo-3-(4-methoxyphenyl)-4-[4-trifluoromethyl)phenyl]butan-2-one (4.95 mmol) was dissolved in DMF (20 mL) and N-acetyl guanidine (1.5 g, 14.9 mmol) was added. The reaction was stirred at room temperature for 48 hrs. Purification by RP HPLC to provide N-(4-{(1S)-1-(4-methoxyphenyl)-2-[4-(trifluoromethyl)phenyl]ethyl}-H-imidazol-2-yl)acetamide (0.16 g, 8%).

Step E: To a solution of N-(4-{(1S)-1-(4-methoxyphenyl)-2-[4-(trifluoromethyl)phenyl]ethyl}-H-imidazol-2-yl)acetamide (0.16 g, 0.39 mmol) in 4 mL 1:1 methanol:H2O was added a drop of concentrated sulfuric acid. The reaction was heated to 80° C. for 12 h. The reaction was cooled and made basic with addition of a saturated solution of sodium bicarbonate. The mixture was extracted with ethyl acetate (3×50 mL). The combined organics were washed with H2O and brine. The combined organic washings were dried over MgSO4 and evaporated and purified by RP HPLC to provide 4-{(1S)-1-(4-methoxylphenyl)-2-[4-(trifluoromethyl)phenyl]ethyl}-1-H-imidazole-2-amine (0.061 g, 43%).

Example 2

(2-amino-4-{(1S)-1-(4-methoxyphenyl)-2-[4-(trifluoromethyl)phenyl]ethyl}-1H-imidazole-5-yl) (phenyl)methanol

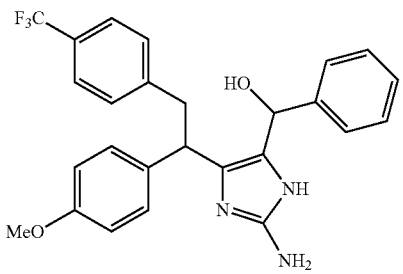

To a solution of 4-{(1S)-1-(4-methoxylphenyl)-2-[4-(trifluoromethyl)phenyl]ethyl}-1H-imidazole-2-amine (0.05 g, 0.14 mmol) in H2O (1 mL) and THF (0.5 mL) was added benzaldehyde (0.018 g, 0.17 mmol) and sodium carbonate (0.01 g, 0.08 mmol). The reaction was stirred at room temperature for 12 h. The reaction was concentrated and purified by RP HPLC to provide (2-amino-4-{(1S)-1-(4-methoxyphenyl)-2-[4-(trifluoromethyl)phenyl]ethyl}-1H-imidazole-5-yl) (phenyl)methanol (0.01 g, 14%).

Example 3

4-(1-benzyl-2,3-dihydro-1H-inden-1-yl)-1-methyl-1H-imidazol-2-amine

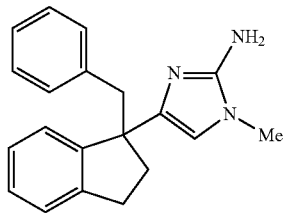 [SMILES: Cn1cc(C2(Cc3ccccc3)CCc3ccccc32)nc1N]

Step A: Thionyl Chloride (0.95 mL, 13.0 mmol) was added to a room temperature solution of indane-1-carboxylic acid dissolved in 20 mL of dichloromethane. The reaction mixture was stirred at room temperature for 35 minutes after which time the volume was reduced by approximately 50% via a rotovap. Then 20 mL of methanol was added and the reaction was stirred at room temperature for 3 hours. Evaporation of the solvent and column chromatography (9/1 hexanes/EtOAc) afforded of methyl indane-1-carboxylate (2.2 g, 100%) as a colorless oil.

Step B: To a −78° C. tetrahydrofuran solution containing methyl indane-1-carboxylate (2.10 g, 11.9 mmol) from Step A, was added a 1M tetrahydrofuran solution of NaHMDS (23.8 mL, 23.8 mmol). The mixture was stirred at −78° C. for 30 minutes. Benzyl bromide (1.49 mL, 12.5 mmol) was added and the reaction was warmed to 0° C. and stirred for 90 minutes. The reaction was quenched with aqueous sodium bicarbonate and then extracted into EtOAc (3×50 mL) and the combined organic washings were dried over MgSO4 and evaporated. The resulting residue was purified by column chromatography (98/2 hexanes/EtOAc) to afford of methyl 1-benzylindane-1-carboxylate (2.5 g, 79%) as a partially pure oil that was taken to the next step.

Step C: Methyl 1-benzylindane-1-carboxylate (2.5 g, 9.4 mmol) from Step B was dissolved in a solution of 23 mL methanol and 23 mL water. Sodium hydroxide (0.940 g, 23.5 mmol) was added to the reaction. The reaction was refluxed and stirred for 90 minutes and then quenched with 100 mL of 1N HCl and extracted with diethyl ether (3×50 mL). The combined organic washings were dried over MgSO4 and evaporated to furnish 1-benzylindane-1-carboxylic acid (2.4 g, 100%) as a yellow oil that was pure enough to be used in the next step.

Step D: To a room temperature solution of 1-benzylindane-1-carboxylic acid (2.4 g, 9.5 mmol) in 50 mL of tetrahydrofuran was added N-methylmorpholine (1 g, 10 mmol). Isobutyl chloroformate (1.4 g, 10 mmol) was added and the reaction was stirred at room temperature for 30 minutes. The reaction was filtered and the supernatant was isolated and evaporated. The residue was dissolved in 50 mL of diethyl ether and excess CH2N2 (25 mmol of diazomethane prepared from a 70 mL diethyl ether solution of Diazald (7.5 g, 35 mmol) and 7.5 g of potassium hydroxide in 12 mL of water) was added and the reaction was stirred at room temperature overnight. The reaction was washed with water (3×20 mL) and the organic layer was isolated and stirred at room temperature while 10 mL of 48% aqueous HBr was slowly added. The reaction was stirred for 1 hour at room temperature then poured over approximately 50 grams of ice and extracted into diethyl ether (3×50 mL). The combined organic washings were dried over MgSO$_4$ and evaporated to furnish 1-(1-benzyl-2,3-dihydro-1H-inden-1-yl)-2-bromoethanone, a red-brown oil sufficiently pure for the next step.

Step E: 1-(1-benzyl-2,3-dihydro-1H-inden-1-yl)-2-bromoethanone (1.0 g, 3.0 mmol) from Step D was dissolved in 15 mL of methanol and a 2M solution of methylamine (2.3 mL, 4.6 mmol) was added to the reaction. The reaction was stirred at room temperature for 1 hour. Then S-ethylisothiourea hydrobromide (2.2 g, 12 mmol) and sodium hydroxide (0.61 g, 15 mmol) were added to the reaction and the mixture was stirred at room temperature for 1 hour. An aliquot was taken from the reaction and purified by reverse-phase chromatography. The isolated fractions containing the desired product were lyophilized to furnish the trifluoroacetic acid salt of 4-(1-benzyl-2,3-dihydro-1H-inden-1-yl)-1-methyl-1H-imidazol-2-amine as a white solid.

Example 4

4-{1-(4-methoxyphenyl)-2-[4-(3-thienyl)phenyl]ethyl}-1-methyl-1H-imidazol-2-amine

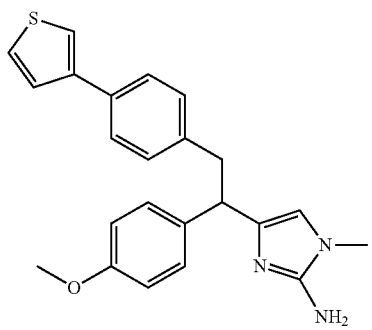

Step A: 3-(4-bromophenyl)-2-(4-methoxyphenyl)propanoic acid (3.0 g, 8.95 mmol), Weinreb amine (1.05 g, 10.7 mmol) were dissolved in DMF (90 ml) and diisopropylethylamine (1.88 ml, 10.7 mmol) was added in one portion. EDC (2.06 g, 10.7 mmol) and HOAt (0.122 g, 0.895 mmol) were added to the resulting solution portionwise. The resulting solution was allowed to stir at 25° C. for 1 hour. After one hour the reaction was diluted with EtOAc, washed with 10% KHSO4, saturated NaHCO3, and LiCl (×3). The organic layer was dried over sodium sulfate and concentrated in vacuo, which afforded 3.2 g of 3-(4-bromophenyl)-N-methoxy-2-(4-methoxyphenyl)-N-methylpropanamide as a colorless oil. 3-(4-bromophenyl)-N-methoxy-2-(4-methoxyphenyl)-N-methylpropanamide (1.0 g, 2.64 mmol) was dissolved in anhydrous THF (26.4 ml) and the resulting solution was cooled to 0° C. MeMgBr (1.32 ml, 3.97 mmol) was added dropwise to the cooled solution, and the resulting solution was allowed to stir for 30 min. at 0° C. The solution was then warmed to 25° C. for one hour, at which point the solution was filtered over a pad of celite and concentrated in vacuo. The resulting crude oil was purified using silica gel chromatography (0-40% EtOAc in hexanes gradient to afford 627 mg of 4-(4-bromophenyl)-3-(4-methoxyphenyl)butan-2-one as a pale yellow oil.

Step B: Diisopropylamine (0.084 g, 0.83 mmol) was dissolved in anhydrous diethyl ether (7.5 mL) under argon atmosphere and cooled to −78° C. BuLi (0.52 mL, 0.83 mmol) was added dropwise to the solution and the resulting solution was allowed to warm to 0° C. for 10 min, then recooled to −78° C. TMS-Cl (freshly distilled over calcium hydride, 0.11 mL, 0.83 mmol) was added dropwise to the solution at −78° C., after addition, the reaction was allowed to stir for an additional 10 min. The solution was then cooled to −90° C., and 4-(4-bromophenyl)-3-(4-methoxyphenyl)butan-2-one (0.25 g, 0.75 mmol) was added dropwise as a solution in anhydrous diethyl ether. After addition was complete, the solution was allowed to stir for an additional 40 min. The reaction was then warmed to 0° C. and phenyltrimethylammonium tribromide (0.31 mg, 0.83 mmol) was slowly added dropwise as a solution in anhydrous THF (4 mL). The resulting solution was allowed to stir at 25° C. for 1 hour. The mixture was diluted with EtOAc and water, washed with NaCl (×3), dried over sodium sulfate and concentrated in vacuo. The crude product was purified using silica gel chromatography (0-30% EtOAc in hexanes gradient) to afford 256 mg of 1-bromo-4-(4-bromophenyl)-3-(4-methoxyphenyl)butan-2-one as a viscous oil.

Step C: 1-bromo-4-(4-bromophenyl)-3-(4-methoxyphenyl)butan-2-one (0.15 g, 0.36 mmol) was dissolved in methanol (1.8 mL) and methylamine (0.36 mL, 0.72 mmol, 2M solution in methanol) was added in one portion and the reaction was allowed to stir at 25° C. for 0.5 hour. S-ethylisothiourea hydrobromide (0.27 mg, 1.46 mmol) and NaOH (0.61 mL, 1.82 mmol, 3M solution in water) were added to the solution and the resulting solution was allowed to stir at 25° C. for 16 hours. The reaction was purified using reverse phase C-18 chromatography (acetontitrile and water system) to afford 140 mg of 4-[2-(4-bromophenyl)-1-(4-methoxyphenyl)ethyl]-1-methyl-1H-imidazol-2-amine as a yellow solid.

Step D: Tris(4,6-dimethyl-3-sulfanatophenyl)phosphine trisodium salt hydrate (0.052 g, 0.078 mmol), Palladium(II) Acetate (0.006 g, 0.026 mmol), and diisopropylamine (0.036 mL, 0.259 mmol) were dissolved in a 80:20 mixture of degassed DMF:H2O (1.0 mL: 260 μL) and allowed to stir for 10 minutes. 4-[2-(4-bromophenyl)-1-(4-methoxyphenyl)ethyl]-1-methyl-1H-imidazol-2-amine (0.05 g, 0.129 mmol), 3-thienylboronic acid (0.05 g, 0.388 mmol) were then added to the solution and the reaction was heated using microwave irradiation for 10 minutes. The reaction was purified using reverse phase C-18 chromatography (acetontitrile and water system) to afford 140 mg of 4-{1-(4-methoxyphenyl)-2-[4-β-thienyl)phenyl]ethyl}-1-methyl-1H-imidazol-2-amine as a yellow oil.

Example 5

4-(4-fluoro-5-methoxy-1-{[6-(trifluoromethyl)pyridin-3-yl]methyl}-2,3-dihydro-1H-inden-1-yl)-1-methyl-1H-imidazol-2-amine

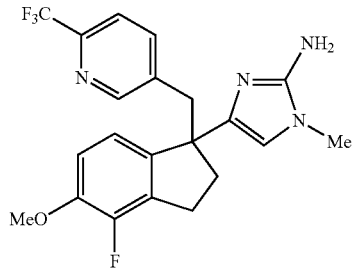 [SMILES: COc1ccc2c(c1F)CCC2(Cc1ccc(C(F)(F)F)nc1)c1cn(C)c(N)n1]

Step A: Sodium bis(hexamethylsilyl) amide (2.1 ml, 2.1 mmol) was added to a solution of 2-(4-fluoro-5-methoxy-2,3-dihydro-1H-inden-1-yl)-2-methoxyethylenol (400 mg, 1.8 mmol) in THF (3.6 ml) at −78° C. 5-Chloromethyl-2(trifluoromethyl)Pyridine (380 mg, 1.9 mmol) was added subsequently (within a minute) to the reaction mixture, which was then allowed to warm to room temperature. To this solution was added 4 mL of 1.0 M Trimethylsilylmethyl lithium in pentane. The reaction mixture was diluted with methanol upon the disappearance of the starting material and left stirring at room temperature for 1 h. The crude reaction mixture was concentrated under reduced pressure and taken in dichloromethane (50 mL) and was then poured into sat. sodium bicarbonate (75 mL) and was extracted with dichloromethane (3×50 mL), dried over magnesium sulfate, filtered, and concentrated under reduced pressure furnished 1-(4-fluoro-5-methoxy-1-{[6-(trifluoromethyl)pyridin-3-yl]methyl}-2,3-dihydro-1H-inden-1-yl)ethanone. Used without further purification.

Step B: 1-(4-fluoro-5-methoxy-1-{[6-(trifluoromethyl)pyridin-3-yl]methyl}-2,3-dihydro-1H-inden-1-yl)ethanone (600 mg, 1.6 mmol) was diluted in THF (3 ml). This solution was cooled to −78° C. and Sodium bis(hexamethylsilyl) amide (1.8 ml, 1.8 mmol) was added. After stirring for 10 min, chloro trimethylsilane (230 μl, 1.8 mmol) was added drop wise at −78° C., after which the reaction was warmed to 0° C., and left stirring for 30 min. To this solution was added Phenyltrimethylammonium tribromide (680 mg, 1.8 mmol) portion wise, and THF (1 mL) was added for solubility purposes. The reaction mixture was allowed to warm to room temp. Aqueous work up, extracted with dichloromethane, dried over magnesium sulfate, filtered, concentrated under reduced pressure furnished 2-bromo-1-(4-fluoro-5-methoxy-1-{[6-(trifluoromethyl)pyridin-3-yl]methyl}-2,3-dihydro-1H-inden-1-yl)ethanone. Used without further purification.

Step C: 2-bromo-1-(4-fluoro-5-methoxy-1-{[6-(trifluoromethyl)pyridin-3-yl]methyl}-2,3-dihydro-1H-inden-1-yl)ethanone (590 mg, 1.3 mmol) was diluted in THF (2.6 ml) and 2.0 M Methylamine (1.3 ml, 2.6 mmol) in THF was added, and the reaction was left stirring at room temp until completion (~20 min) to furnish an amino-ketone intermediate. To the reaction mixture was added one volumetric equivalent of water (1.3 mL). 2-Ethyl-2-thioseudourea hydrobromide (1.2 g, 6.6 mmol) and Sodium hydroxide (160 mg, 3.9 mmol) were added subsequently at room temperature. Upon completion, the crude reaction mixture was poured into water (40 mL) and extracted with ethyl acetate (1×50 mL) then dichloromethane (2×50 mL). Dried over magnesium sulfate, filtered, concentrated under reduced pressure and purified by reverse phase purification to afford 4-(4-fluoro-5-methoxy-1-{[6-(trifluoromethyl)pyridin-3-yl]methyl}-2,3-dihydro-1H-inden-1-yl)-1-methyl-1H-imidazol-2-amine as an off-white solid.

| Ex. No. | Structure | IUPAC Name | Parent Mol. Wgt. | Scheme |
|---|---|---|---|---|
| 6 | 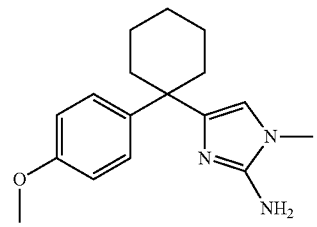 [SMILES: COc1ccc(C2(c3cn(C)c(N)n3)CCCCC2)cc1] | 4-[1-(4-chlorophenyl) cyclopentyl]-1H-imidazol-2-amine | 261.757 | 1 |
| 7 | 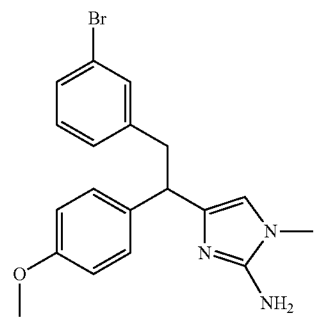 [SMILES: COc1ccc(C(Cc2cccc(Br)c2)c2cn(C)c(N)n2)cc1] | 4-[1-(3-fluoro-4-methyoxy)-2-(2-methoxy-5-nitrophenyl) ethyl]-1H-imidazol-2-amine | 386.386 | 1 |
| 8 | 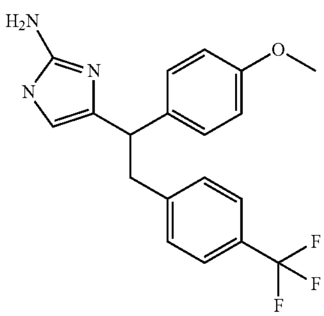 [SMILES: COc1ccc(C(Cc2ccc(C(F)(F)F)cc2)c2c[nH]c(N)n2)cc1] | 4-{1-(4-methoxyphenyl)-2-[4-(trifluoromethyl) phenyl]ethyl}-1H-imidazol-2-amine | 361.37 | 1 |
| 9 | 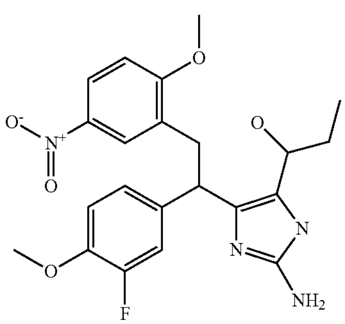 [SMILES: CCC(O)c1[nH]c(N)nc1C(Cc1cc([N+](=O)[O-])ccc1OC)c1ccc(OC)c(F)c1] | 1-{2-amino-4-[1-(3-fluoro-4-methoxyphenyl)-2-(2-methoxy-5-nitrophenyl) ethyl]-1H-imidazol-5-yl}propan-1-ol | 444.467 | 1 |
| 10 | 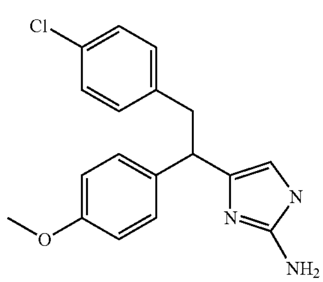 [SMILES: COc1ccc(C(Cc2ccc(Cl)cc2)c2c[nH]c(N)n2)cc1] | 4-[2-(4-chlorophenyl)-1-(4-methoxyphenyl)ethyl]-1H-imidazol-2-amine | 327.817 | 1 |

-continued

| Ex. No. | Structure | IUPAC Name | Parent Mol. Wgt. | Scheme |
|---|---|---|---|---|
| 11 | 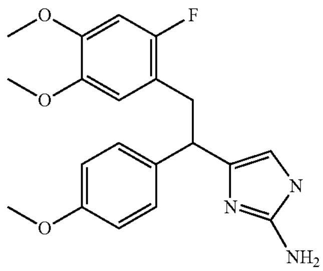 [SMILES: COc1ccc(C(Cc2cc(OC)c(OC)cc2F)c2c[nH]c(N)n2)cc1] | 4-[2-(2-fluoro-4,5-dimethoxyphenyl)-1-(4-methoxyphenyl)ethyl]-1H-imidazol-2-amine | 371.415 | 1 |
| 12 | 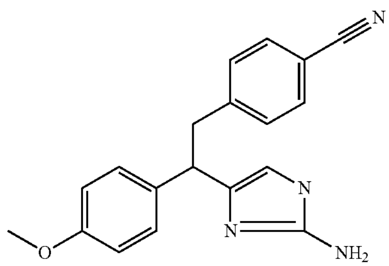 [SMILES: COc1ccc(C(Cc2ccc(C#N)cc2)c2c[nH]c(N)n2)cc1] | 4-[2-(2-amino-1H-imidazol-4-yl)-2-(4-methoxyphenyl)ethyl]benzonitrile | 318.382 | 1 |
| 13 | 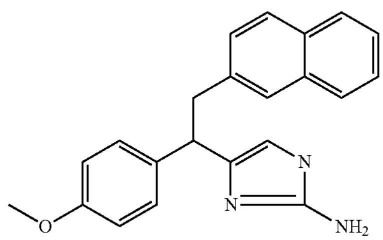 [SMILES: COc1ccc(C(Cc2ccc3ccccc3c2)c2c[nH]c(N)n2)cc1] | 4-1-(4-methoxyphenyl)-2-(2-naphthyl)ethyl]-1H-imidazol-2-amine | 384.432 | 1 |
| 14 | 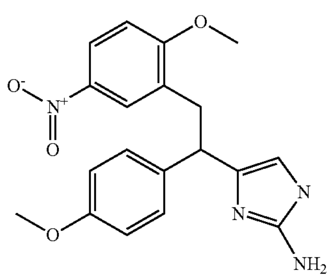 [SMILES: COc1ccc(C(Cc2cc([N+](=O)[O-])ccc2OC)c2c[nH]c(N)n2)cc1] | 4-[2-(2-methoxy-5-nitrophenyl)-1-(4-methoxyphenyl)ethyl]-1H-imidazol-2-amine | 368.396 | 1 |
| 15 | 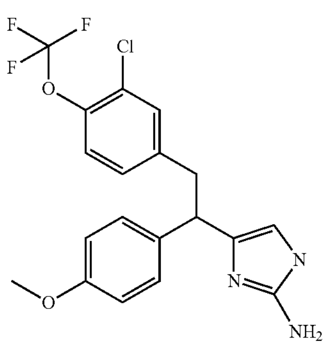 [SMILES: COc1ccc(C(Cc2ccc(OC(F)(F)F)c(Cl)c2)c2c[nH]c(N)n2)cc1] | 4-[2-[3-chloro-4-(trifluoromethoxy)phenyl]-1-(4-methoxyphenyl)ethyl]-1H-imidazol-2-amine | 411.814 | 1 |

| Ex. No. | Structure | IUPAC Name | Parent Mol. Wgt. | Scheme |
|---|---|---|---|---|
| 16 | 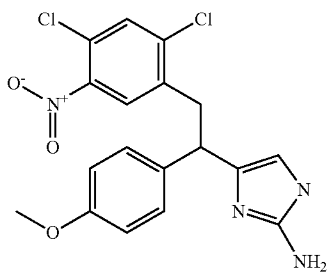 [SMILES: COc1ccc(C(Cc2cc([N+](=O)[O-])c(Cl)cc2Cl)c2c[nH]c(N)n2)cc1] | 4-[2-(2,4-dichloro-5-nitrophenyl)-1-(4-methoxyphenyl)ethyl]-1H-imidazol-2-amine | 407.259 | 1 |
| 17 | 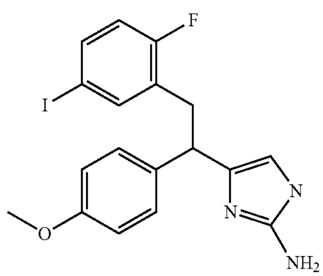 [SMILES: COc1ccc(C(Cc2cc(I)ccc2F)c2c[nH]c(N)n2)cc1] | 4-[2-(2-fluoro-5-iodophenyl)-1-(4-methoxyphenyl)ethyl]-1H-imidazol-2-amine | 437.258 | 1 |
| 18 | 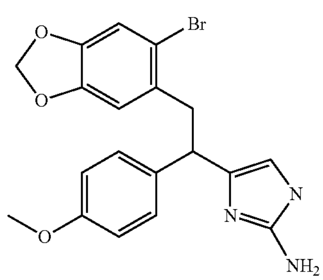 [SMILES: COc1ccc(C(Cc2cc3c(cc2Br)OCO3)c2c[nH]c(N)n2)cc1] | 4-[2-(6-bromo-1,3-benzodioxol-5-yl)-1-(4-methoxyphenyl)ethyl]-1H-imidazol-2-amine | 416.278 | 1 |
| 19 | 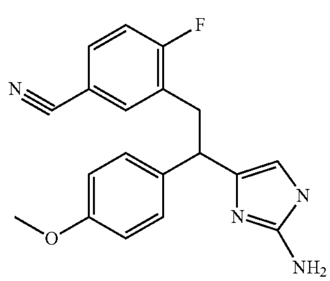 [SMILES: COc1ccc(C(Cc2cc(C#N)ccc2F)c2c[nH]c(N)n2)cc1] | 3-[2-(2-amino-1H-imidazol-4-yl)-2-(4-methoxyphenyl)ethyl]-4-fluorobenzonitrile | 336.372 | 1 |
| 20 | 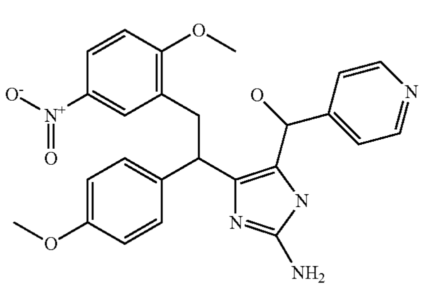 [SMILES: COc1ccc(C(Cc2cc([N+](=O)[O-])ccc2OC)c2nc(N)[nH]c2C(O)c2ccncc2)cc1] | {2-amino-4-[2-(2-methoxy-5-nitrophenyl)-1-(4-methoxyphenyl)ethyl]-1H-imidazol-5-yl}(pyridin-4-yl)methanol | 475.509 | 1 |

-continued

| Ex. No. | Structure | IUPAC Name | Parent Mol. Wgt. | Scheme |
|---|---|---|---|---|
| 21 | 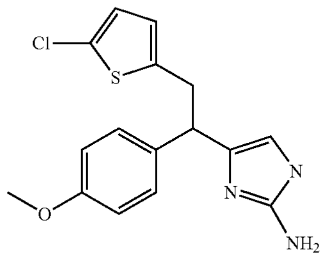 [SMILES: COc1ccc(C(Cc2ccc(Cl)s2)c2c[nH]c(N)n2)cc1] | 4-[2-(5-chloro-2-thienyl)-1-(4-methoxyphenyl)ethyl]-1H-imidazol-2-amine | 333.842 | 1 |
| 22 | 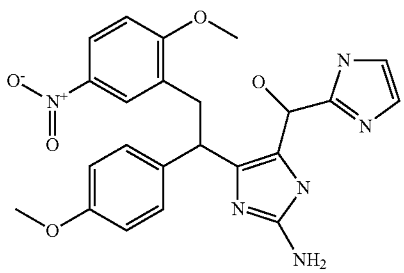 [SMILES: COc1ccc(C(Cc2cc([N+](=O)[O-])ccc2OC)c2nc(N)[nH]c2C(O)c2ncc[nH]2)cc1] | {2-amino-4-[2-(2-methoxy-5-nitrophenyl)-1-(4-methoxyphenyl)ethyl]-1H-imidazol-5-yl}(1H-imidazol-2-yl)methanol | 464.485 | 1 |
| 23 | 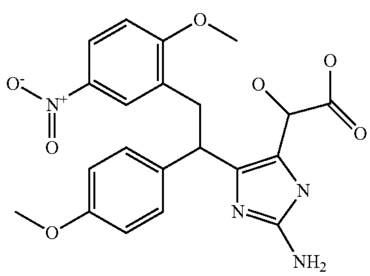 [SMILES: COc1ccc(C(Cc2cc([N+](=O)[O-])ccc2OC)c2nc(N)[nH]c2C(O)C(=O)O)cc1] | {2-amino-4-[2-(2-methoxy-5-nitrophenyl)-1-(4-methoxyphenyl)ethyl]-1H-imidazol-5-yl}(hydroxy)acetic acid | 442.432 | 1 |
| 24 | 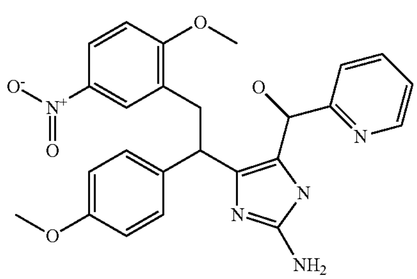 [SMILES: COc1ccc(C(Cc2cc([N+](=O)[O-])ccc2OC)c2nc(N)[nH]c2C(O)c2ccccn2)cc1] | {2-amino-4-[2-(2-methoxy-5-nitrophenyl)-1-(4-methoxyphenyl)ethyl]-1H-imidazol-5-yl}(pyridin-2-yl)methanol | 475.509 | 1 |
| 25 | 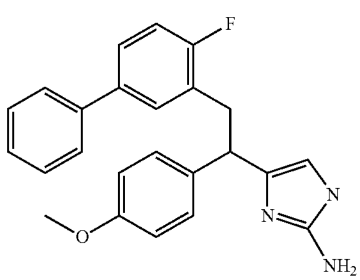 [SMILES: COc1ccc(C(Cc2cc(-c3ccccc3)ccc2F)c2c[nH]c(N)n2)cc1] | 4-[2-(4-fluorobiphenyl-3-yl)-1-(4-methoxyphenyl)ethyl]-1H-imidazol-2-amine | 387.461 | 1 |

| Ex. No. | Structure | IUPAC Name | Parent Mol. Wgt. | Scheme |
|---|---|---|---|---|
| 26 | 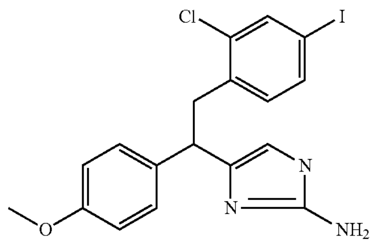 [SMILES: COc1ccc(C(Cc2ccc(I)cc2Cl)c2c[nH]c(N)n2)cc1] | 4-[2-(2-chloro-4-iodophenyl)-1-(4-methoxyphenyl)ethyl]-1H-imidazol-2-amine | 453.713 | 1 |
| 27 | 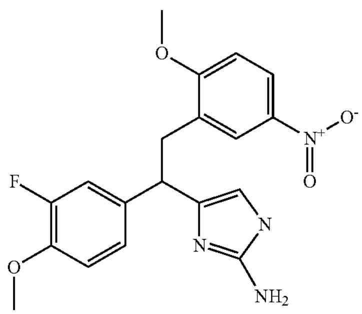 [SMILES: COc1ccc(C(Cc2cc([N+](=O)[O-])ccc2OC)c2c[nH]c(N)n2)cc1F] | 4-[1-(3-fluoro-4-methoxyphenyl)-2-(2-methoxy-5-nitrophenyl)ethyl]-1H-imidazol-2-amine | 386.386 | 1 |
| 28 | 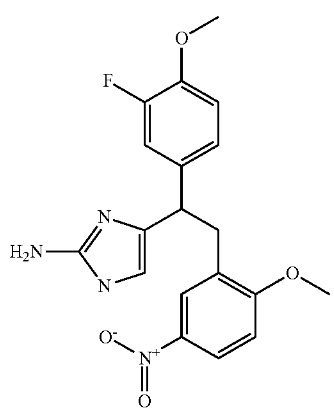 [SMILES: COc1ccc(C(Cc2cc([N+](=O)[O-])ccc2OC)c2c[nH]c(N)n2)cc1F] | 4-[1-(3-fluoro-4-methoxyphenyl)-2-(2-methoxy-5-nitrophenyl)ethyl]-1H-imidazol-2-amine | 386.386 | 1 |
| 29 | 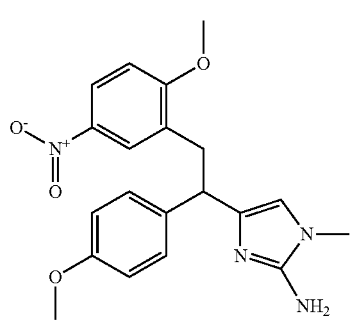 [SMILES: COc1ccc(C(Cc2cc([N+](=O)[O-])ccc2OC)c2cn(C)c(N)n2)cc1] | 4-[2-(2-methoxy-5-nitrophenyl)-1-(4-methoxyphenyl)ethyl]-1-methyl-1H-imidazol-2-amine | 382.423 | 2 |

| Ex. No. | Structure | IUPAC Name | Parent Mol. Wgt. | Scheme |
|---|---|---|---|---|
| 30 | 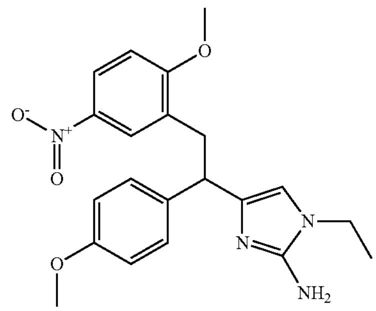 [SMILES: CCn1cc(C(Cc2cc([N+](=O)[O-])ccc2OC)c2ccc(OC)cc2)nc1N] | 1-ethyl-4-[2-(2-methoxy-5-nitrophenyl)-1-(4-methoxyphenyl)ethyl]-1H-imidazol-2-amine | 396.45 | 2, 3 |
| 31 | 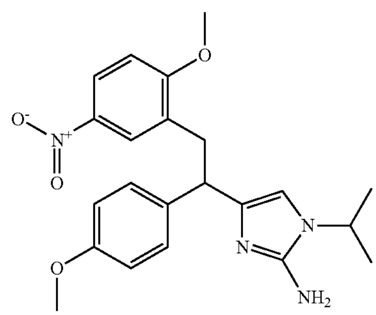 [SMILES: COc1ccc(C(Cc2cc([N+](=O)[O-])ccc2OC)c2cn(C(C)C)c(N)n2)cc1] | 1-isopropyl-4-[2-(2-methoxy-5-nitrophenyl)-1-(4-methoxyphenyl)ethyl]-1H-imidazol-2-amine | 410.477 | 2, 3 |
| 32 | 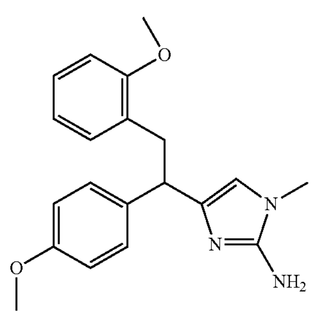 [SMILES: COc1ccc(C(Cc2ccccc2OC)c2cn(C)c(N)n2)cc1] | 4-[2-(2-methoxyphenyl)-1-(4-methoxyphenyl)ethyl]-1-methyl-1H-imidazol-2-amine | 337.425 | 2, 3 |
| 33 | 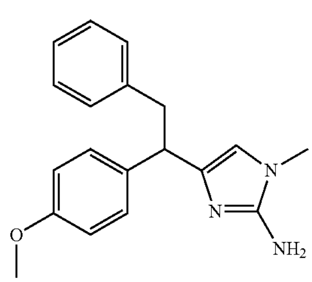 [SMILES: COc1ccc(C(Cc2ccccc2)c2cn(C)c(N)n2)cc1] | 4-[1-(4-methoxyphenyl)-2-phenylethyl]-1-methyl-1H-imidazol-2-amine | 307.399 | 2, 3 |

-continued

| Ex. No. | Structure | IUPAC Name | Parent Mol. Wgt. | Scheme |
|---|---|---|---|---|
| 34 | 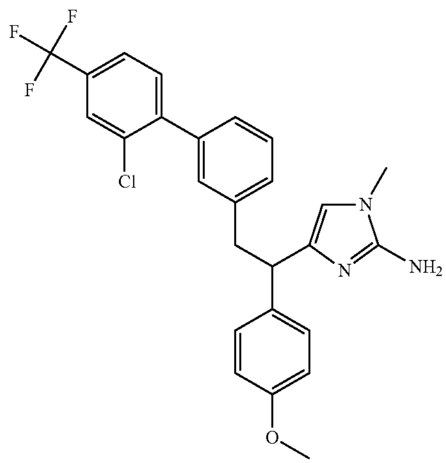 [SMILES: COc1ccc(C(Cc2cccc(-c3ccc(C(F)(F)F)cc3Cl)c2)c2cn(C)c(N)n2)cc1] | 4-[2-[2'-chloro-4'-(trifluoromethyl)biphenyl-3-yl]-1-(4-methoxyphenyl)ethyl]-1-methyl-1H-imidazol-2-amine | 485.941 | 2, 3, 5 |
| 35 | 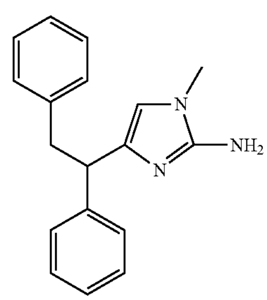 [SMILES: Cn1cc(C(Cc2ccccc2)c2ccccc2)nc1N] | 4-(1,2-diphenylethyl)-1-methyl-1H-imidazol-2-amine | 277.372 | 2, 3 |
| 36 | 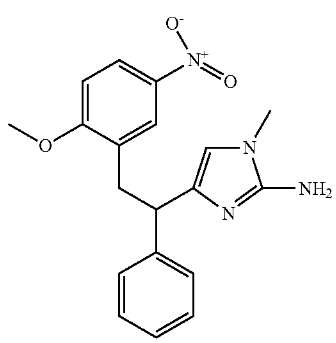 [SMILES: COc1ccc([N+](=O)[O-])cc1CC(c1ccccc1)c1cn(C)c(N)n1] | 4-[1-(4-methoxyphenyl)-2-(3-nitrophenyl)ethyl]-1-methyl-1H-imidazol-2-amine | 352.396 | 2, 3 |
| 37 | 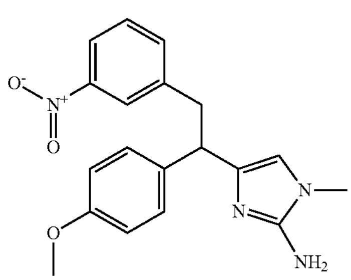 [SMILES: COc1ccc(C(Cc2cccc([N+](=O)[O-])c2)c2cn(C)c(N)n2)cc1] | 4-[1-(4-methoxyphenyl)-2-(3-nitrophenyl)ethyl]-1-methyl-1H-imidazol-2-amine | 352.396 | 2, 3 |

-continued

| Ex. No. | Structure | IUPAC Name | Parent Mol. Wgt. | Scheme |
|---|---|---|---|---|
| 38 | 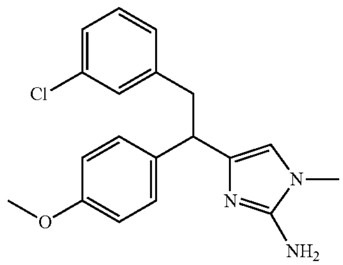 | 4-[2-(3-chlorophenyl)-1-(4-methoxyphenyl)ethyl]-1-methyl-1H-imidazol-2-amine | 341.844 | 2, 3 |
| 39 | 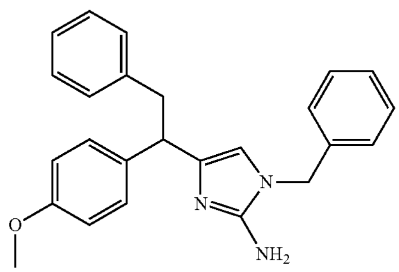 [SMILES: COc1ccc(C(Cc2ccccc2)c2cn(Cc3ccccc3)c(N)n2)cc1] | 1-benzyl-4-[1-(4-methoxyphenyl)-2-phenylethyl]-1H-imidazol-2-amine | 383.497 | 2, 3 |
| 40 | 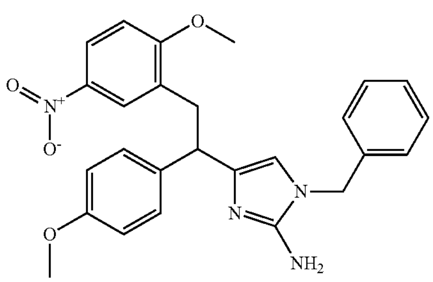 [SMILES: COc1ccc(C(Cc2cc([N+](=O)[O-])ccc2OC)c2cn(Cc3ccccc3)c(N)n2)cc1] | 1-benzyl-4-[2-(2-methoxy-5-nitrophenyl)-1-(4-methoxyphenyl)ethyl]-1H-imidazol-2-amine | 458.522 | 2, 3 |
| 41 | 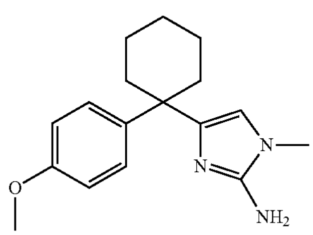 [SMILES: COc1ccc(C2(c3cn(C)c(N)n3)CCCCC2)cc1] | 4-[1-(4-methoxyphenyl)cyclohexyl]-1-methyl-1H-imidazol-2-amine | 285.392 | 2, 3 |
| 42 | 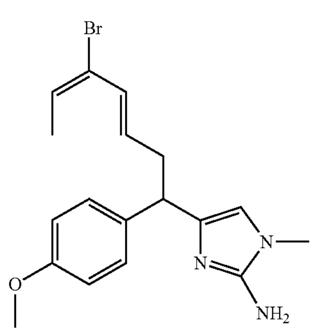 [SMILES: C/C=C(Br)\C=C\CC(c1ccc(OC)cc1)c1cn(C)c(N)n1] | 4-[2-(3-bromophenyl)-1-(4-methoxyphenyl)ethyl]-1-methyl-1H-imidazol-2-amine | 386.295 | 2, 3 |

-continued

| Ex. No. | Structure | IUPAC Name | Parent Mol. Wgt. | Scheme |
|---|---|---|---|---|
| 43 | 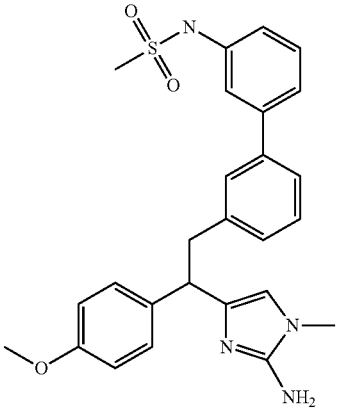 | N-{3'-[2-(2-amino-1-methyl-1H-imidazol-4-yl)-2-(4-methoxyphenyl)ethyl]biphenyl-3-yl}methanesulfonamide | 476.602 | 2, 3, 5 |
| 44 | 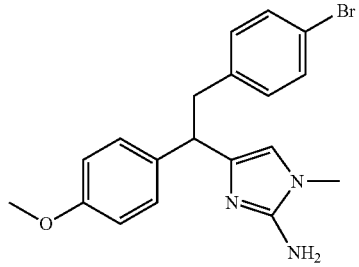 [SMILES: COc1ccc(C(Cc2ccc(Br)cc2)c2cn(C)c(N)n2)cc1] | 4-[2-(4-bromophenyl)-1-(4-methoxyphenyl)ethyl]-1-methyl-1H-imidazol-2-amine | 386.295 | 2, 3 |
| 45 | 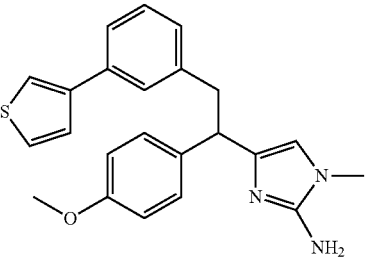 [SMILES: COc1ccc(C(Cc2cccc(-c3ccsc3)c2)c2cn(C)c(N)n2)cc1] | 4-{1-(4-methoxyphenyl)-2-[3-(3-thienyl)phenyl]ethyl}-1-methyl-1H-imidazol-2-amine | 389.523 | 2, 3, 5 |
| 46 | 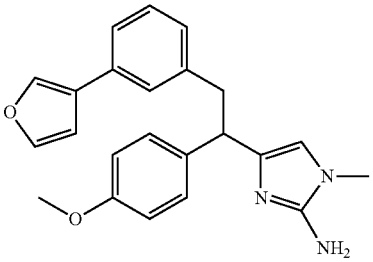 [SMILES: COc1ccc(C(Cc2cccc(-c3ccoc3)c2)c2cn(C)c(N)n2)cc1] | 4-[2-[3-(3-furyl)phenyl]-1-(4-methoxyphenyl)ethyl]-1-methyl-1H-imidazol-2-amine | 373.459 | 2, 3, 5 |
| 47 | 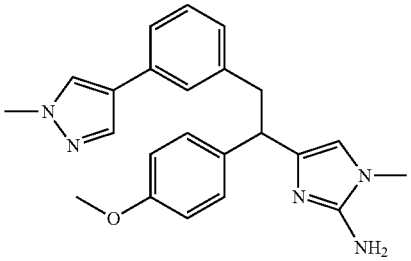 | 4-{1-(4-methoxyphenyl)-2-[3-(1-methyl-1H-pyrazol-4-yl)phenyl]ethyl}-1-methyl-1H-imidazol-2-amine | 387.489 | 2, 3, 5 |

-continued

| Ex. No. | Structure | IUPAC Name | Parent Mol. Wgt. | Scheme |
|---|---|---|---|---|
| 48 | 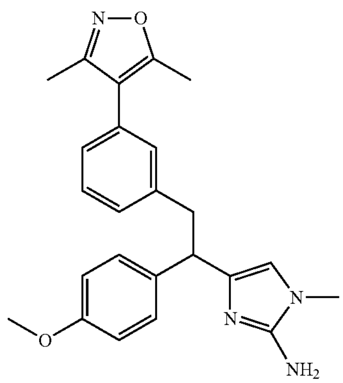 | 4-[2-[3-(3,5-dimethylisoxazol-4-yl)phenyl]-1-(4-methoxyphenyl)ethyl]-1-methyl-1H-imidazol-2-amine | 402.5 | 2, 3, 5 |
| 49 | 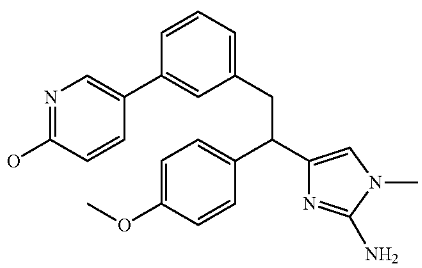 [SMILES: COc1ccc(C(Cc2cccc(-c3ccc(O)nc3)c2)c2cn(C)c(N)n2)cc1] | 5-{3-[2-(2-amino-1-methyl-1H-imidazol-4-yl)-2-(4-methoxyphenyl)ethyl]phenyl}pyridin-2-ol | 400.484 | 2, 3, 5 |
| 50 | 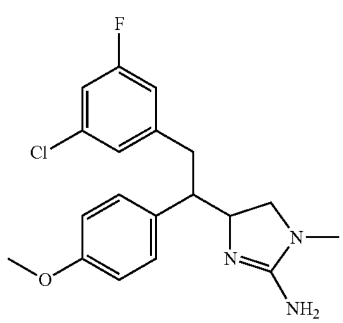 | 4-[2-(3-chloro-5-fluorophenyl)-1-(4-methoxyphenyl)ethyl]-1-methyl-1H-imidazol-2-amine | 359.834 | 2, 3 |
| 51 | 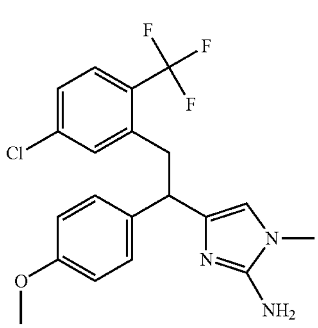 [SMILES: COc1ccc(C(Cc2cc(Cl)ccc2C(F)(F)F)c2cn(C)c(N)n2)cc1] | 4-[2-(5-chloro-2-trifluorophenyl)phenyl]-1-(4-methoxyphenyl)ethyl]-1-methyl-1H-imidazol-2-amine | 409.842 | 2, 3 |

| Ex. No. | Structure | IUPAC Name | Parent Mol. Wgt. | Scheme |
|---|---|---|---|---|
| 52 | 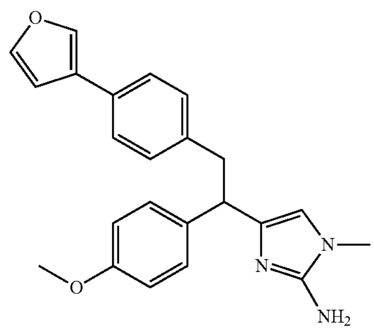 [SMILES: COc1ccc(C(Cc2ccc(-c3ccoc3)cc2)c2cn(C)c(N)n2)cc1] | 4-[2-[4-(3-furyl)phenyl]-1-(4-methoxyphenyl)ethyl]-1-methyl-1H-imidazol-2-amine | 373.459 | 2, 3, 5 |
| 53 | 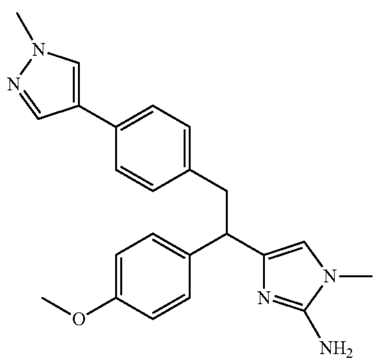 [SMILES: COc1ccc(C(Cc2ccc(-c3cnn(C)c3)cc2)c2cn(C)c(N)n2)cc1] | 4-{1-(4-methoxyphenyl)-2-[4-(1-methyl-1H-pyrazol-4-yl)phenyl] ethyl}-1-methyl-1H-imidazol-2-amine | 387.489 | 2, 3, 5 |
| 54 | 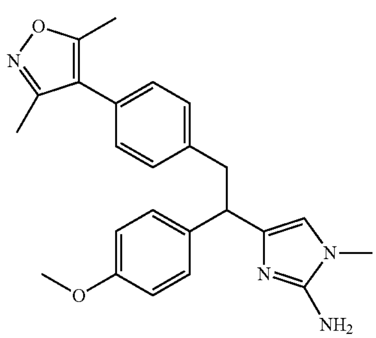 [SMILES: COc1ccc(C(Cc2ccc(-c3c(C)noc3C)cc2)c2cn(C)c(N)n2)cc1] | 4-[2-[4-(3,5-dimethylisoxazol-4-yl)phenyl]-1-(4-methoxyphenyl)ethyl]-1-methyl-1H-imidazol-2-amine | 402.5 | 2, 3, 5 |
| 55 | 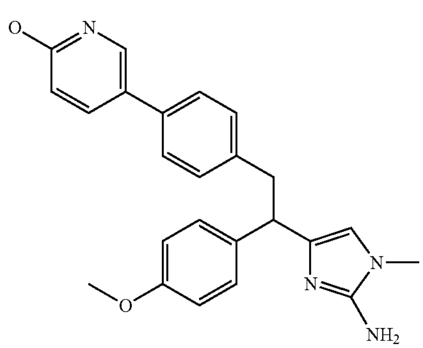 [SMILES: COc1ccc(C(Cc2ccc(-c3ccc(O)nc3)cc2)c2cn(C)c(N)n2)cc1] | 5-{4-[2-(2-amino-1-methyl-1H-imidazol-4-yl)-2-(4-methoxyphenyl)ethyl]phenyl}pyridin-2-ol | 400.484 | 2, 3, 5 |

| Ex. No. | Structure | IUPAC Name | Parent Mol. Wgt. | Scheme |
|---|---|---|---|---|
| 56 | 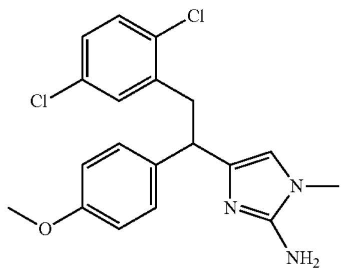 | 4-[2-(2,5-dichlorophenyl)-1-(4-methoxyphenyl)ethyl]-1-methyl-1H-imidazol-2-amine | 376.289 | 2, 3 |
| 57 | 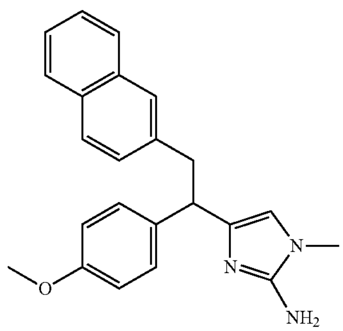 | 4-[1-(4-methoxyphenyl)-2-(2-naphthyl)ethyl]-1-methyl-1H-imidazol-2-amine | 357.459 | 2, 3 |
| 58 | 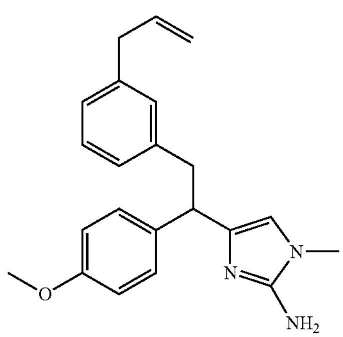 | 4-[2-(3-allylphenyl)-1-(4-methoxyphenyl)ethyl]-1-methyl-1H-imidazol-2-amine | 347.464 | 2, 3 |
| 59 | 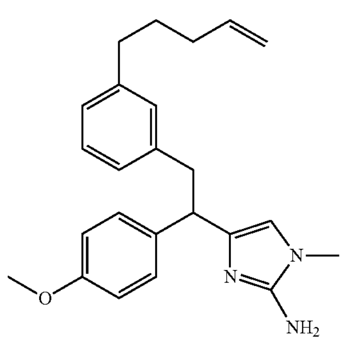 | 4-[1-(4-methoxyphenyl)-2-(3-pent-4-en-1-ylphenyl)ethyl]-1-methyl-1H-imidazol-2-amine | 375.518 | 2, 3 |

-continued

| Ex. No. | Structure | IUPAC Name | Parent Mol. Wgt. | Scheme |
|---|---|---|---|---|
| 60 | 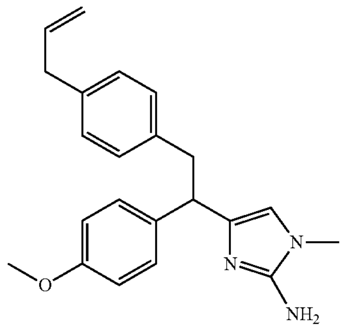 | 4-[2-(4-allylphenyl)-1-(4-methoxyphenyl)ethyl]-1-methyl-1H-imidazol-2-amine | 347.464 | 2, 3 |
| 61 | 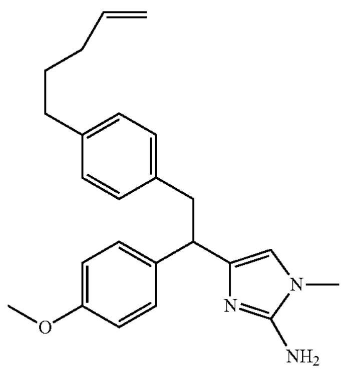 | 4-[1-(4-methoxyphenyl)-2-(4-pent-4-en-1-ylphenyl)ethyl]-1-methyl-1H-imidazol-2-amine | 375.518 | 2, 3 |
| 62 | 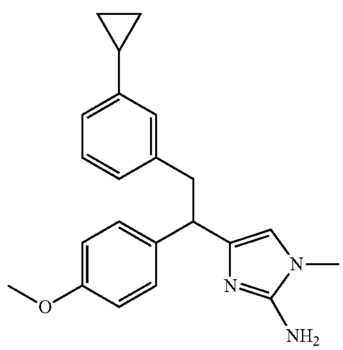 | 4-[2-(3-cyclopropylphenyl)-1-(4-methoxyphenyl)ethyl]-1-methyl-1H-imidazol-2-amine | 347.464 | 2, 3 |
| 63 | 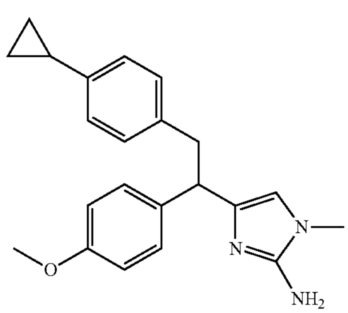 [SMILES: COc1ccc(C(Cc2ccc(C3CC3)cc2)c2cn(C)c(N)n2)cc1] | 4-[2-(4-cyclopropylphenyl)-1-(4-methoxyphenyl)ethyl]-1-methyl-1H-imidazol-2-amine | 347.464 | 2, 3 |

| Ex. No. | Structure | IUPAC Name | Parent Mol. Wgt. | Scheme |
|---|---|---|---|---|
| 64 | 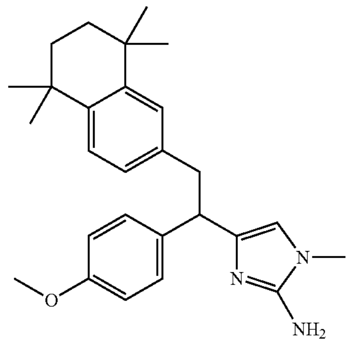 | 4-[1-(4-methoxyphenyl)-2-(5,5,8,8-tetramethyl-5,6,7,8-tetrahydronaphthalen-2-yl)ethyl]-1-methyl-1H-imidazol-2-amine | 417.599 | 2, 3 |
| 65 | 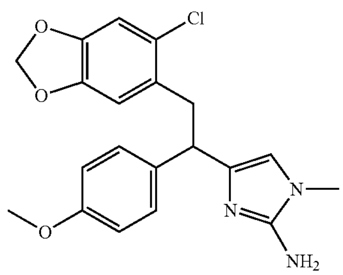 | 4-[2-(6-chloro-1,3-benzodioxol-5-yl)-1-(4-methoxyphenyl)ethyl]-1-methyl-1H-imidazol-2-amine | 385.854 | 2, 3 |
| 66 | 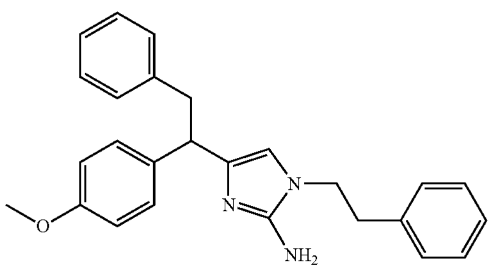 [SMILES: COc1ccc(C(Cc2ccccc2)c2cn(CCc3ccccc3)c(N)n2)cc1] | 4-[1-(4-methoxyphenyl)-2-phenylethyl]-1-(2-phenylethyl)-1H-imidazol-2-amine | 397.525 | 2, 3 |
| 67 | 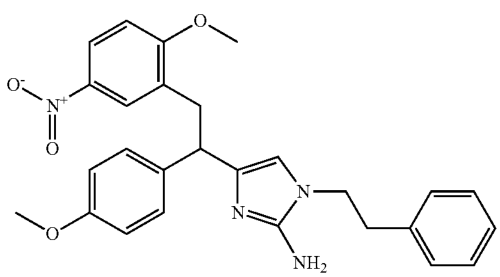 [SMILES: COc1ccc(C(Cc2cc([N+](=O)[O-])ccc2OC)c2cn(CCc3ccccc3)c(N)n2)cc1] | 4-[2-(2-methoxy-5-nitrophenyl)-1-(4-methoxyphenyl)ethyl]-1-(2-phenylethyl)-1H-imidazol-2-amine | 472.549 | 2, 3 |
| 68 | 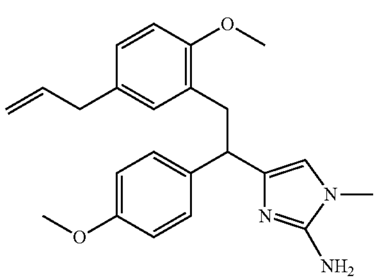 [SMILES: C=CCc1ccc(OC)c(CC(c2ccc(OC)cc2)c2cn(C)c(N)n2)c1] | 4-[2-(5-allyl-2-methoxyphenyl)-1-(4-methoxyphenyl)ethyl]-1-methyl-1H-imidazol-2-amine | 377.491 | 2, 3 |

| Ex. No. | Structure | IUPAC Name | Parent Mol. Wgt. | Scheme |
|---|---|---|---|---|
| 69 | 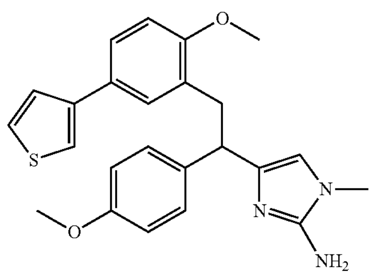 [SMILES: COc1ccc(C(Cc2cc(-c3ccsc3)ccc2OC)c2cn(C)c(N)n2)cc1] | 4-{1-(4-methoxyphenyl)-2-[2-methoxy-5-(3-thienyl)phenyl]ethyl}-1-methyl-1H-imidazol-2-amine | 419.55 | 2, 3, 5 |
| 70 | 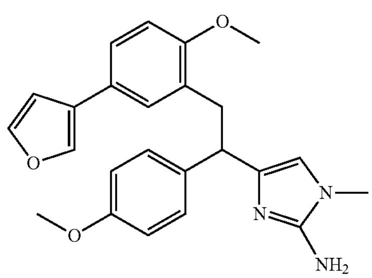 | 4-[2-[5-(3-furyl)-2-methoxyphenyl]-1-(4-methoxyphenyl)ethyl]-1-methyl-1H-imidazol-2-amine | 403.485 | 2, 3, 5 |
| 71 | 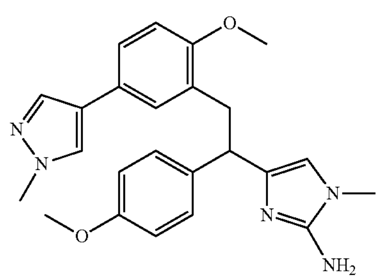 [SMILES: COc1ccc(C(Cc2cc(-c3cnn(C)c3)ccc2OC)c2cn(C)c(N)n2)cc1] | 4-[2-[2-methoxy-5-(1-methyl-1H-pyrazol-4-yl)phenyl]-1-(4-methoxyphenyl)ethyl]-1-methyl-1H-imidazol-2-amine | 417.515 | 2, 3, 5 |
| 72 | 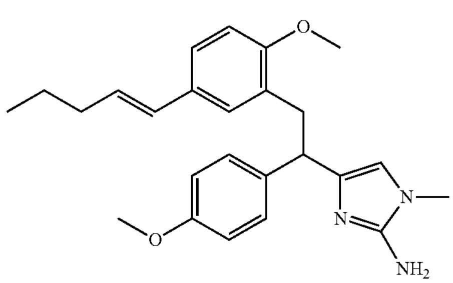 [SMILES: CCC/C=C/c1ccc(OC)c(CC(c2ccc(OC)cc2)c2cn(C)c(N)n2)c1] | 4-[2-{2-methoxy-5-[(1E)-pent-1-en-1-yl]phenyl}-1-(4-methoxyphenyl)ethyl]-1-methyl-1H-imidazol-2-amine | 405.545 | 2, 3, 5 |
| 73 | 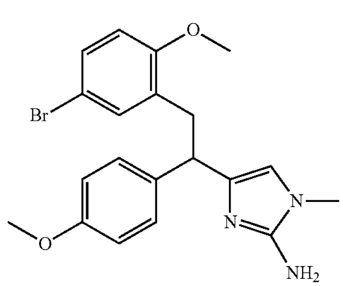 | 4-[2-(5-bromo-2-methoxyphenyl)-1-(4-methoxyphenyl)ethyl]-1-methyl-1H-imidazol-2-amine | 416.321 | 2, 3 |

| Ex. No. | Structure | IUPAC Name | Parent Mol. Wgt. | Scheme |
|---|---|---|---|---|
| 74 | 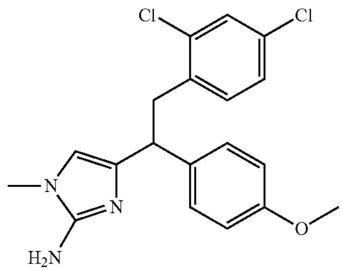 | 4-[2-(2,4-dichlorophenyl)-1-(4-methoxyphenyl)ethyl]-1-methyl-1H-imidazol-2-amine | 376.289 | 2, 3 |
| 75 | 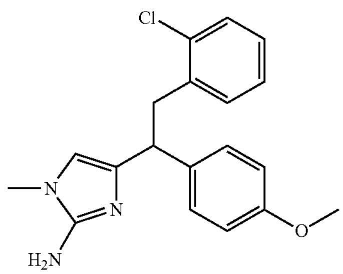 | 4-[2-(2-chlorophenyl)-1-(4-methoxyphenyl)ethyl]-1-methyl-1H-imidazol-2-amine | 341.844 | 2, 3 |
| 76 | 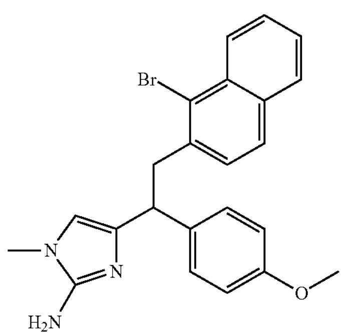 | 4-[2-(1-bromo-2-naphthyl)-1-(4-methoxyphenyl)ethyl]-1-methyl-1H-imidazol-2-amine | 436.355 | 2, 3 |
| 77 | 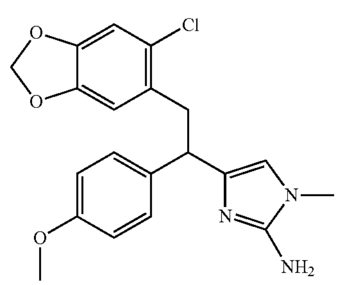 [SMILES: COc1ccc(C(Cc2cc3c(cc2Cl)OCO3)c2cn(C)c(N)n2)cc1] | 4-[2-(6-chloro-1,3-benzodioxol-5-yl)-1-(4-methoxyphenyl)ethyl]-1-methyl-1H-imidazol-2-amine | 385.854 | 2, 3 |
| 78 | 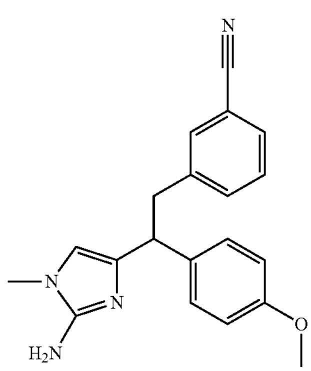 | 3-[2-(2-amino-1-methyl-1H-imidazol-4-yl)-2-(4-methoxyphenyl)ethyl]benzonitrile | 332.409 | 2, 3 |

-continued

| Ex. No. | Structure | IUPAC Name | Parent Mol. Wgt. | Scheme |
|---|---|---|---|---|
| 79 | 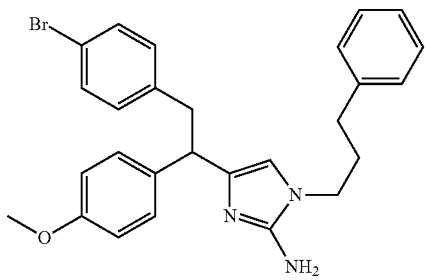 [SMILES: COc1ccc(C(Cc2ccc(Br)cc2)c2cn(CCCc3ccccc3)c(N)n2)cc1] | 4-[2-(4-bromophenyl)-1-(4-methoxyphenyl)ethyl]-1-(3-phenylpropyl)-1H-imidazol-2-amine | 490.448 | 2, 3 |
| 80 | 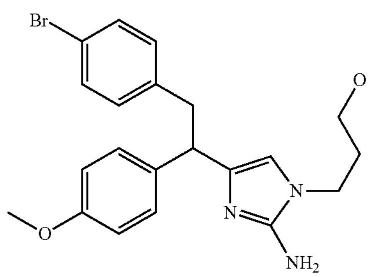 [SMILES: COc1ccc(C(Cc2ccc(Br)cc2)c2cn(CCCO)c(N)n2)cc1] | 3-{2-amino-4-[2-(4-bromophenyl)-1-(4-methoxyphenyl)ethyl]-1H-imidazol-1-yl}propan-1-ol | 430.348 | 2, 3 |
| 81 | 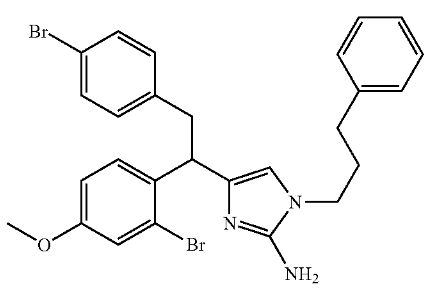 [SMILES: COc1ccc(C(Cc2ccc(Br)cc2)c2cn(CCCc3ccccc3)c(N)n2)c(Br)c1] | 4-[1-(2-bromo-4-methoxyphenyl)-2-(4-bromophenyl)ethyl]-1-(3-phenylpropyl)-1H-imidazol-2-amine | 569.344 | 2, 3 |
| 82 | 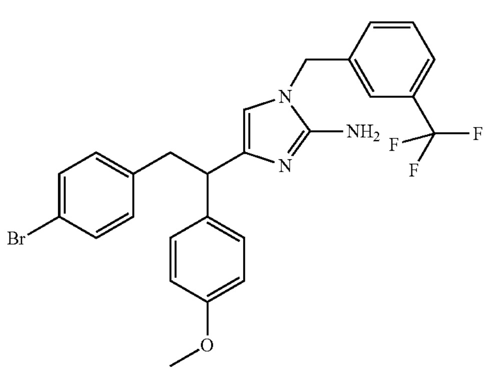 [SMILES: COc1ccc(C(Cc2ccc(Br)cc2)c2cn(Cc3cccc(C(F)(F)F)c3)c(N)n2)cc1] | 4-[2-(4-bromophenyl)-1-(4-methoxyphenyl)ethyl]-1-[3-(trifluoromethyl)benzyl]-1H-imidazol-2-amine | 530.392 | 2, 3 |

-continued

| Ex. No. | Structure | IUPAC Name | Parent Mol. Wgt. | Scheme |
|---|---|---|---|---|
| 83 | 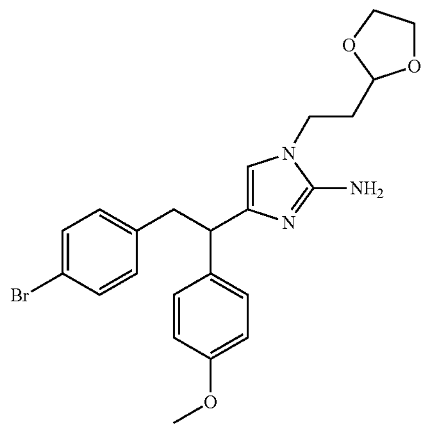 [SMILES: COc1ccc(C(Cc2ccc(Br)cc2)c2cn(CCC3OCCO3)c(N)n2)cc1] | 4-[2-(4-bromophenyl)-1-(4-methoxyphenyl)ethyl]-1-[2-(1,3-dioxolan-2-yl)ethyl]-1H-imidazol-2-amine | 472.386 | 2, 3 |
| 84 | 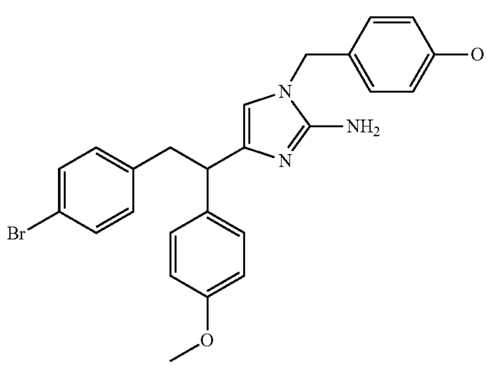 [SMILES: COc1ccc(C(Cc2ccc(Br)cc2)c2cn(Cc3ccc(O)cc3)c(N)n2)cc1] | 4-({2-amino-4-[2-(4-bromophenyl)-1-(4-methoxyphenyl)ethyl]-1H-imidazol-1-yl}methyl)phenol | 478.393 | 2, 3 |
| 85 | 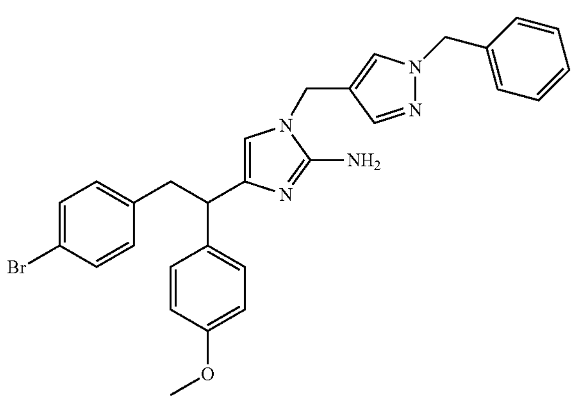 [SMILES: COc1ccc(C(Cc2ccc(Br)cc2)c2cn(Cc3cnn(Cc4ccccc4)c3)c(N)n2)cc1] | 1-[(1-benzyl-1H-pyrazol-4-yl)methyl]-4-[2-(4-bromophenyl)-1-(4-methoxyphenyl)ethyl]-1H-imidazol-2-amine | 542.483 | 2, 3 |
| 86 | 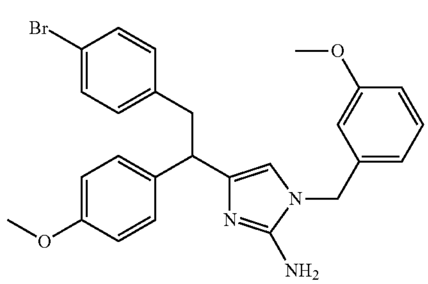 [SMILES: COc1ccc(C(Cc2ccc(Br)cc2)c2cn(Cc3cccc(OC)c3)c(N)n2)cc1] | 4-[2-(4-bromophenyl)-1-(4-methoxyphenyl)ethyl]-1-(3-methoxybenzyl)-1H-imidazol-2-amine | 492.42 | 2, 3 |

| Ex. No. | Structure | IUPAC Name | Parent Mol. Wgt. | Scheme |
|---|---|---|---|---|
| 87 | 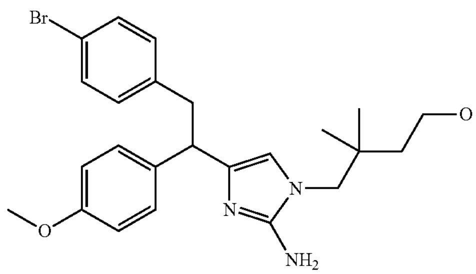 [SMILES: COc1ccc(C(Cc2ccc(Br)cc2)c2cn(CC(C)(C)CCO)c(N)n2)cc1] | 4-{2-amino-4-[2-(4-bromophenyl)-1-(4-methoxyphenyl)ethyl]-1H-imidazol-1-yl}-3,3-dimethylbutan-1-ol | 472.43 | 2, 3 |
| 88 | 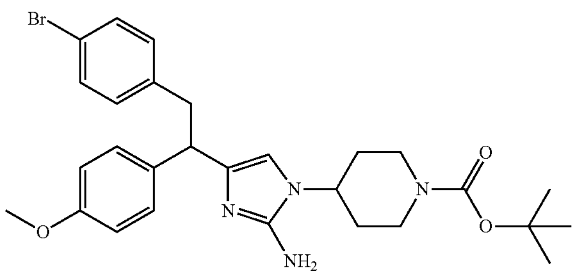 [SMILES: COc1ccc(C(Cc2ccc(Br)cc2)c2cn(C3CCN(C(=O)OC(C)(C)C)CC3)c(N)n2)cc1] | tert-butyl 4-{2-amino-4-[2-(4-bromophenyl)-1-(4-methoxyphenyl)ethyl]-1H-imidazol-1-yl}piperidine-1-carboxylate | 555.52 | 2, 3 |
| 89 | 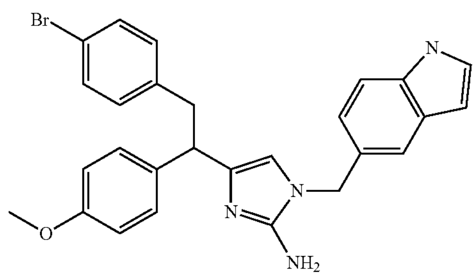 [SMILES: COc1ccc(C(Cc2ccc(Br)cc2)c2cn(Cc3ccc4[nH]ccc4c3)c(N)n2)cc1] | 4-[2-(4-bromophenyl)-1-(4-methoxyphenyl)ethyl]-1-(1H-indol-5-ylmethyl)-1H-imidazol-2-amine | 501.43 | 2, 3 |
| 90 | 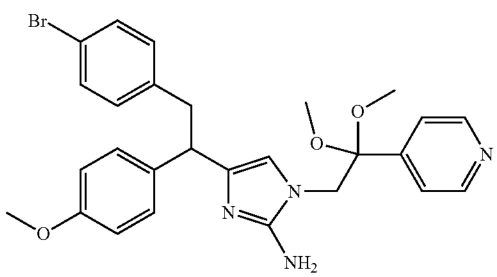 [SMILES: COc1ccc(C(Cc2ccc(Br)cc2)c2cn(CC(OC)(OC)c3ccncc3)c(N)n2)cc1] | 4-[2-(4-bromophenyl)-1-(4-methoxyphenyl)ethyl]-1-(2,2-dimethoxy-2-pyridin-4-ylethyl)-1H-imidazol-2-amine | 537.461 | 2, 3 |
| 91 | 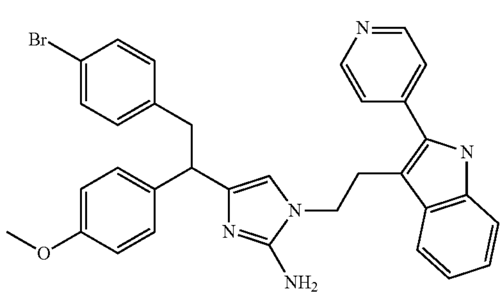 [SMILES: COc1ccc(C(Cc2ccc(Br)cc2)c2cn(CCc3c(-c4ccncc4)[nH]c4ccccc34)c(N)n2)cc1] | 4-[2-(4-bromophenyl)-1-(4-methoxyphenyl)ethyl]-1-[2-(2-pyridin-4-yl-1H-indol-3-yl)ethyl]-1H-imidazol-2-amine | 592.544 | 2, 3 |

| Ex. No. | Structure | IUPAC Name | Parent Mol. Wgt. | Scheme |
|---|---|---|---|---|
| 92 | 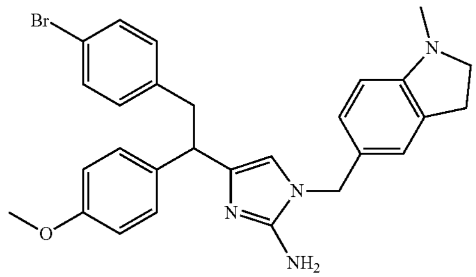 [SMILES: COc1ccc(C(Cc2ccc(Br)cc2)c2cn(Cc3ccc4c(c3)CCN4C)c(N)n2)cc1] | 4-[2-(4-bromophenyl)-1-(4-methoxyphenyl)ethyl]-1-[(1-methyl-2,3-dihydro-1H-indol-5-yl)methyl]-1H-imidazol-2-amine | 517.474 | 2, 3 |
| 93 | 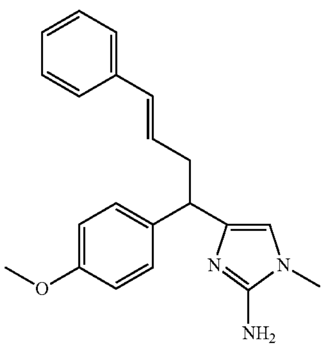 | 4-[(3E)-1-(4-methoxyphenyl)-4-phenylbut-3-en-1-yl]-1-methyl-1H-imidazol-2-amine | 333.437 | 2, 3 |
| 94 | 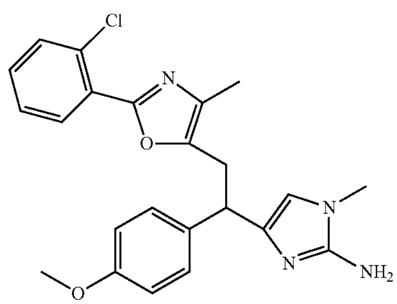 [SMILES: COc1ccc(C(Cc2oc(-c3ccccc3Cl)nc2C)c2cn(C)c(N)n2)cc1] | 4-[2-[2-(2-chlorophenyl)-4-methyl-1,3-oxazol-5-yl]-1-(4-methoxyphenyl)ethyl]-1-methyl-1H-imidazol-2-amine | 422.918 | 2, 3, 5 |
| 95 | 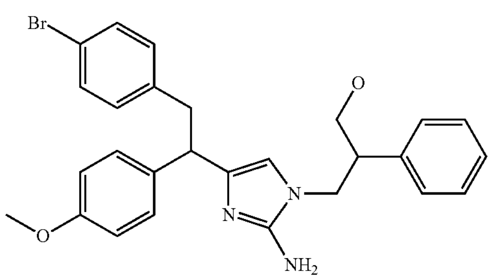 [SMILES: COc1ccc(C(Cc2ccc(Br)cc2)c2cn(CC(CO)c3ccccc3)c(N)n2)cc1] | 3-{2-amino-4-[2-(4-bromophenyl)-1-(4-methoxyphenyl)ethyl]-1H-imidazol-1-yl}-2-phenylpropan-1-ol | 506.447 | 2, 3 |
| 96 | 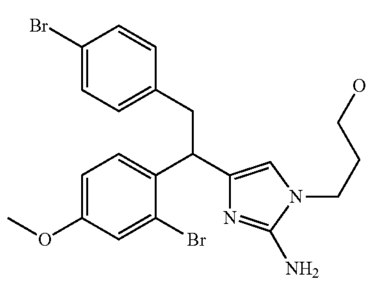 [SMILES: COc1ccc(C(Cc2ccc(Br)cc2)c2cn(CCCO)c(N)n2)c(Br)c1] | 3-{2-amino-4-[1-(2-bromo-4-methoxyphenyl)-2-(4-bromophenyl)ethyl]-1H-imidazol-1-yl}propan-1-ol | 509.244 | 2, 3 |

-continued

| Ex. No. | Structure | IUPAC Name | Parent Mol. Wgt. | Scheme |
|---|---|---|---|---|
| 97 | 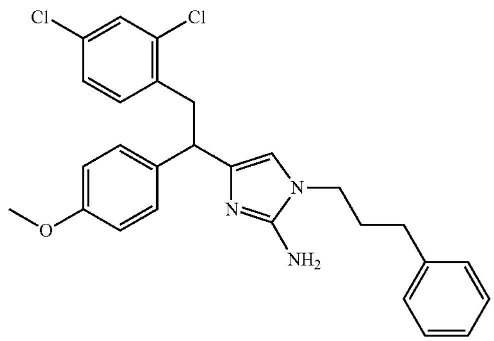 [SMILES: COc1ccc(C(Cc2ccc(Cl)cc2Cl)c2cn(CCCc3ccccc3)c(N)n2)cc1] | 4-[2-(2,4-dichlorophenyl)-1-(4-methoxyphenyl)ethyl]-1-(3-phenylpropyl)-1H-imidazol-2-amine | 480.442 | 2, 3 |
| 98 | 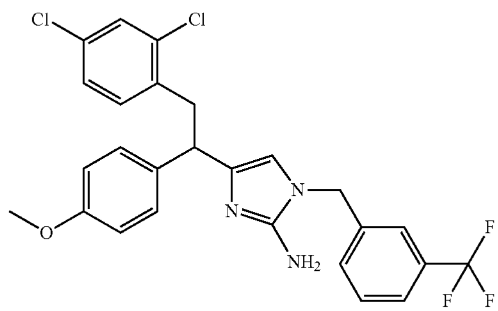 [SMILES: COc1ccc(C(Cc2ccc(Cl)cc2Cl)c2cn(Cc3cccc(C(F)(F)F)c3)c(N)n2)cc1] | 4-[2-(2,4-dichlorophenyl)-1-(4-methoxyphenyl)ethyl]-1-[3-(trifluoromethyl)benzyl]-1H-imidazol-2-amine | 520.386 | 2, 3 |
| 99 | 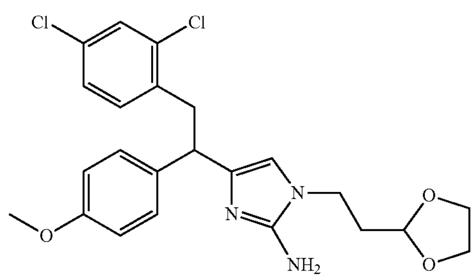 [SMILES: COc1ccc(C(Cc2ccc(Cl)cc2Cl)c2cn(CCC3OCCO3)c(N)n2)cc1] | 4-[2-(2,4-dichlorophenyl)-1-(4-methoxyphenyl)ethyl]-1-[2-(1,3-dioxolan-2-yl)ethyl]-1H-imidazol-2-amine | 462.38 | 2, 3 |
| 100 | 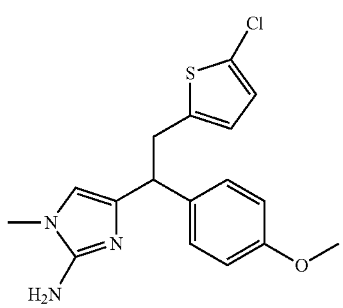 | 4-[2-(5-chloro-2-thienyl)-1-(4-methoxyphenyl)-ethyl]-1-methyl-1H-imidazol-2-amine | 347.87 | 2, 3 |
| 101 | 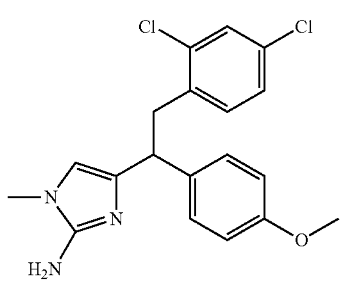 | 4-[2-(2,4-dichlorophenyl)-1-(4-methoxyphenyl)ethyl]-1-methyl-1H-imidazol-2-amine | 376.289 | 2, 3 |

| Ex. No. | Structure | IUPAC Name | Parent Mol. Wgt. | Scheme |
|---|---|---|---|---|
| 102 | 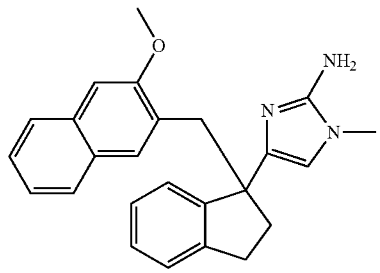 [SMILES: COc1cc2ccccc2cc1CC1(c2cn(C)c(N)n2)CCc2ccccc21] | 4-{1-[(3-methoxy-2-naphthyl)methyl]-2,3-dihydro-1H-inden-1-yl}-1-methyl-1H-imidazol-2-amine | 348.497 | 2, 4 |
| 103 | 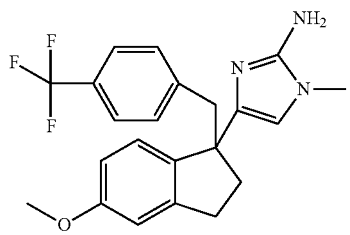 [SMILES: COc1ccc2c(c1)CCC2(Cc1ccc(C(F)(F)F)cc1)c1cn(C)c(N)n1] | 4-(5-methoxy-1-[4-(trifluoromethyl)benyzl]-2,3-dihydro-1H-inden-1-yl}-1-methyl-1H-imidazol-2-amine | 401.435 | 2, 4 |
| 104 | 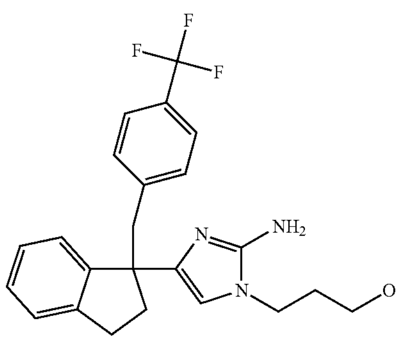 [SMILES: Nc1nc(C2(Cc3ccc(C(F)(F)F)cc3)CCc3ccccc32)cn1CCCO] | 3-(2-amino-4-{1-[4-(trifluoromethyl)benzyl]-2,3-dihydro-1H-inden-1-yl}-1H-imidazol-1-yl)propan-1-ol | 415.462 | 2, 4 |
| 105 | 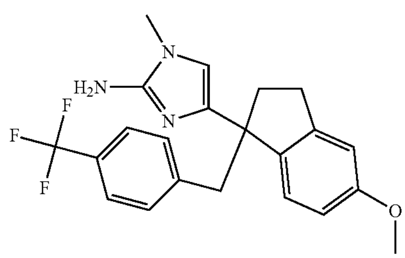 [SMILES: COc1ccc2c(c1)CCC2(Cc1ccc(C(F)(F)F)cc1)c1cn(C)c(N)n1] | 4-{5-methoxy-1-[4-(trifluoromethyl)benzyl]-2,3-dihydro-1H-inden-1-yl}-1-methyl-1H-imidazol-2-amine | 401.435 | 2, 4 |
| 106 | 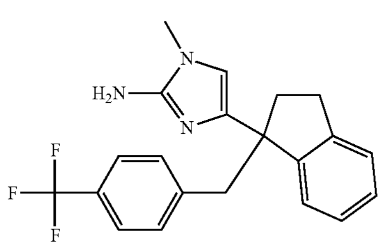 [SMILES: Cn1cc(C2(Cc3ccc(C(F)(F)F)cc3)CCc3ccccc32)nc1N] | 1-methyl-4-{1-[4-(trifluoromethyl)benzyl]-2,3-dihydro-1H-inden-1-yl}-1H-imidazol-2-amine | 371.409 | 2, 4 |

| Ex. No. | Structure | IUPAC Name | Parent Mol. Wgt. | Scheme |
|---|---|---|---|---|
| 107 | 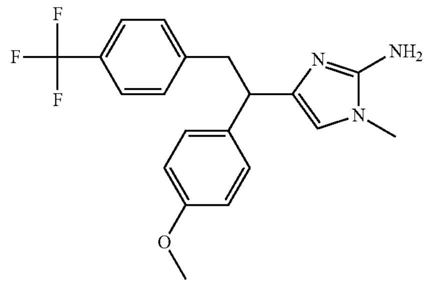 [SMILES: COc1ccc(C(Cc2ccc(C(F)(F)F)cc2)c2cn(C)c(N)n2)cc1] | 4-{1-(4-methoxyphenyl)-2-[4-(trifluoromethyl)phenyl]ethyl}-1-methyl-1H-imidazol-2-amine | 375.397 | 2, 3 |
| 108 | 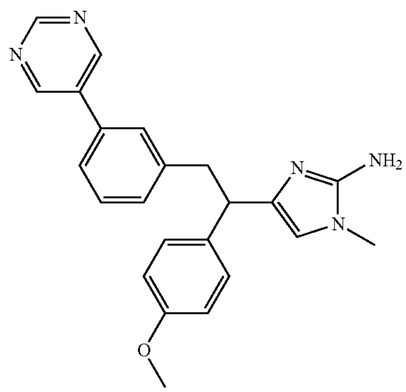 [SMILES: COc1ccc(C(Cc2cccc(-c3cncnc3)c2)c2cn(C)c(N)n2)cc1] | 4-[1-(4-methoxyphenyl)-2-(3-pyrimidin-5-ylphenyl)ethyl]-1-methyl-1H-imidazol-2-amine | 385.473 | 2, 3, 5 |
| 109 | 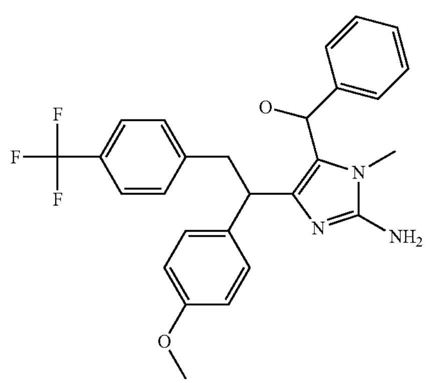 [SMILES: COc1ccc(C(Cc2ccc(C(F)(F)F)cc2)c2nc(N)n(C)c2C(O)c2ccccc2)cc1] | (2-amino-4-{1-(4-methoxyphenyl)-2-[4-(trifluoromethyl)phenyl]ethyl}-1-methyl-1H-imidazol-5-yl)(phenyl) methanol | 482.522 | 2, 3 |
| 110 | 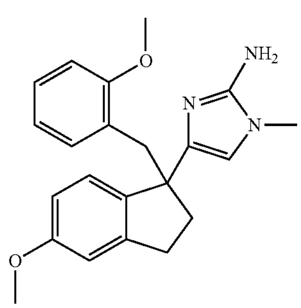 [SMILES: COc1ccc2c(c1)CCC2(Cc1ccccc1OC)c1cn(C)c(N)n1] | 4-[5-methoxy-1-(2-methoxybenzyl)-2,3-dihydro-1H-inden-1-yl]-1-methyl-1H-imidazol-2-amine | 363.463 | 2, 4 |

-continued

| Ex. No. | Structure | IUPAC Name | Parent Mol. Wgt. | Scheme |
|---|---|---|---|---|
| 111 | 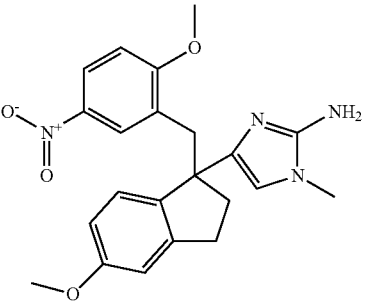 [SMILES: COc1ccc2c(c1)CCC2(Cc1cc([N+](=O)[O-])ccc1OC)c1cn(C)c(N)n1] | 4-[5-methoxy-1-(2-methoxy-5-nitrobenzyl)-2,3-dihydro-1H-inden-1-yl]-1-methyl-1H-imidazol-2-amine | 408.461 | 2, 4 |
| 112 | 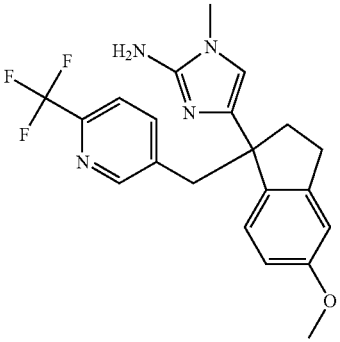 [SMILES: COc1ccc2c(c1)CCC2(Cc1ccc(C(F)(F)F)nc1)c1cn(C)c(N)n1] | 4-(5-methoxy-1-{[6-(trifluoromethyl)pyridin-3-yl]methyl}-2,3-dihydro 1H-inden-1-yl)-1-methyl-1H-imidazol-2-amine | 402.423 | 2, 4 |
| 113 | 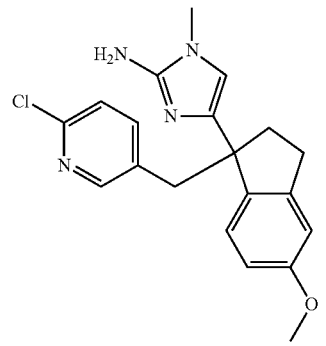 [SMILES: COc1ccc2c(c1)CCC2(Cc1ccc(Cl)nc1)c1cn(C)c(N)n1] | 4-{1-[(6-chloropyridin-3-yl)methyl]-5-methoxy-2,3-dihydro-1H-inden-1-yl}-1-methyl-1H-imidazol-2-amine | 368.87 | 2, 4 |
| 114 | 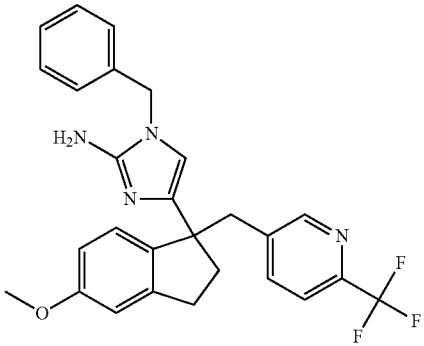 [SMILES: COc1ccc2c(c1)CCC2(Cc1ccc(C(F)(F)F)nc1)c1cn(Cc2ccccc2)c(N)n1] | 1-benzyl-4-(5-methoxy-1-{[6-(trifluoromethyl)pyridin-3-yl]methyl}-2,3-dihydro-1H-inden-1-yl)-1H-imidazol-2-amine | 478.522 | 2, 4 |

-continued

| Ex. No. | Structure | IUPAC Name | Parent Mol. Wgt. | Scheme |
|---|---|---|---|---|
| 115 | 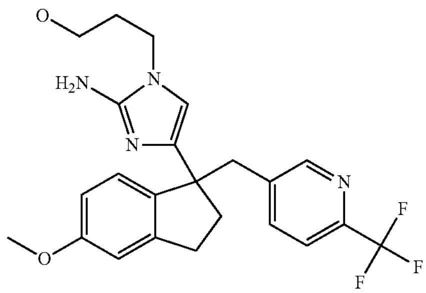 [SMILES: COc1ccc2c(c1)CCC2(Cc1ccc(C(F)(F)F)nc1)c1cn(CCCO)c(N)n1] | 3-[2-amino-4-(5-methoxy-1-{[6-(trifluoromethyl)pyridin-3-yl]methyl}-2,3-dihydro-1H-inden-1-yl)-1H-imidazol-1-yl]propan-1-ol | 446.476 | 2, 4 |
| 116 | 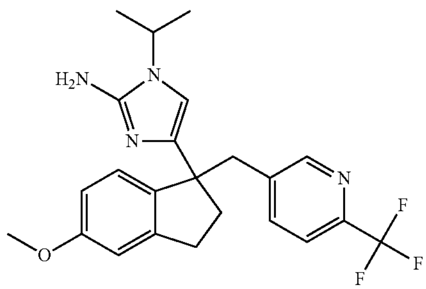 [SMILES: COc1ccc2c(c1)CCC2(Cc1ccc(C(F)(F)F)nc1)c1cn(C(C)C)c(N)n1] | 1-isopropyl-4-(5-methoxy-1-{[6-(trifluoromethyl)pyridin-3-yl]methyl}-2,3-dihydro-1H-inden-1-yl)-1H-imidazol-2-amine | 430.477 | 2, 4 |
| 117 | 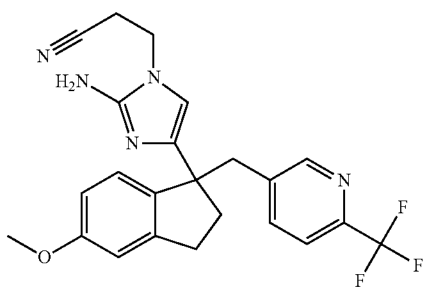 [SMILES: COc1ccc2c(c1)CCC2(Cc1ccc(C(F)(F)F)nc1)c1cn(CCC#N)c(N)n1] | 3-[2-amino-4-(5-methoxy-1-{[6-(trifluoromethyl)pyridin-3-yl]methyl}-2,3-dihydro-1H-inden-1-yl)-1H-imidazol-1-yl]propanenitrile | 441.46 | 2, 4 |
| 118 | 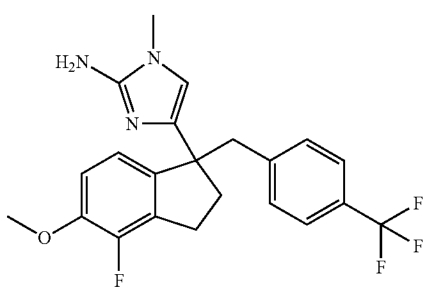 [SMILES: COc1ccc2c(c1F)CCC2(Cc1ccc(C(F)(F)F)cc1)c1cn(C)c(N)n1] | 4-{4-fluoro-5-methoxy-1-[4-(trifluoromethyl)benzyl]-2,3-dihydro-1H-inden-1-yl}-1-methyl-1H-imidazol-2-amine | 419.426 | 2, 4 |
| 119 | 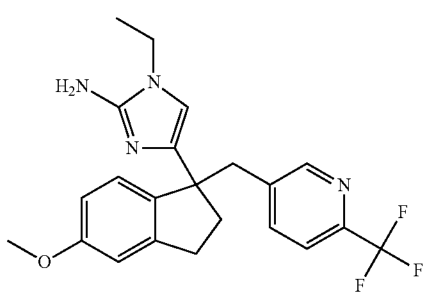 [SMILES: CCn1cc(C2(Cc3ccc(C(F)(F)F)nc3)CCc3cc(OC)ccc32)nc1N] | 1-ethyl-4-(5-methoxy-1-{[6-(4-trifluoromethyl)pyridin-3-yl]methyl}-2,3-dihydro-1H-inden-1-yl)-1H-imidazol-2-amine | 426.45 | 2, 4 |

| Ex. No. | Structure | IUPAC Name | Parent Mol. Wgt. | Scheme |
| --- | --- | --- | --- | --- |
| 120 | 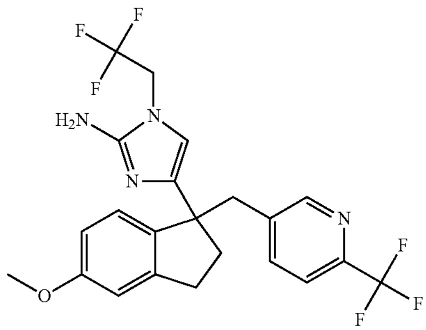 [SMILES: COc1ccc2c(c1)CCC2(Cc1ccc(C(F)(F)F)nc1)c1cn(CC(F)(F)F)c(N)n1] | 4-(5-methoxy-1-{[6-(trifluoromethyl)pyridin-3-yl]methyl}-2,3-dihydro-1H-inden-1-yl)-1-(2,2,2-trifluoroethyl)-1H-imidazol-2-amine | 470.421 | 2, 4 |
| 121 | 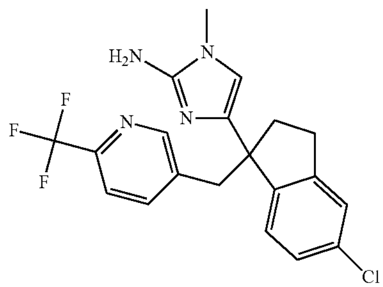 [SMILES: Cn1cc(C2(Cc3ccc(C(F)(F)F)nc3)CCc3cc(Cl)ccc32)nc1N] | 4-(5-chloro-1-{[6-(trifluoromethyl)pyridin-3-yl]methyl}-2,3-dihydro-1H-inden-1-yl)-1-methyl-1H-imidazol-2-amine | 406.841 | 2, 4 |
| 122 | 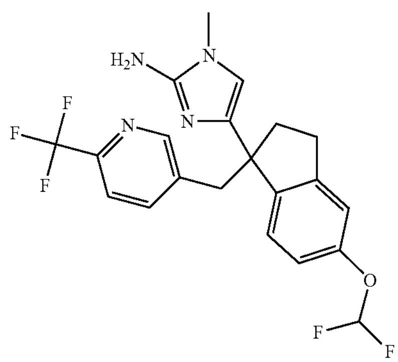 [SMILES: Cn1cc(C2(Cc3ccc(C(F)(F)F)nc3)CCc3cc(OC(F)F)ccc32)nc1N] | 4-(5-(difluoromethoxy)-1-{[6-(trifluoromethyl)pyridin-3-yl]methyl}-2,3-dihydro-1H-inden-1-yl)-1-methyl-1H-imidazol-2-amine | 438.404 | 2, 4 |
| 123 | 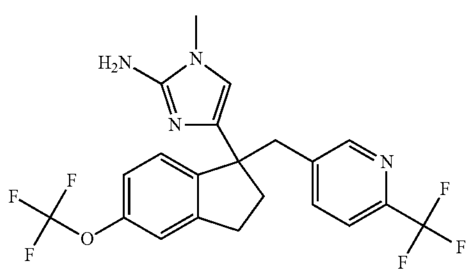 [SMILES: Cn1cc(C2(Cc3ccc(C(F)(F)F)nc3)CCc3cc(OC(F)(F)F)ccc32)nc1N] | 1-methyl-4-(5-(trifluoromethoxy)-1-{[6-(trifluoromethyl)pyridin-3-yl]methyl}-2,3-dihydro-1H-inden-1-yl)-1H-imidazol-2-amine | 456.394 | 2, 4 |

The following abbreviations are used throughout the text:

| | |
| --- | --- |
| Me: | methyl |
| Et: | ethyl |
| Bu: | butyl |
| t-Bu: | tert-butyl |
| i-Bu: | iso-butyl |
| Pr: | propyl |
| i-Pr: | iso-propyl |
| Ar: | aryl |

-continued

| | |
| --- | --- |
| Ph: | phenyl |
| Bn: | benzyl |
| Cbz: | carbobenzyloxy |
| LAH: | lithium aluminum hydride |
| DCM: | dichloromethane |
| DCE: | dichloroethane |
| DMA: | dimethylacetamide |
| BOP: | benzotriazolyl-N-oxy-tris(dimethylamino)phosphonium hexafluorophosphate |
| Boc: | tert butyloxycarbonyl |

-continued

| TFA: | trifluoro acetic acid |
| --- | --- |
| THF: | tetrahydrofuran |
| Ac: | acetyl |
| aq: | aqueous |
| rt: | room temperature |
| h: | hours |
| min: | minutes |

The invention claimed is:

1. A compound of formula (I)

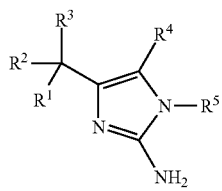

wherein:

$R^1$ is phenyl which is optionally substituted with one or more groups independent selected from the group consisting of:
 (a) halo,
 (b) —$NO_2$,
 (c) —CN,
 (d) —$C_{1-6}$ alkyl, and
 (h) —O—$C_{1-6}$ alkyl;

$R^2$ is hydrogen;

$R^3$ is
 —$(CH_2)_n$-phenyl,
 wherein said phenyl moiety is optionally independently substituted with one or more groups independently selected from the group consisting of:
 (a) halo,
 (b) —OH,
 (c) —CN,
 (d) —$NO_2$,
 (e) —$C_{1-6}$ alkyl
 (f) —$C_{2-6}$ alkenyl
 (g) —$C_{3-6}$ cycloalkyl,
 (h) —O—$C_{1-6}$ alkyl,
 (i) —O—$CH_2$-aryl,
 (j) —$C_{6-10}$ aryl,
 (k) heteroaryl, wherein said heteroaryl is an aromatic cyclic group having 5 to 12 ring atoms, at least one of which is O, N or S,
 (l) —$NR^{6A}R^{6B}$,
 (m) —$NR^{6A}C(=O)R^{6B}$,
 (n) a heterocyclic group having 4 to 8 ring atoms, wherein one ring atom is a heteroatom selected from the group consisting of nitrogen, sulfur and oxygen,
 (o) —$SO_2C_{1-3}$ alkyl,
 (p) —$SO_2NR^{6A}R^{6B}$, and
 (q) —$CONR^{6A}R^{6B}$,
 wherein said alkyl, alkenyl, cycloalkyl, aryl and heteroaryl moiety is optionally substituted with one or more groups independently selected form the group consisting of:
 (I) halo,
 (II) —$C_{1-6}$ alkyl, wherein said alkyl is optionally substituted with one or more fluoro,
 (III) —O—$C_{1-6}$ alkyl, wherein said alkyl is optionally substituted with one or more fluoro,
 (IV) —$NHSO_2R^9$, and
 (V) OH;

$R^4$ is selected from the group consisting of:
 (1) hydrogen, and
 (2) —$C_{1-6}$ alkyl,
 wherein said alkyl is optionally substituted with one or more groups independently selected from the group consisting of:
 (a) halogen
 (b) hydroxyl,
 (c) —$C_{6-10}$ aryl,
 (d) heteroaryl, wherein said heteroaryl is an aromatic cyclic group having 5 to 12 ring atoms, at least one of which is O, N or S,
 (e) —$OC_{1-4}$ alkyl, and
 (f) —$C(=O)OR^9$,
 and wherein said alkyl, aryl or heteroaryl is optionally substituted with one or more groups independently selected from the group consisting of:
 (I) hydroxy,
 (II) fluoro,
 (III) —$C_{1-4}$ alkyl, optionally substituted by fluoro; and
 (IV) —$OC_{1-4}$ alkyl;

$R^5$ is selected from the group consisting of:
 (1) hydrogen,
 (2) —$C_{1-6}$ alkyl, and
 (3) a heterocyclic group having 4 to 8 ring atoms, wherein at least one ring atom is a heteroatom selected from the group consisting of nitrogen, sulfur and oxygen,
 wherein said alkyl or heterocyclyl is optionally substituted with one or more groups independently selected from the group consisting of:
 (a) halogen
 (b) hydroxyl,
 (c) —$C_{6-10}$ aryl,
 (d) heteroaryl, wherein said heteroaryl is an aromatic cyclic group having 5 to 12 ring atoms, at least one of which is O, N or S,
 (e) a heterocyclic group having 4 to 8 ring atoms, wherein at least one ring atom is a heteroatom selected from the group consisting of nitrogen, sulfur and oxygen,
 (f) —$OC_{1-4}$ alkyl,
 (g) —CN, and
 (h) —$C(=O)$—$OR^9$,
 wherein said aryl, heteroaryl or heterocyclic group is optionally substituted with one or more groups independently selected from the group consisting of:
 (I) hydroxy,
 (II) fluoro,
 (III) —$C_{1-4}$ alkyl, optionally substituted by fluoro,
 (IV) —$OC_{1-4}$ alkyl,
 (V) —$(CH_2)_n$—$C_{6-10}$ aryl,
 (VI) heteroaryl, and
 (VII) —$C(=O)OR^9$;

$R^{6A}$ and $R^{6B}$ are independently selected from the group consisting of:
 (1) hydrogen,
 (2) halogen,
 (3) $C_{1-6}$alkyl,
 (4) O—$C_{1-6}$alkyl,
 (5) —$NO_2$,
 (6) cyano (7) OH
(8) —(CH$_2$)$_m$aryl, and
(9) —NR$^7$R$^8$, wherein R$^7$ and R$^8$ are independently selected from the group consisting of
  (I) hydrogen,
  (II) —C$_{1-6}$ alkyl, and
  (III) —C$_{3-6}$ cycloalkyl,
  or R$^7$ and R$^8$ are linked together with the nitrogen to which they are both attached to form a 2-6 membered carbocyclic ring, wherein one or two of the ring carbon atoms is replaced by a nitrogen, oxygen or sulfur,
  wherein said R$^{6A}$ or R$^{6B}$ alkyl or aryl moiety is optionally substituted with one or more groups independently selected from the group consisting of:
  (a) halo,
  (b) —C$_{1-6}$ alkyl,
  (c) —O—C$_{1-6}$ alkyl, and
  (d) -aryl,
  wherein said alkyl or aryl is optionally substituted with one or more halo;
R$^9$ is selected from the group consisting of:
  (1) hydrogen,
  (2) C$_{1-4}$ alkyl, and
  (3) —C$_{3-8}$ cycloalkyl,
n is 0 or 1; and
m is 0, 1, 2 or 3;
provided that when R$^2$, R$^4$ and R$^5$ are each hydrogen, then R$^1$ is not 4-methoxyphenyl and R$^3$ is not (1-methoxy-4-nitrophenyl)methylene;
or a pharmaceutically acceptable salt thereof.

2. A compound of claim 1, or a pharmaceutically acceptable salt thereof, wherein R$^1$ is selected from the group consisting of phenyl, 4-methoxyphenyl, 3-methoxyphenyl, 2-methoxyphenyl, 2-bromo-4-methoxyphenyl, 4-chlorophenyl, 3-fluoro-4-methoxyphenyl, 2-nitro-4,5-dimethoxyphenyl and 2-bromo-4,5-dimethoxyphenyl.

3. A compound of claim 1, or a pharmaceutically acceptable salt thereof, wherein R$^3$ is benzyl,
and wherein said benzyl moiety is optionally substituted with one or more
  (a) halo,
  (b) —NO$_2$,
  (c) —CN,
  (d) —C$_{1-6}$ alkyl,
  (e) —C$_{2-6}$ alkenyl,
  (f) —C$_{3-6}$ cycloalkyl,
  (g) —O—C$_{1-6}$ alkyl,
  (h) —(C$_{6-10}$) aryl, or
  (i) heteroaryl,
wherein said alkyl, aryl or heteroaryl moiety is optionally substituted with one or more
  (I) halo,
  (II) —C$_{1-6}$ alkyl, wherein said alkyl is optionally substituted with one or more fluoro,
  (III) —O—C$_{1-6}$ alkyl, wherein said alkyl is optionally substituted with one or more fluoro,
  (IV) —NSO$_2$R$^9$, or OH.

4. A compound of claim 3, or a pharmaceutically acceptable salt thereof, wherein R$^4$ is hydrogen.

5. A compound of claim 3, or a pharmaceutically acceptable salt thereof, wherein R$^4$ is a C$_{1-6}$ alkyl group, which is substituted by one or more
  (a) halogen
  (b) hydroxyl,
  (c) —C$_{6-10}$ aryl,
  (d) heteroaryl, wherein said heteroaryl is an aromatic cyclic group having 5 to 12 ring atoms, at least one of which is O, N, or S, or
  (e) —C(=O)OR$^9$,
and wherein said alkyl, aryl or heteroaryl is optionally substituted with one or more
  (I) hydroxy,
  (II) fluoro, or
  (III) —OC$_{1-4}$ alkyl.

6. A compound claim 5, or a pharmaceutically acceptable salt thereof, wherein R$^5$ is hydrogen, methyl or ethyl.

7. A compound claim 5, or a pharmaceutically acceptable salt thereof, wherein R$^5$ is a substituted C$_{1-6}$ alkyl group, which is substituted by one or more
  (a) halogen
  (b) hydroxyl,
  (c) —C$_{6-10}$ aryl,
  (d) heteroaryl, or
  (e) a heterocyclic group having 4 to 8 ring atoms, wherein at least one ring atom is a heteroatom selected from the group consisting of nitrogen, sulfur and oxygen,
wherein said aryl, heteroaryl or heterocyclic group is optionally substituted with one or more
  (I) hydroxy,
  (II) fluoro, or
  (III) —OC$_{1-4}$ alkyl.

8. A compound of formula (II):

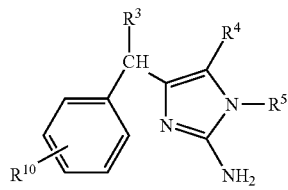

or a pharmaceutically acceptable salt thereof, wherein R$^{10}$ is optionally present at one or more of the ring carbon atoms, and each R$^{10}$ is independently selected from the group consisting of
  (a) halo,
  (b) —OH,
  (c) —CN,
  (d) —C$_{1-6}$ alkyl,
  (e) —C$_{2-6}$ alkenyl,
  (f) —C$_{3-6}$ cycloalkyl,
  (g) —NO$_2$,
  (h) —O—C$_{1-6}$ alkyl, and
  (i) phenyl;
R$^3$ is selected from the group consisting of:
  —(CH$_2$)$_n$-phenyl,
  wherein said phenyl moiety is optionally independently substituted with one or more groups independently selected from the group consisting of:
  (a) halo,
  (b) —OH,
  (c) —CN,
  (d) —NO$_2$,
  (e) —C$_{1-6}$ alkyl
  (f) —C$_{2-6}$ alkenyl
  (g) —C$_{3-6}$ cycloalkyl,
  (h) —O—C$_{1-6}$ alkyl,
  (i) —O—CH$_2$-aryl,
  (j) —C$_{6-10}$ aryl, (k) heteroaryl, wherein said heteroaryl is an aromatic cyclic group having 5 to 12 ring atoms, at least one of which is O, N or S,
(l) —NR$^{6A}$R$^{6B}$,
(m) —NR$^{6A}$C(=O)R$^{6B}$,
(n) a heterocyclic group having 4 to 8 ring atoms, wherein one ring atom is a heteroatom selected from the group consisting of nitrogen, sulfur and oxygen,
(o) —SO$_2$C$_{1-3}$ alkyl,
(p) —SO$_2$NR$^{6A}$R$^{6B}$, and
(q) —CONR$^{6A}$R$^{6B}$,
wherein said alkyl, alkenyl, cycloalkyl, aryl and heteroaryl moiety is optionally substituted with one or more groups independently selected form the group consisting of:
(I) halo,
(II) —C$_{1-6}$ alkyl, wherein said alkyl is optionally substituted with one or more fluoro,
(III) —O—C$_{1-6}$ alkyl, wherein said alkyl is optionally substituted with one or more fluoro,
(IV) —NHSO$_2$R$^9$ and
(V) OH;
R$^4$ is selected from the group consisting of:
(1) hydrogen, and
(2) —C$_{1-6}$ alkyl,
wherein said alkyl is optionally substituted with one or more groups independently selected from the group consisting of:
(a) halogen
(b) hydroxyl,
(c) —C$_{6-10}$ aryl,
(d) heteroaryl, wherein said heteroaryl is an aromatic cyclic group having 5 to 12 ring atoms, at least one of which is O, N or S,
(e) —OC$_{1-4}$ alkyl, and
(f) —C(=O)OR$^9$,
and wherein said alkyl, aryl or heteroaryl is optionally substituted with one or more groups independently selected from the group consisting of:
(I) hydroxy,
(II) fluoro,
(III) —C$_{1-4}$ alkyl, optionally substituted by fluoro; and
(IV) —OC$_{1-4}$ alkyl;
R$^5$ is selected from the group consisting of:
(1) hydrogen,
(2) —C$_{1-6}$ alkyl, and
(3) a heterocyclic group having 4 to 8 ring atoms, wherein at least one ring atom is a heteroatom selected from the group consisting of nitrogen, sulfur and oxygen,
wherein said alkyl or heterocyclyl is optionally substituted with one or more groups independently selected from the group consisting of:
(a) halogen
(b) hydroxyl,
(c) —C$_{6-10}$ aryl,
(d) heteroaryl, wherein said heteroaryl is an aromatic cyclic group having 5 to 12 ring atoms, at least one of which is O, N or S,
(e) a heterocyclic group having 4 to 8 ring atoms, wherein at least one ring atom is a heteroatom selected from the group consisting of nitrogen, sulfur and oxygen,
(f) —OC$_{1-4}$ alkyl,
(g) —CN, and
(h) —C(=O)—OR$^9$,
wherein said aryl, heteroaryl or heterocyclic group is optionally substituted with one or more groups independently selected from the group consisting of:
(I) hydroxy,
(II) fluoro,
(III) —C$_{1-4}$ alkyl, optionally substituted by fluoro,
(IV) —OC$_{1-4}$ alkyl,
(V) —(CH$_2$)$_n$—C$_{6-10}$ aryl,
(VI) heteroaryl, and
(VII) —C(=O)OR$^9$;
R$^{6A}$ and R$^{6B}$ are independently selected from the group consisting of:
(1) hydrogen,
(2) halogen,
(3) C$_{1-6}$alkyl,
(4) O—C$_{1-6}$alkyl,
(5) —NO$_2$,
(6) cyano
(7) OH
(8) —(CH$_2$)$_m$aryl, and
(9) —NR$^7$R$^8$, wherein R$^7$ and R$^8$ are independently selected from the group consisting of
(I) hydrogen,
(II) —C$_{1-6}$ alkyl, and
(III) —C$_{3-6}$ cycloalkyl,
or R$^7$ and R$^8$ are linked together with the nitrogen to which they are both attached to form a 2-6 membered carbocyclic ring, wherein one or two of the ring carbon atoms is replaced by a nitrogen, oxygen or sulfur,
wherein said R$^{6A}$ or R$^{6B}$ alkyl or aryl moiety is optionally substituted with one or more groups independently selected from the group consisting of:
(a) halo,
(b) —C$_{1-6}$ alkyl,
(c) —O—C$_{1-6}$ alkyl, and
(d) -aryl,
wherein said alkyl or aryl is optionally substituted with one or more halo;
R$^9$ is selected from the group consisting of:
(1) hydrogen,
(2) C$_{1-4}$ alkyl, and
(3) —C$_{3-8}$ cycloalkyl,
n is o or 1; and
m is 0, 1, 2 or 3;
provided that when R$^4$ and R$^5$ are each hydrogen, then R$^{10}$ is not 4-methoxy and R$^3$ is not (1-methoxy-4-nitrophenyl)methylene;
or a pharmaceutically acceptable salt thereof.

9. A compound of formula (III):

(III)

or a pharmaceutically acceptable salt thereof, wherein:
R$^{10}$ is optionally present at one or more of the ring carbon atoms, and each R$^{10}$ is selected from the group consisting of (a) halo,
(b) —OH,
(c) —CN,
(d) —$C_{1-6}$ alkyl,
(e) —$C_{2-6}$ alkenyl,
(f) —$C_{3-6}$ cycloalkyl,
(g) —$NO_2$,
(h) 0-O—$C_{1-6}$ alkyl, and
(i) phenyl;

$R^{11}$ is optionally present at one or more of the ring carbon atoms, and each $R^{11}$ is selected from the group consisting of:
(a) halo,
(b) —$NO_2$,
(c) —CN,
(d) —$C_{1-6}$ alkyl,
(e) —$C_{2-6}$ alkenyl,
(f) —$C_{3-6}$ cycloalkyl,
(g) —O—$C_{1-6}$ alkyl,
(h) aryl,
(i) heteroaryl,
wherein said alkyl, aryl or heteroaryl moiety is optionally substituted with one or more
(I) halo,
(II) —$C_{1-6}$ alkyl, wherein said alkyl is optionally substituted with one or more fluoro,
(III) —O—$C_{1-6}$ alkyl, wherein said alkyl is optionally substituted with one or more fluoro,
(IV) —$NSO_2R^9$, or
(V) OH;

$R^4$ is selected from the group consisting of:
(1) hydrogen, and
(2) —$C_{1-6}$ alkyl,
wherein said alkyl is optionally substituted with one or more groups independently selected from the group consisting of:
(a) halogen
(b) hydroxyl,
(c) —$C_{6-10}$ aryl,
(d) heteroaryl, wherein said heteroaryl is an aromatic cyclic group having 5 to 12 ring atoms, at least one of which is O, N or S,
(e) —$OC_{1-4}$ alkyl, and
(f) —C(=O)$OR^9$,
and wherein said alkyl, aryl or heteroaryl is optionally substituted with one or more groups independently selected from the group consisting of:
(I) hydroxy,
(II) fluoro,
(III) —$C_{1-4}$ alkyl, optionally substituted by fluoro; and
(IV) —$OC_{1-4}$ alkyl;

$R^5$ is selected from the group consisting of:
(1) hydrogen,
(2) —$C_{1-6}$ alkyl, and
(3) a heterocyclic group having 4 to 8 ring atoms, wherein at least one ring atom is a heteroatom selected from the group consisting of nitrogen, sulfur and oxygen,
wherein said alkyl or heterocyclyl is optionally substituted with one or more groups independently selected from the group consisting of:
(a) halogen
(b) hydroxyl,
(c) —$C_{6-10}$ aryl,
(d) heteroaryl, wherein said heteroaryl is an aromatic cyclic group having 5 to 12 ring atoms, at least one of which is O, N or S,
(e) a heterocyclic group having 4 to 8 ring atoms, wherein at least one ring atom is a heteroatom selected from the group consisting of nitrogen, sulfur and oxygen,
(f) —$OC_{1-4}$ alkyl,
(g) —CN, and
(h) —C(=O)—$OR^9$,
wherein said alkyl, aryl, heteroaryl or heterocyclic group is optionally substituted with one or more groups independently selected from the group consisting of:
(I) hydroxy,
(II) fluoro,
(III) —$C_{1-4}$ alkyl, optionally substituted by fluoro,
(IV) —$OC_{1-4}$ alkyl,
(V) —$(CH_2)_n$—$C_{6-10}$ aryl,
(VI) heteroaryl, and
(VII) —C(=O)$OR^9$;

$R^{6A}$ and $R^{6B}$ are independently selected from the group consisting of:
(1) hydrogen,
(2) halogen,
(3) $C_{1-6}$alkyl,
(4) O—$C_{1-6}$alkyl,
(5) —$NO_2$,
(6) cyano
(7) OH
(8) —$(CH_2)_m$aryl, and
(9) —$NR^7R^8$, wherein $R^7$ and $R^8$ are independently selected from the group consisting of
(I) hydrogen,
(II) —$C_{1-6}$ alkyl, and
(III) —$C_{3-6}$ cycloalkyl,
or $R^7$ and $R^8$ are linked together with the nitrogen to which they are both attached to form a 2-6 membered carbocyclic ring, wherein one or two of the ring carbon atoms is replaced by a nitrogen, oxygen or sulfur,
wherein said $R^{6A}$ or $R^{6B}$ alkyl or aryl moiety is optionally substituted with one or more groups independently selected from the group consisting of:
(a) halo,
(b) —$C_{1-6}$ alkyl,
(c) —O—$C_{1-6}$ alkyl, and
(d) -aryl,
wherein said alkyl or aryl is optionally substituted with one or more halo;

$R^9$ is selected from the group consisting of:
(1) hydrogen,
(2) $C_{1-4}$ alkyl, and
(3) —$C_{3-8}$ cycloalkyl,
n is 0 or 1; and
m is 0, 1, 2 or 3;
or a pharmaceutically acceptable salt thereof.

10. A compound which is selected from the group consisting of:

| Ex. No. | Structure | IUPAC Name |
|---|---|---|
| 1 | 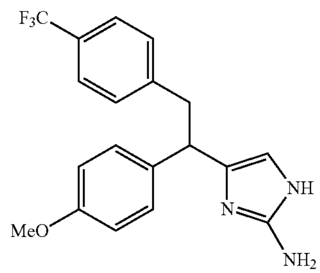 [SMILES: COc1ccc(C(Cc2ccc(C(F)(F)F)cc2)c2c[nH]c(N)n2)cc1] | 4-{(1S)-1-(4-methoxylphenyl)-2-[4-(trifluoromethyl)phenyl]ethyl}-1-H-imidazole-2-amine |
| 2 | 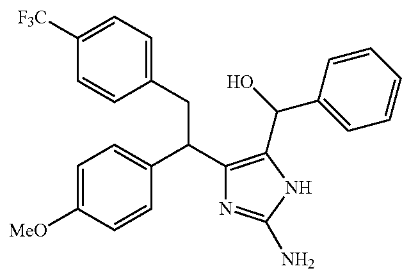 [SMILES: COc1ccc(C(Cc2ccc(C(F)(F)F)cc2)c2nc(N)[nH]c2C(O)c2ccccc2)cc1] | (2-amino-4-{(1S)-1-(4-methoxyphenyl)-2-[4-(trifluoromethyl)phenyl]ethyl}-1H-imidazole-5-yl)(phenyl)methanol |
| 4 | 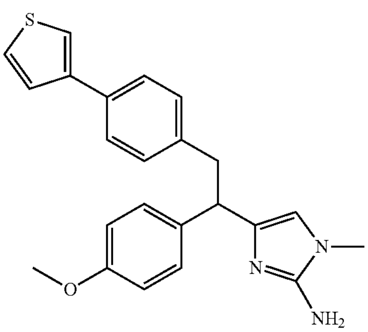 [SMILES: COc1ccc(C(Cc2ccc(-c3ccsc3)cc2)c2cn(C)c(N)n2)cc1] | 4-{1-(4-methoxyphenyl)-2-[4-(3-thienyl)phenyl]ethyl}-1-methyl-1H-imidazol-2-amine |
| 7 | 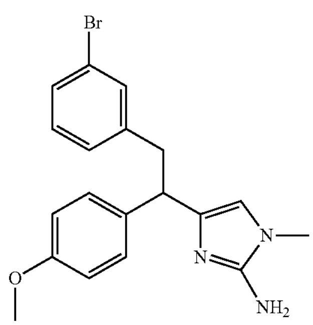 [SMILES: COc1ccc(C(Cc2cccc(Br)c2)c2cn(C)c(N)n2)cc1] | 4-[1-(3-fluoro-4-methoxyphenyl)-2-(2-methoxy-5-nitrophenyl)ethyl]-1H-imidazol-2-amine |
| 8 | 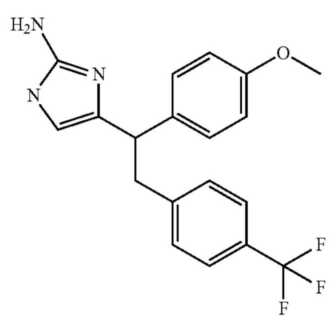 [SMILES: COc1ccc(C(Cc2ccc(C(F)(F)F)cc2)c2c[nH]c(N)n2)cc1] | 4-{1-(4-methoxyphenyl)-2-[4-(trifluoromethyl)phenyl]ethyl}-1H-imidazol-2-amine |

| Ex. No. | Structure | IUPAC Name |
|---|---|---|
| 9 | 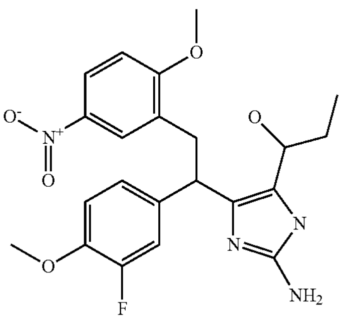 [SMILES: CCC(O)c1[nH]c(N)nc1C(Cc1cc([N+](=O)[O-])ccc1OC)c1ccc(OC)c(F)c1] | 1-{2-amino-4-[1-(3-fluoro-4-methoxyphenyl)-2-(2-methoxy-5-nitrophenyl)ethyl]-1H-imidazol-5-yl}propan-1-ol |
| 10 | 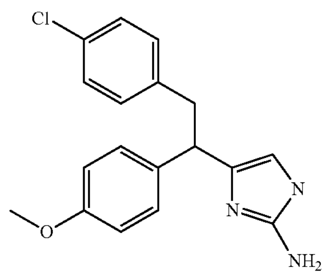 [SMILES: COc1ccc(C(Cc2ccc(Cl)cc2)c2c[nH]c(N)n2)cc1] | 4-[2-(4-chlorophenyl)-1-(4-methoxyphenyl)ethyl]-1H-imidazol-2-amine |
| 11 | 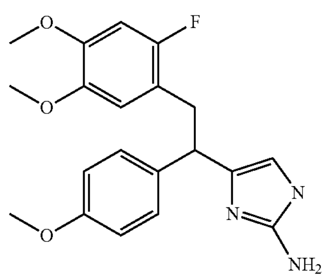 [SMILES: COc1ccc(C(Cc2cc(OC)c(OC)cc2F)c2c[nH]c(N)n2)cc1] | 4-[2-(2-fluoro-4,5-dimethoxyphenyl)-1-(4-methoxyphenyl)ethyl]-1H-imidazol-2-amine |
| 12 | 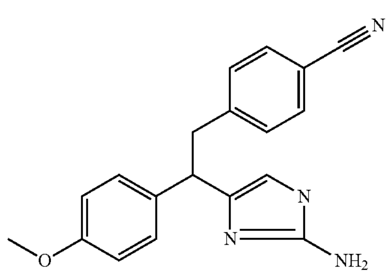 [SMILES: COc1ccc(C(Cc2ccc(C#N)cc2)c2c[nH]c(N)n2)cc1] | 4-[2-(2-amino-1H-imidazol-4-yl)-2-(4-methoxyphenyl)ethyl]benzonitrile |
| 14 | 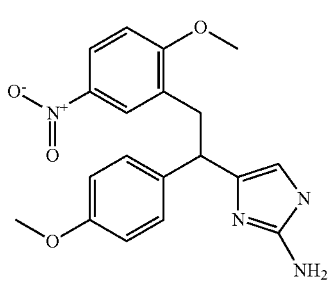 | 4-[2-(2-methoxy-5-nitrophenyl)-1-(4-methoxyphenyl)ethyl]-1H-imidazol-2-amine |

-continued

| Ex. No. | Structure | IUPAC Name |
|---|---|---|
| 15 | 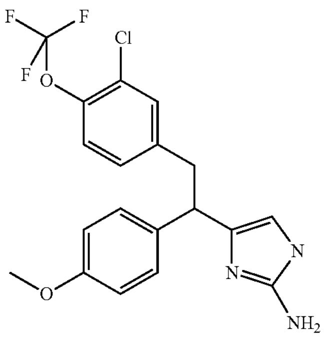 [SMILES: COc1ccc(C(Cc2ccc(OC(F)(F)F)c(Cl)c2)c2c[nH]c(N)n2)cc1] | 4-[2-[3-chloro-4-(trifluoromethoxy)phenyl]-1-(4-methoxyphenyl)ethyl]-1H-imidazol-2-amine |
| 16 | 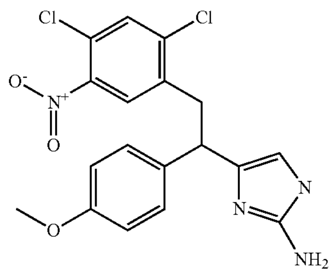 [SMILES: COc1ccc(C(Cc2cc([N+](=O)[O-])c(Cl)cc2Cl)c2c[nH]c(N)n2)cc1] | 4-[2-(2,4-dichloro-5-nitrophenyl)-1-(4-methoxyphenyl)ethyl]-1H-imidazol-2-amine |
| 17 | 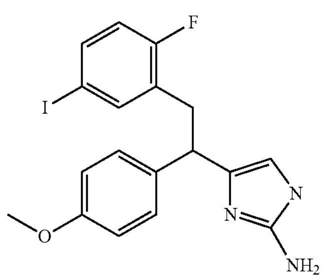 [SMILES: COc1ccc(C(Cc2cc(I)ccc2F)c2c[nH]c(N)n2)cc1] | 4-[2-(2-fluoro-5-iodophenyl)-1-(4-methoxyphenyl)ethyl]-1H-imidazol-2-amine |
| 19 | 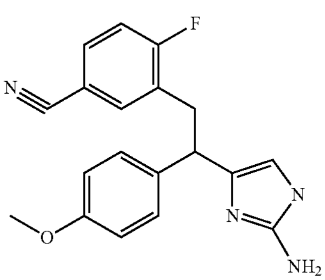 [SMILES: COc1ccc(C(Cc2cc(C#N)ccc2F)c2c[nH]c(N)n2)cc1] | 3-[2-(2-amino-1H-imidazol-4-yl)-2-(4-methoxyphenyl)ethyl]-4-fluorobenzonitrile |
| 20 | 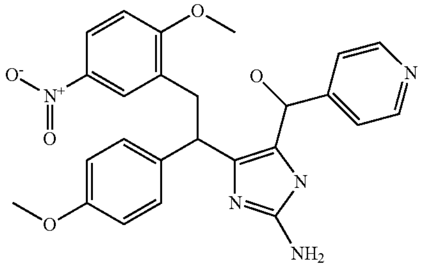 [SMILES: COc1ccc(C(Cc2cc([N+](=O)[O-])ccc2OC)c2nc(N)[nH]c2C(O)c2ccncc2)cc1] | {2-amino-4-[2-(2-methoxy-5-nitrophenyl)-1-(4-methoxyphenyl)ethyl]-1H-imidazol-5-yl}(pyridin-4-yl)methanol |

-continued

| Ex. No. | Structure | IUPAC Name |
|---|---|---|
| 22 | 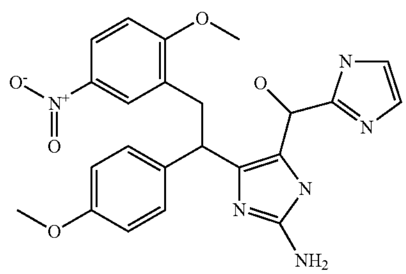 [SMILES: COc1ccc(C(Cc2cc([N+](=O)[O-])ccc2OC)c2nc(N)[nH]c2C(O)c2ncc[nH]2)cc1] | {2-amino-4-[2-(2-methoxy-5-nitrophenyl)-1-(4-methoxyphenyl)ethyl]-1H-imidazol-5-yl}(1H-imidazol-2-yl)methanol |
| 23 | 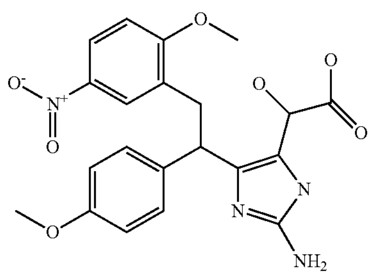 [SMILES: COc1ccc(C(Cc2cc([N+](=O)[O-])ccc2OC)c2nc(N)[nH]c2C(O)C(=O)O)cc1] | {2-amino-4-[2-(2-methoxy-5-nitrophenyl)-1-(4-methoxyphenyl)ethyl]-1H-imidazol-5-yl}(hydroxy)acetic acid |
| 24 | 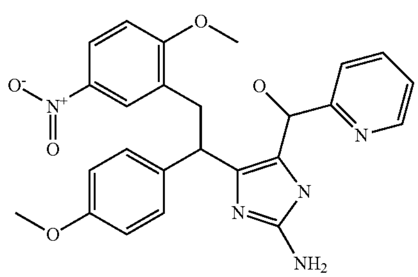 [SMILES: COc1ccc(C(Cc2cc([N+](=O)[O-])ccc2OC)c2nc(N)[nH]c2C(O)c2ccccn2)cc1] | {2-amino-4-[2-(2-methoxy-5-nitrophenyl)-1-(4-methoxyphenyl)ethyl]-1H-imidazol-5-yl}(pyridin-2-yl)methanol |
| 25 | 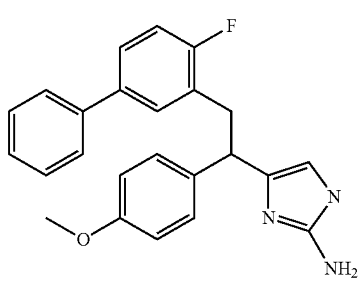 [SMILES: COc1ccc(C(Cc2cc(-c3ccccc3)ccc2F)c2c[nH]c(N)n2)cc1] | 4-[2-(4-fluorobiphenyl-3-yl)-1-(4-methoxyphenyl)ethyl]-1H-imidazol-2-amine |
| 26 | 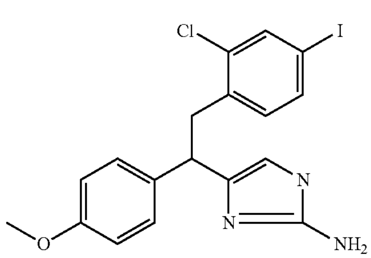 [SMILES: COc1ccc(C(Cc2ccc(I)cc2Cl)c2c[nH]c(N)n2)cc1] | 4-[2-(2-chloro-4-iodophenyl)-1-(4-methoxyphenyl)ethyl]-1H-imidazol-2-amine |

| Ex. No. | Structure | IUPAC Name |
|---|---|---|
| 27 | 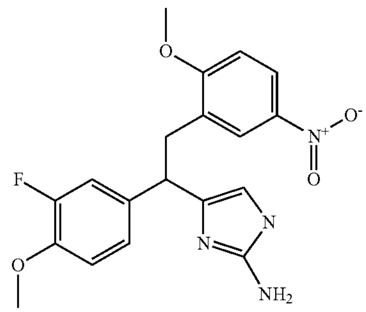 [SMILES: COc1ccc(C(Cc2cc([N+](=O)[O-])ccc2OC)c2c[nH]c(N)n2)cc1F] | 4-[1-(3-fluoro-4-methoxyphenyl)-2-(2-methoxy-5-nitrophenyl)ethyl]-1H-imidazol-2-amine |
| 28 | 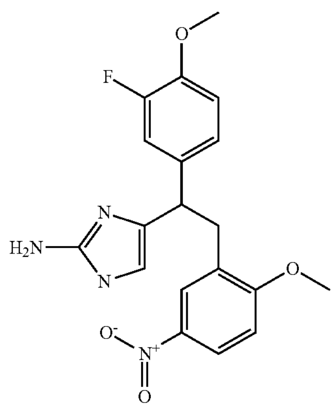 [SMILES: COc1ccc(C(Cc2cc([N+](=O)[O-])ccc2OC)c2c[nH]c(N)n2)cc1F] | 4-[1-(3-fluoro-4-methoxyphenyl)-2-(2-methoxy-5-nitrophenyl)ethyl]-1H-imidazol-2-amine |
| 29 | 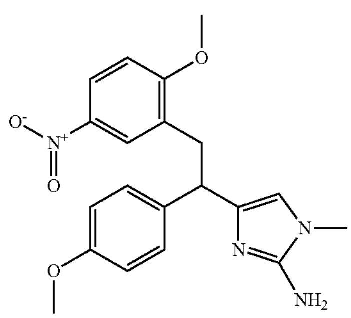 [SMILES: COc1ccc(C(Cc2cc([N+](=O)[O-])ccc2OC)c2cn(C)c(N)n2)cc1] | 4-[2-(2-methoxy-5-nitrophenyl)-1-(4-methoxyphenyl)ethyl]-1-methyl-1H-imidazol-2-amine |
| 30 | 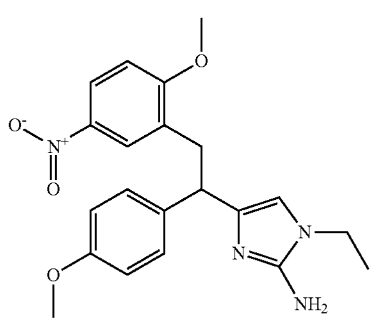 [SMILES: CCn1cc(C(Cc2cc([N+](=O)[O-])ccc2OC)c2ccc(OC)cc2)nc1N] | 1-ethyl-4-[2-(2-methoxy-5-nitrophenyl)-1-(4-methoxyphenyl)ethyl]-1H-imidazol-2-amine |

| Ex. No. | Structure | IUPAC Name |
|---|---|---|
| 31 | 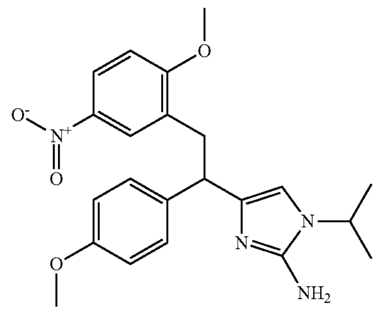 [SMILES: COc1ccc(C(Cc2cc([N+](=O)[O-])ccc2OC)c2cn(C(C)C)c(N)n2)cc1] | 1-isopropyl-4-[2-(2-methoxy-5-nitrophenyl)-1-(4-methoxyphenyl)ethyl]-1H-imidazol-2-amine |
| 32 | 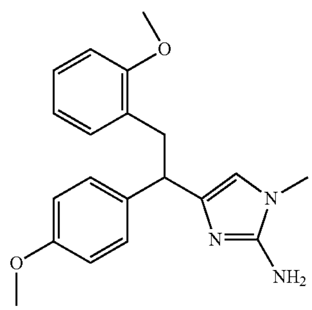 [SMILES: COc1ccc(C(Cc2ccccc2OC)c2cn(C)c(N)n2)cc1] | 4-[2-(2-methoxyphenyl)-1-(4-methoxyphenyl)ethyl]-1-methyl-1H-imidazol-2-amine |
| 33 | 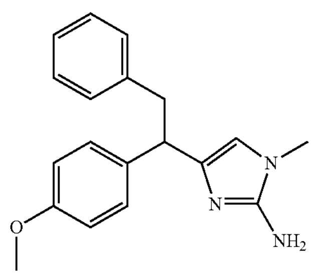 [SMILES: COc1ccc(C(Cc2ccccc2)c2cn(C)c(N)n2)cc1] | 4-[1-(4-methoxyphenyl)-2-phenylethyl]-1-methyl-1H-imidazol-2-amine |
| 34 | 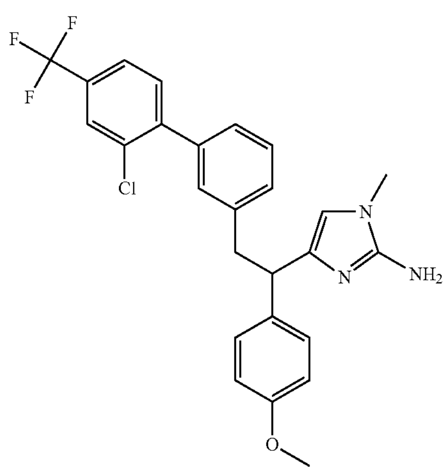 [SMILES: COc1ccc(C(Cc2cccc(-c3ccc(C(F)(F)F)cc3Cl)c2)c2cn(C)c(N)n2)cc1] | 4-[2-[2'-chloro-4'-(trifluoromethyl)biphenyl-3-yl]-1-(4-methoxyphenyl)ethyl]-1-methyl-1H-imidazol-2-amine |

-continued

| Ex. No. | Structure | IUPAC Name |
|---|---|---|
| 35 | 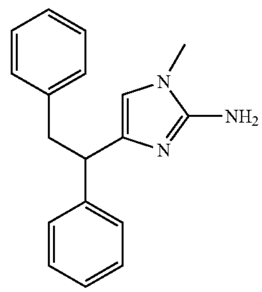 [SMILES: Cn1cc(C(Cc2ccccc2)c2ccccc2)nc1N] | 4-(1,2-diphenylethyl)-1-methyl-1H-imidazol-2-amine |
| 36 | 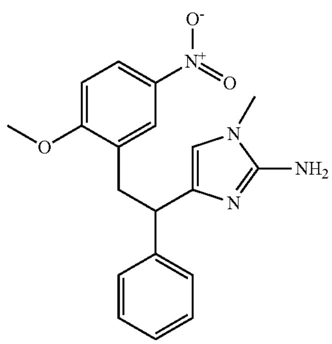 [SMILES: COc1ccc([N+](=O)[O-])cc1CC(c1ccccc1)c1cn(C)c(N)n1] | 4-[1-(4-methoxyphenyl)-2-(3-nitrophenyl)ethyl]-1-methyl-1H-imidazol-2-amine |
| 37 | 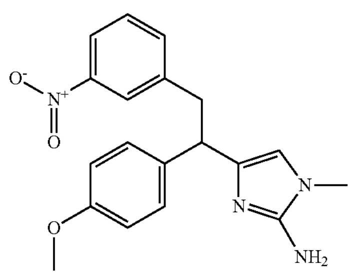 [SMILES: COc1ccc(C(Cc2cccc([N+](=O)[O-])c2)c2cn(C)c(N)n2)cc1] | 4-[1-(4-methoxyphenyl)-2-(3-nitrophenyl)ethyl]-1-methyl-1H-imidazol-2-amine |
| 38 | 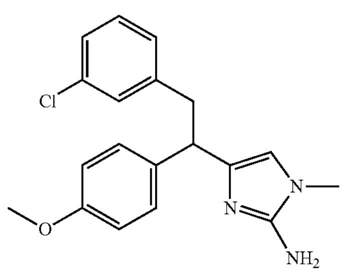 | 4-[2-(3-chlorophenyl)-1-(4-methoxyphenyl)ethyl]-1-methyl-1H-imidazol-2-amine |
| 39 | 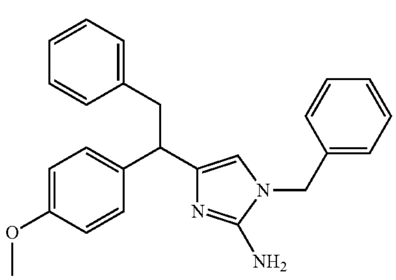 [SMILES: COc1ccc(C(Cc2ccccc2)c2cn(Cc3ccccc3)c(N)n2)cc1] | 1-benzyl-4-[1-(4-methoxyphenyl)-2-phenylethyl]-1H-imidazol-2-amine |

| Ex. No. | Structure | IUPAC Name |
|---|---|---|
| 40 | 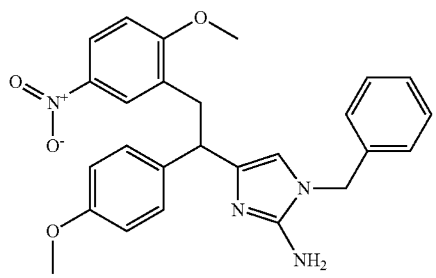 [SMILES: COc1ccc(C(Cc2cc([N+](=O)[O-])ccc2OC)c2cn(Cc3ccccc3)c(N)n2)cc1] | 1-benzyl-4-[2-(2-methoxy-5-nitrophenyl)-1-(4-methoxyphenyl)ethyl]-1H-imidazol-2-amine |
| 43 | 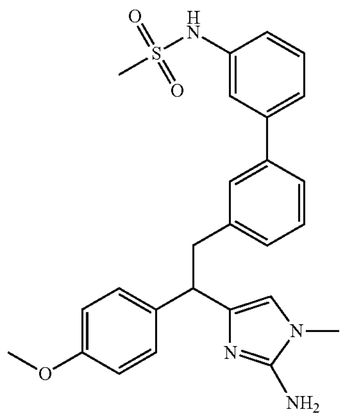 | N-{3'-[2-(2-amino-1-methyl-1H-imidazol-4-yl)-2-(4-methoxyphenyl)ethyl]biphenyl-3-yl}methanesulfonamide |
| 44 | 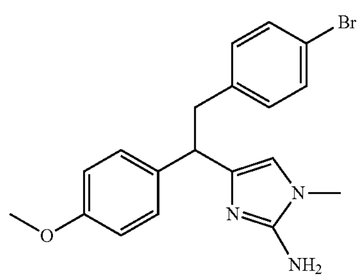 [SMILES: COc1ccc(C(Cc2ccc(Br)cc2)c2cn(C)c(N)n2)cc1] | 4-[2-(4-bromophenyl)-1-(4-methoxyphenyl)ethyl]-1-methyl-1H-imidazol-2-amine |
| 45 | 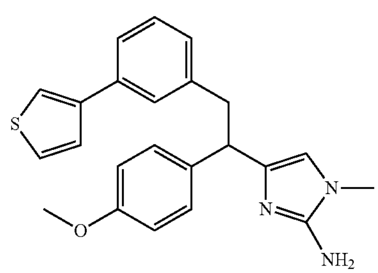 [SMILES: COc1ccc(C(Cc2cccc(-c3ccsc3)c2)c2cn(C)c(N)n2)cc1] | 4-{1-(4-methoxyphenyl)-2-[3-(3-thienyl)phenyl]ethyl}-1-methyl-1H-imidazol-2-amine |
| 46 | 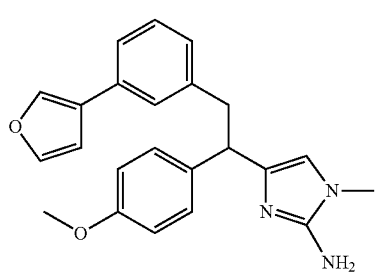 [SMILES: COc1ccc(C(Cc2cccc(-c3ccoc3)c2)c2cn(C)c(N)n2)cc1] | 4-[2-[3-(3-furyl)phenyl]-1-(4-methoxyphenyl)ethyl]-1-methyl-1H-imidazol-2-amine |

-continued

| Ex. No. | Structure | IUPAC Name |
|---|---|---|
| 47 | 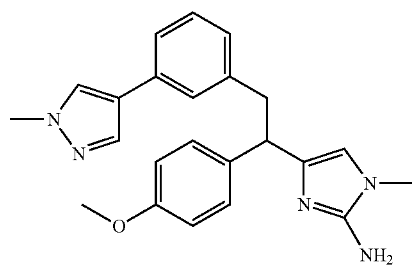 | 4-{1-(4-methoxyphenyl)-2-[3-(1-methyl-1H-pyrazol-4-yl)phenyl]ethyl}-1-methyl-1H-imidazol-2-amine |
| 48 | 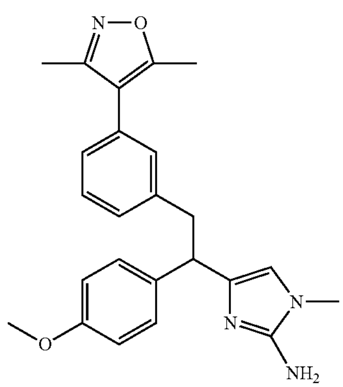 | 4-[2-[3-(3,5-dimethylisoxazol-4-yl)phenyl]-1-(4-methoxyphenyl)ethyl]-1-methyl-1H-imidazol-2-amine |
| 49 | 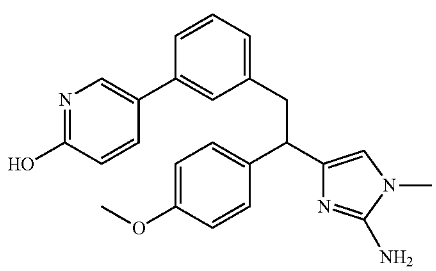 [SMILES: COc1ccc(C(Cc2cccc(-c3ccc(O)nc3)c2)c2cn(C)c(N)n2)cc1] | 5-{3-[2-(2-amino-1-methyl-1H-imidazol-4-yl)-2-(4-methoxyphenyl)ethyl]phenyl}pyridin-2-ol |
| 50 | 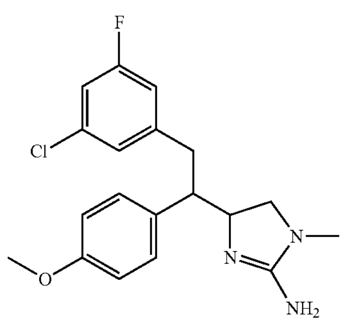 | 4-[2-(3-chloro-5-fluorophenyl)-1-(4-methoxyphenyl)ethyl]-1-methyl-1H-imidazol-2-amine |
| 51 | 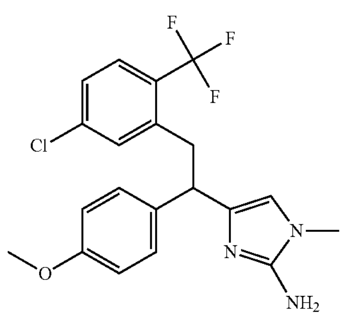 | 4-[2-[5-chloro-2-(trifluoromethyl)phenyl]-1-(4-methoxyphenyl)ethyl]-1-methyl-1H-imidazol-2-amine |

| Ex. No. | Structure | IUPAC Name |
|---|---|---|
| 52 | 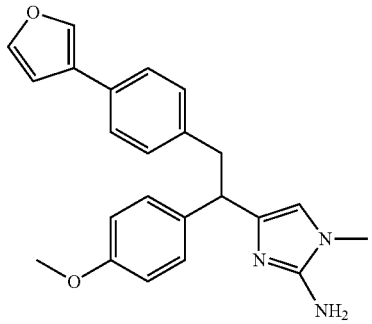 [SMILES: COc1ccc(C(Cc2ccc(-c3ccoc3)cc2)c2cn(C)c(N)n2)cc1] | 4-[2-[4-(3-furyl)phenyl]-1-(4-methoxyphenyl)ethyl]-1-methyl-1H-imidazol-2-amine |
| 53 | 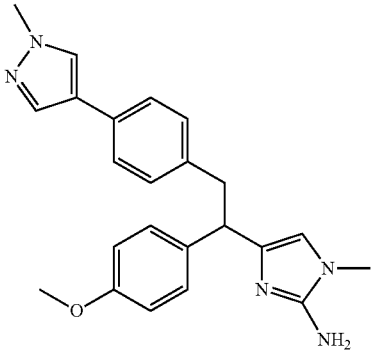 [SMILES: COc1ccc(C(Cc2ccc(-c3cnn(C)c3)cc2)c2cn(C)c(N)n2)cc1] | 4-{1-(4-methoxyphenyl)-2-[4-(1-methyl-1H-pyrazol-4-yl)phenyl]ethyl}-1-methyl-1H-imidazol-2-amine |
| 54 | 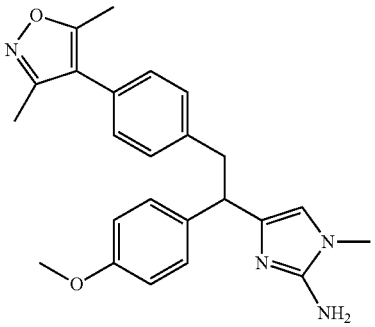 [SMILES: COc1ccc(C(Cc2ccc(-c3c(C)noc3C)cc2)c2cn(C)c(N)n2)cc1] | 4-[2-[4-(3,5-dimethylisoxazol-4-yl)phenyl]-1-(4-methoxyphenyl)ethyl]-1-methyl-1H-imidazol-2-amine |
| 55 | 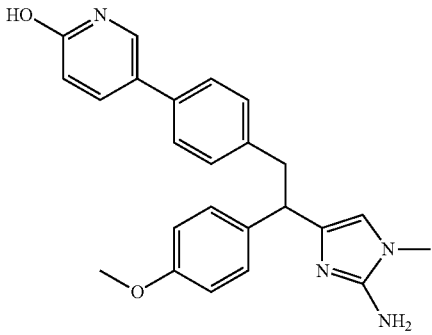 [SMILES: COc1ccc(C(Cc2ccc(-c3ccc(O)nc3)cc2)c2cn(C)c(N)n2)cc1] | 5-{4-[2-(2-amino-1-methyl-1H-imidazol-4-yl)-2-(4-methoxyphenyl)ethyl]phenyl}pyridin-2-ol |

| Ex. No. | Structure | IUPAC Name |
|---|---|---|
| 56 | 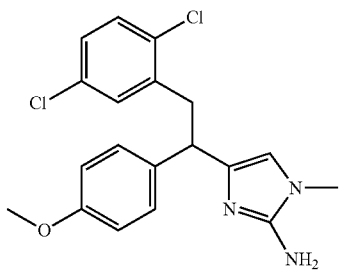 | 4-[2-(2,5-dichlorophenyl)-1-(4-methoxyphenyl)ethyl]-1-methyl-1H-imidazol-2-amine |
| 58 | 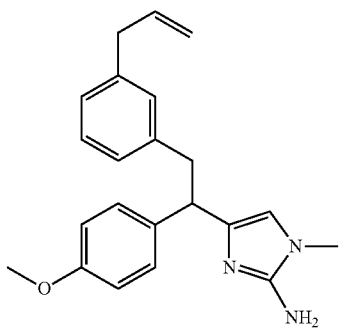 | 4-[2-(3-allylphenyl)-1-(4-methoxyphenyl)ethyl]-1-methyl-1H-imidazol-2-amine |
| 59 | 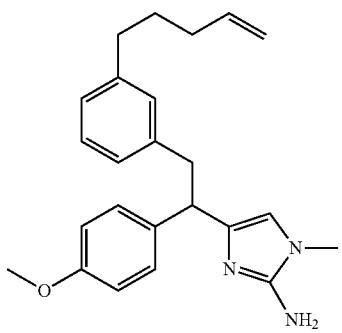 | 4-[1-(4-methoxyphenyl)-2-(3-pent-4-en-1-ylphenyl)ethyl]-1-methyl-1H-imidazol-2-amine |
| 60 | 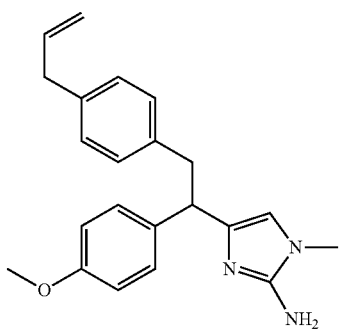 | 4-[2-(4-allylphenyl)-1-(4-methoxyphenyl)ethyl]-1-methyl-1H-imidazol-2-amine |

-continued

| Ex. No. | Structure | IUPAC Name |
|---|---|---|
| 61 | 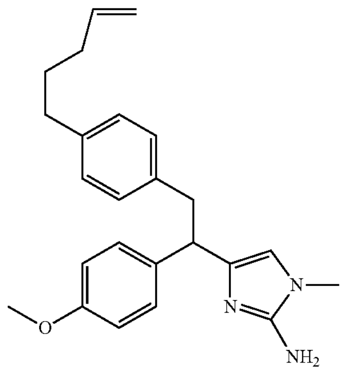 | 4-[1-(4-methoxyphenyl)-2-(4-pent-4-en-1-ylphenyl)ethyl]-1-methyl-1H-imidazol-2-amine |
| 62 | 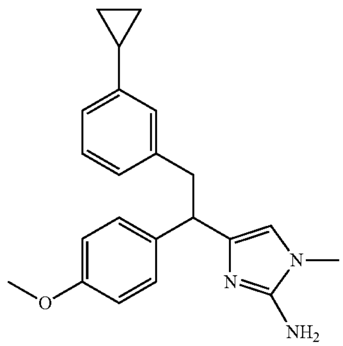 | 4-[2-(3-cyclopropylphenyl)-1-(4-methoxyphenyl)ethyl]-1-methyl-1H-imidazol-2-amine |
| 63 | 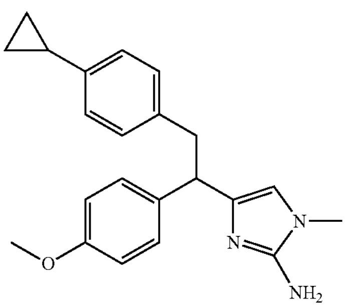 [SMILES: COc1ccc(C(Cc2ccc(C3CC3)cc2)c2cn(C)c(N)n2)cc1] | 4-[2-(4-cyclopropylphenyl)-1-(4-methoxyphenyl)ethyl]-1-methyl-1H-imidazol-2-amine |
| 66 | 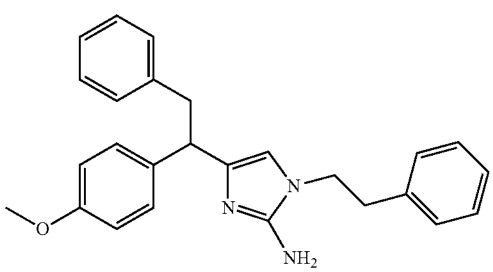 [SMILES: COc1ccc(C(Cc2ccccc2)c2cn(CCc3ccccc3)c(N)n2)cc1] | 4-[1-(4-methoxyphenyl)-2-phenylethyl]-1-(2-phenylethyl)-1H-imidazol-2-amine |
| 67 | 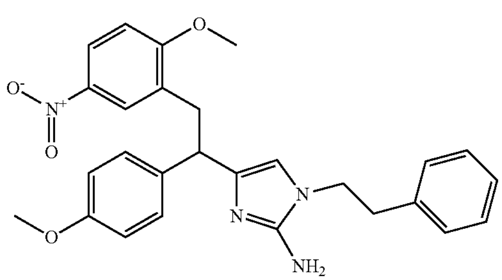 [SMILES: COc1ccc(C(Cc2cc([N+](=O)[O-])ccc2OC)c2cn(CCc3ccccc3)c(N)n2)cc1] | 4-[2-(2-methoxy-5-nitrophenyl)-1-(4-methoxyphenyl)ethyl]-1-(2-phenylethyl)-1H-imidazol-2-amine |

| Ex. No. | Structure | IUPAC Name |
|---|---|---|
| 68 | 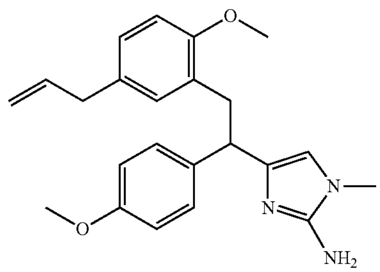 [SMILES: C=CCc1ccc(OC)c(CC(c2ccc(OC)cc2)c2cn(C)c(N)n2)c1] | 4-[2-(5-allyl-2-methoxyphenyl)-1-(4-methoxyphenyl)ethyl]-1-methyl-1H-imidazol-2-amine |
| 69 | 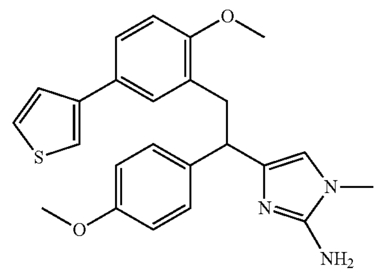 | 4-{1-(4-methoxyphenyl)-2-[2-methoxy-5-(3-thienyl)phenyl]ethyl}-1-methyl-1H-imidazol-2-amine |
| 70 | 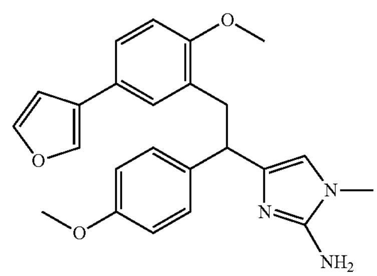 [SMILES: COc1ccc(C(Cc2cc(-c3ccsc3)ccc2OC)c2cn(C)c(N)n2)cc1] | 4-[2-[5-(3-furyl)-2-methoxyphenyl]-1-(4-methoxyphenyl)ethyl]-1-methyl-1H-imidazol-2-amine |
| 71 | 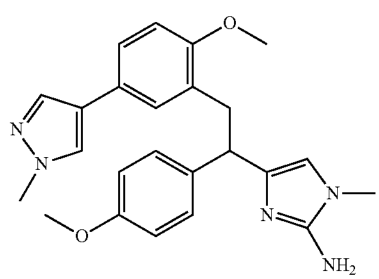 [SMILES: COc1ccc(C(Cc2cc(-c3cnn(C)c3)ccc2OC)c2cn(C)c(N)n2)cc1] | 4-[2-[2-methoxy-5-(1-methyl-1H-pyrazol-4-yl)phenyl]-1-(4-methoxyphenyl)ethyl]-1-methyl-1H-imidazol-2-amine |
| 72 | 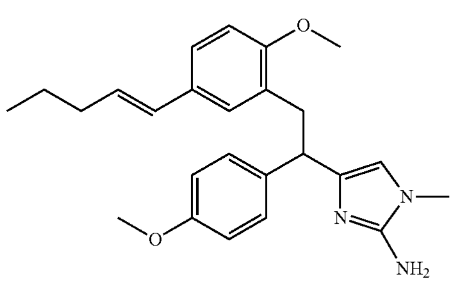 [SMILES: CCC/C=C/c1ccc(OC)c(CC(c2ccc(OC)cc2)c2cn(C)c(N)n2)c1] | 4-[2-{2-methoxy-5-[(1E)-pent-1-en-1-yl]phenyl}-1-(4-methoxyphenyl)ethyl]-1-methyl-1H-imidazol-2-amine |

| Ex. No. | Structure | IUPAC Name |
|---|---|---|
| 73 | 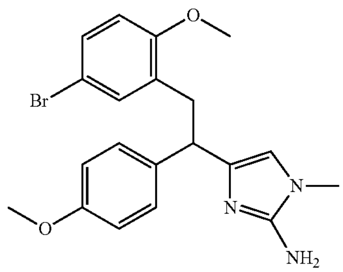 | 4-[2-(5-bromo-2-methoxyphenyl)-1-(4-methoxyphenyl)ethyl]-1-methyl-1H-imidazol-2-amine |
| 74 | 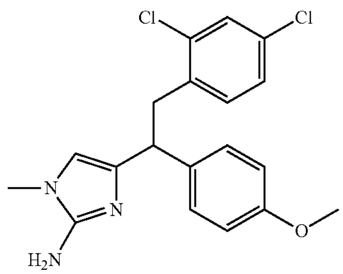 | 4-[2-(2,4-dichlorophenyl)-1-(4-methoxyphenyl)ethyl]-1-methyl-1H-imidazol-2-amine |
| 75 | 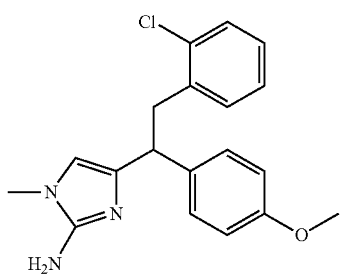 | 4-[2-(2-chlorophenyl)-1-(4-methoxyphenyl)ethyl]-1-methyl-1H-imidazol-2-amine |
| 78 | 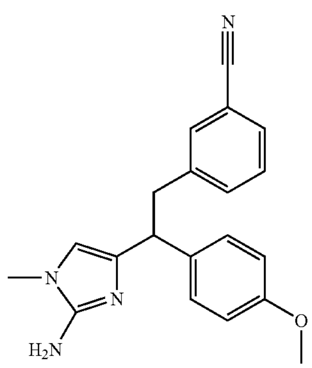 | 3-[2-(2-amino-1-methyl-1H-imidazol-4-yl)-2-(4-methoxyphenyl)ethyl]benzonitrile |
| 79 | 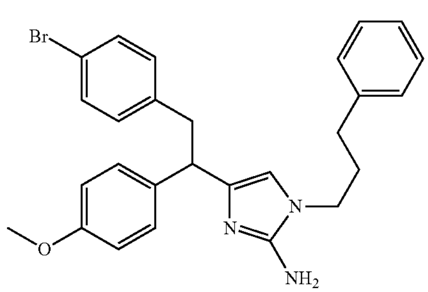 [SMILES: COc1ccc(C(Cc2ccc(Br)cc2)c2cn(CCCc3ccccc3)c(N)n2)cc1] | 4-[2-(4-bromophenyl)-1-(4-methoxyphenyl)ethyl]-1-(3-phenylpropyl)-1H-imidazol-2-amine |

| Ex. No. | Structure | IUPAC Name |
| --- | --- | --- |
| 80 | 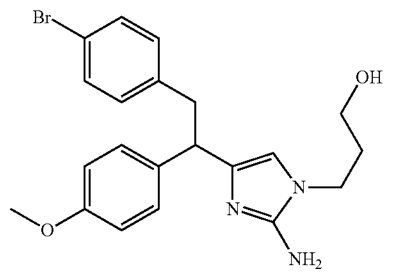 [SMILES: COc1ccc(C(Cc2ccc(Br)cc2)c2cn(CCCO)c(N)n2)cc1] | 3-{2-amino-4-[2-(4-bromophenyl)-1-(4-methoxyphenyl)ethyl]-1H-imidazol-1-yl}propan-1-ol |
| 81 | 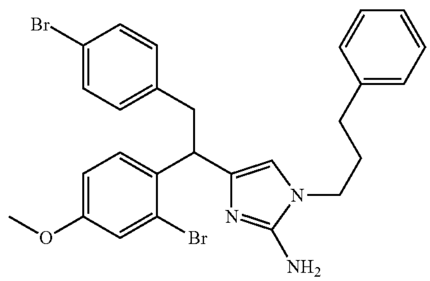 [SMILES: COc1ccc(C(Cc2ccc(Br)cc2)c2cn(CCCc3ccccc3)c(N)n2)c(Br)c1] | 4-[1-(2-bromo-4-methoxyphenyl)-2-(4-bromophenyl)ethyl]-1-(3-phenylpropyl)-1H-imidazol-2-amine |
| 82 | 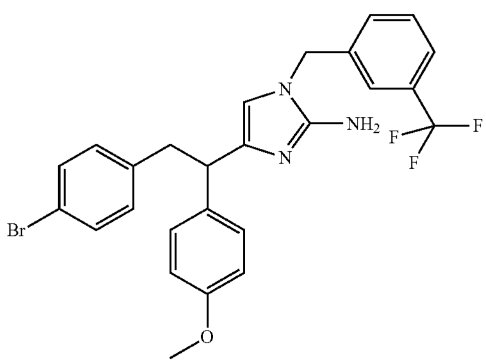 [SMILES: COc1ccc(C(Cc2ccc(Br)cc2)c2cn(Cc3cccc(C(F)(F)F)c3)c(N)n2)cc1] | 4-[2-(4-bromophenyl)-1-(4-methoxyphenyl)ethyl]-1-[3-(trifluoromethyl)benzyl]-1H-imidazol-2-amine |
| 83 | 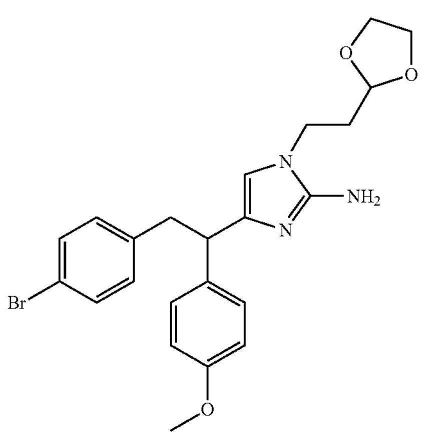 [SMILES: COc1ccc(C(Cc2ccc(Br)cc2)c2cn(CCC3OCCO3)c(N)n2)cc1] | 4-[2-(4-bromophenyl)-1-(4-methoxyphenyl)ethyl]-1-[2-(1,3-dioxolan-2-yl)ethyl]-1H-imidazol-2-amine |

| Ex. No. | Structure | IUPAC Name |
|---|---|---|
| 84 | 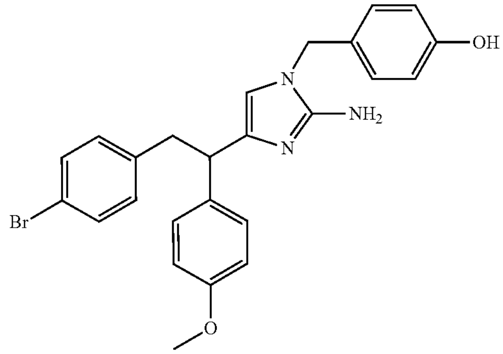 [SMILES: COc1ccc(C(Cc2ccc(Br)cc2)c2cn(Cc3ccc(O)cc3)c(N)n2)cc1] | 4-({2-amino-4-[2-(4-bromophenyl)-1-(4-methoxyphenyl)ethyl]-1H-imidazol-1-yl}methyl)phenol |
| 85 | 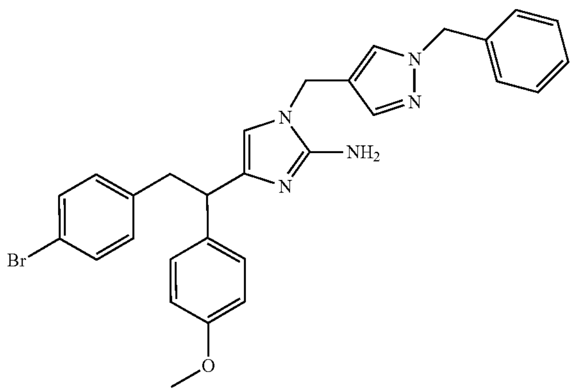 [SMILES: COc1ccc(C(Cc2ccc(Br)cc2)c2cn(Cc3cnn(Cc4ccccc4)c3)c(N)n2)cc1] | 1-[(1-benzyl-1H-pyrazol-4-yl)methyl]-4-[2-(4-bromophenyl)-1-(4-methoxyphenyl)ethyl]-1H-imidazol-2-amine |
| 86 | 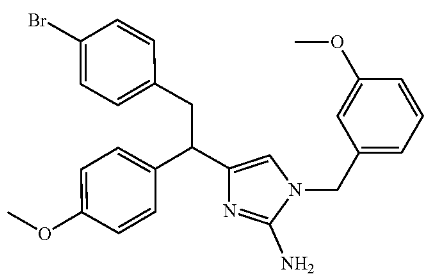 [SMILES: COc1ccc(C(Cc2ccc(Br)cc2)c2cn(Cc3cccc(OC)c3)c(N)n2)cc1] | 4-[2-(4-bromophenyl)-1-(4-methoxyphenyl)ethyl]-1-(3-methoxybenzyl)-1H-imidazol-2-amine |
| 87 | 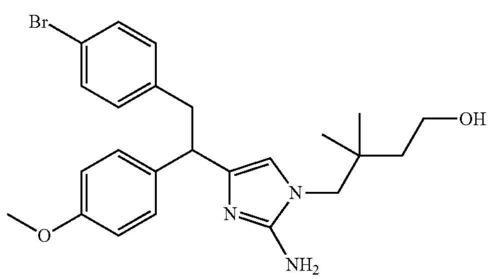 [SMILES: COc1ccc(C(Cc2ccc(Br)cc2)c2cn(CC(C)(C)CCO)c(N)n2)cc1] | 4-{2-amino-4-[2-(4-bromophenyl)-1-(4-methoxyphenyl)ethyl]-1H-imidazol-1-yl}-3,3-dimethylbutan-1-ol |
| 88 | 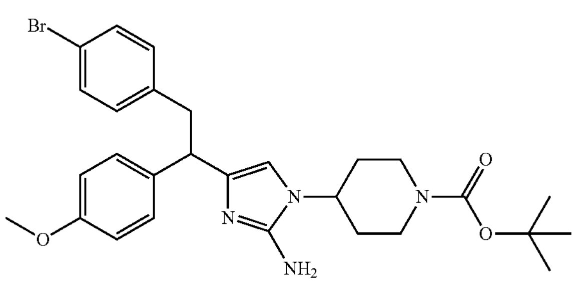 [SMILES: COc1ccc(C(Cc2ccc(Br)cc2)c2cn(C3CCN(C(=O)OC(C)(C)C)CC3)c(N)n2)cc1] | tert-butyl 4-{2-amino-4-[2-(4-bromophenyl)-1-(4-methoxyphenyl)ethyl]-1H-imidazol-1-yl}piperidine-1-carboxylate |

| Ex. No. | Structure | IUPAC Name |
|---|---|---|
| 89 | 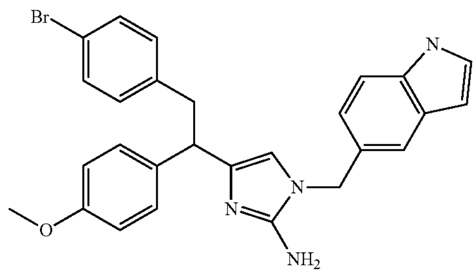 [SMILES: COc1ccc(C(Cc2ccc(Br)cc2)c2cn(Cc3ccc4[nH]ccc4c3)c(N)n2)cc1] | 4-[2-(4-bromophenyl)-1-(4-methoxyphenyl)ethyl]-1-(1H-indol-5-ylmethyl)-1H-imidazol-2-amine |
| 90 | 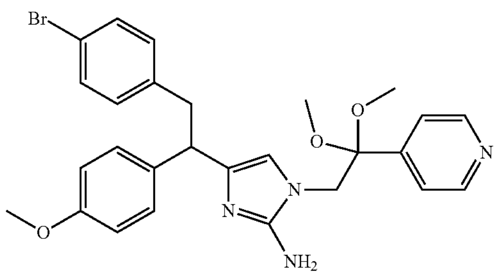 [SMILES: COc1ccc(C(Cc2ccc(Br)cc2)c2cn(CC(OC)(OC)c3ccncc3)c(N)n2)cc1] | 4-[2-(4-bromophenyl)-1-(4-methoxyphenyl)ethyl]-1-(2,2-dimethoxy-2-pyridin-4-ylethyl)-1H-imidazol-2-amine |
| 91 | 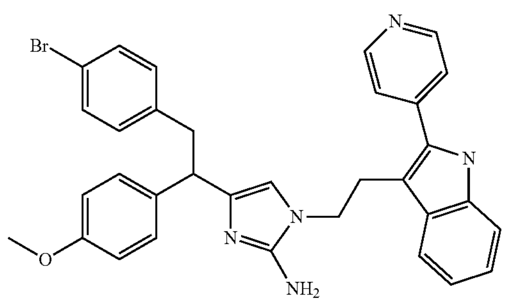 [SMILES: COc1ccc(C(Cc2ccc(Br)cc2)c2cn(CCc3c(-c4ccncc4)[nH]c4ccccc34)c(N)n2)cc1] | 4-[2-(4-bromophenyl)-1-(4-methoxyphenyl)ethyl]-1-[2-(2-pyridin-4-yl-1H-indol-3-yl)ethyl]-1H-imidazol-2-amine |
| 92 | 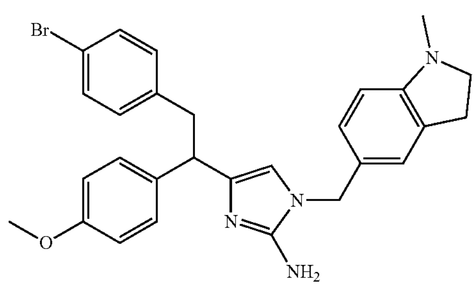 [SMILES: COc1ccc(C(Cc2ccc(Br)cc2)c2cn(Cc3ccc4c(c3)CCN4C)c(N)n2)cc1] | 4-[2-(4-bromophenyl)-1-(4-methoxyphenyl)ethyl]-1-[(1-methyl-2,3-dihydro-1H-indol-5-yl)methyl]-1H-imidazol-2-amine |
| 95 | 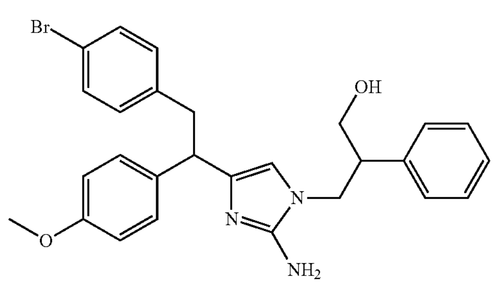 [SMILES: COc1ccc(C(Cc2ccc(Br)cc2)c2cn(CC(CO)c3ccccc3)c(N)n2)cc1] | 3-{2-amino-4-[2-(4-bromophenyl)-1-(4-methoxyphenyl)ethyl]-1H-imidazol-1-yl}-2-phenylpropan-1-ol |

| Ex. No. | Structure | IUPAC Name |
|---|---|---|
| 96 | 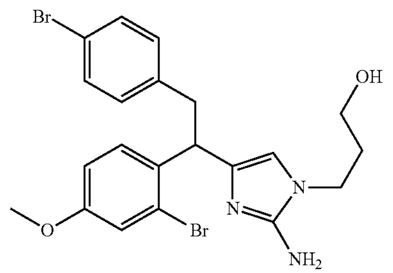 [SMILES: COc1ccc(C(Cc2ccc(Br)cc2)c2cn(CCCO)c(N)n2)c(Br)c1] | 3-{2-amino-4-[1-(2-bromo-4-methoxyphenyl)-2-(4-bromophenyl)ethyl]-1H-imidazol-1-yl}propan-1-ol |
| 97 | 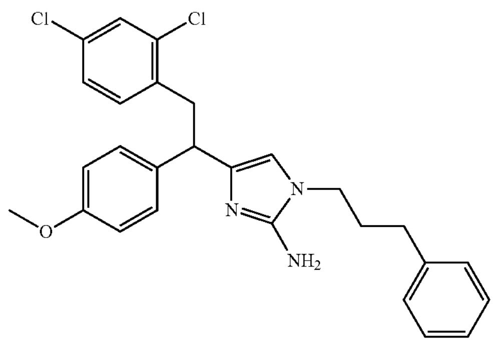 [SMILES: COc1ccc(C(Cc2ccc(Cl)cc2Cl)c2cn(CCCc3ccccc3)c(N)n2)cc1] | 4-[2-(2,4-dichlorophenyl)-1-(4-methoxyphenyl)ethyl]-1-(3-phenylpropyl)-1H-imidazol-2-amine |
| 98 | 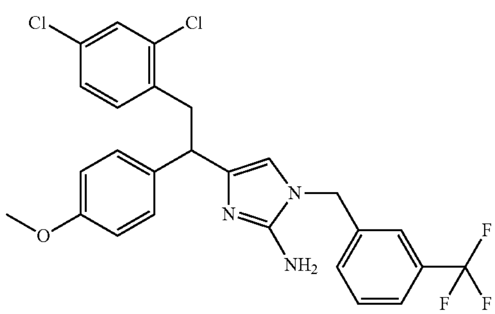 [SMILES: COc1ccc(C(Cc2ccc(Cl)cc2Cl)c2cn(Cc3cccc(C(F)(F)F)c3)c(N)n2)cc1] | 4-[2-(2,4-dichlorophenyl)-1-(4-methoxyphenyl)ethyl]-1-[3-(trifluoromethyl)benzyl]-1H-imidazol-2-amine |
| 99 | 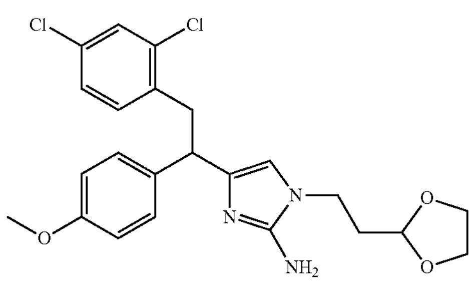 [SMILES: COc1ccc(C(Cc2ccc(Cl)cc2Cl)c2cn(CCC3OCCO3)c(N)n2)cc1] | 4-[2-(2,4-dichlorophenyl)-1-(4-methoxyphenyl)ethyl]-1-[2-(1,3-dioxolan-2-yl)ethyl]-1H-imidazol-2-amine |
| 101 | 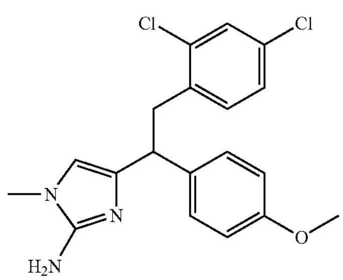 | 4-[2-(2,4-dichlorophenyl)-1-(4-methoxyphenyl)ethyl]-1-methyl-1H-imidazol-2-amine |

| Ex. No. | Structure | IUPAC Name |
|---|---|---|
| 107 | 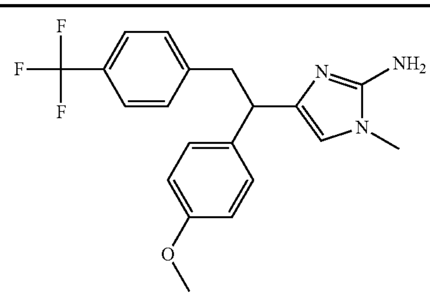 | 4-{1-(4-methoxyphenyl)-2-[4-(trifluoromethyl)phenyl]ethyl}-1-methyl-1H-imidazol-2-amine |
| 108 | 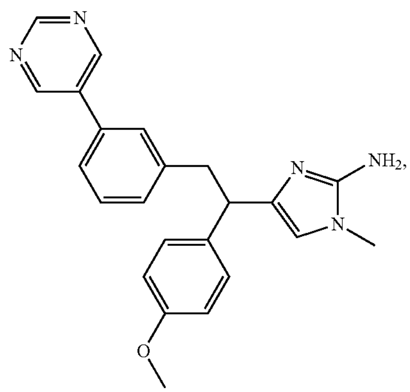 | 4-[1-(4-methoxyphenyl)-2-(3-pyrimidin-5-ylphenyl)ethyl]-1-methyl-1H-imidazol-2-amine and |
| 109 | 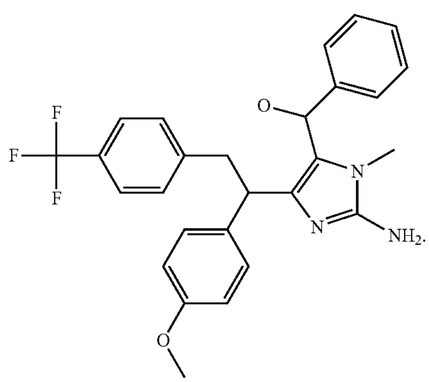 [SMILES: COc1ccc(C(Cc2ccc(C(F)(F)F)cc2)c2nc(N)n(C)c2C(O)c2ccccc2)cc1] | (2-amino-4-{1-(4-methoxyphenyl)-2-[4-(trifluoromethyl)phenyl]ethyl}-1-methyl-1H-imidazol-5-yl)(phenyl)methanol. |

11. A pharmaceutical composition comprising a therapeutically effective amount of a compound of any of claims 1 to 10, or a pharmaceutically acceptable salt thereof, and a pharmaceutically acceptable carrier.

\* \* \* \* \*